(12) United States Patent
Hata et al.

(10) Patent No.: US 7,928,215 B2
(45) Date of Patent: Apr. 19, 2011

(54) METHODS OF SCREENING FOR COMPOUNDS THAT INHIBIT THE BIOSYNTHESIS OF GPI IN MALARIA PARASITES

(75) Inventors: Katsura Hata, Tsukuba (JP); Kaoru Ogawa, Tsukuba (JP); Itaru Tsukada, Ushiku (JP); Kazutaka Nakamoto, Tsukuba (JP); Koji Sagane, Tsukuba (JP); Keigo Tanaka, Tsukuba (JP); Kappei Tsukahara, Tsukuba (JP); Toshihiro Horii, Toyonaka (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 935 days.

(21) Appl. No.: 10/535,928

(22) PCT Filed: Nov. 21, 2003

(86) PCT No.: PCT/JP03/14920
§ 371 (c)(1),
(2), (4) Date: Dec. 9, 2005

(87) PCT Pub. No.: WO2004/048567
PCT Pub. Date: Jun. 10, 2004

(65) Prior Publication Data
US 2006/0172404 A1    Aug. 3, 2006

Related U.S. Application Data

(60) Provisional application No. 60/428,589, filed on Nov. 22, 2002.

(51) Int. Cl.
*C07H 21/02* (2006.01)
*C07H 21/04* (2006.01)
*C12Q 1/00* (2006.01)

(52) U.S. Cl. ............ 536/23.7; 536/23.1; 536/24.3; 536/24.32; 435/4; 435/7.8; 435/32; 424/9.1; 424/9.2; 424/184.1; 424/191.1; 424/265.1; 424/268.1

(58) Field of Classification Search ............... 536/23.1, 536/23.7, 24.3, 24.32; 424/9.1, 9.2, 184.1, 424/185.1, 191.1, 265.1, 268.1; 435/4, 7.8, 435/32
See application file for complete search history.

(56) References Cited

U.S. PATENT DOCUMENTS

| | | |
|---|---|---|
| 2002/0019520 A1 | 2/2002 | Mao et al. |
| 2004/0038239 A1 | 2/2004 | Tsukahara et al. |
| 2006/0234283 A1 | 10/2006 | Tsukahara et al. |
| 2006/0234349 A1 | 10/2006 | Tsukahara et al. |
| 2006/0240429 A1 | 10/2006 | Tsukahara et al. |
| 2008/0166765 A1 | 7/2008 | Tsukahara et al. |
| 2008/0261272 A1 | 10/2008 | Tsukahara et al. |
| 2009/0098636 A1 | 4/2009 | Tsukahara et al. |
| 2009/0117586 A1 | 5/2009 | Tsukahara et al. |
| 2009/0325228 A1 | 12/2009 | Tsukahara et al. |

FOREIGN PATENT DOCUMENTS

| | | |
|---|---|---|
| WO | WO 98/14583 A2 | 4/1998 |
| WO | WO 00/39342 A2 | 7/2000 |
| WO | WO 01/13923 A1 | 3/2001 |
| WO | WO 02/04626 A1 | 1/2002 |
| WO | WO 02/052014 A2 | 7/2002 |
| WO | WO 2004/046604 A1 | 6/2004 |

OTHER PUBLICATIONS

Brophy, Victoria Hertle, et al.; "Identification of *Cryptosporidium parvum* Dihydrofolate Reductase Inhibitors by Complementation in *Saccharomyces cerevisiae*;" *Antimicrobial Agents and Chemotherapy*; Apr. 2000; pp. 1019-1028; 44:4.

Carlton, Jane M., et al.; "Genome sequence and comparative analysis of the model rodent malaria parasite *Plasmodium yoelii yoelii*;" *Nature*; Oct. 3, 2002; pp. 512-519; 419:6906.

Delorenzi, Mauro, et al.; "Genes for Glycosylphosphatidylinositol Toxin Biosynthesis in *Plasmodium falciparum*;" *Infection and Immunity*; Aug. 2002; pp. 4510-4522; 70:8.

Gardner, Malcolm J., et al.; "Genome sequence of the human malaria parasite *Plasmodium falciparum*;" *Nature*; Oct. 3, 2002; pp. 498-511; 419:6906.

Gerold, Peter, et al.; "Biosynthesis of glycosylphophatidylinositols of *Plasmodium falciparum* in a cell-free incubation system: inositol acylation is needed for mannosylation of glycosylphophatidylinositols;" *Biochemical Journal*; Dec. 15, 1999; pp. 731-738; 344, part 3.

Hall, N., et al.; "Sequence of *Plasmodium falciparum* chromosomes 1, 3-9 and 13;" *Nature*; Oct. 3, 2002; pp. 527-531; 419:6906.

Hall, N., et al.; Sequence Listing; EMBL Accession No. CR382399; Apr. 17, 2005.

Leidich, Steven D., et al.; "Temperature-sensitive Yeast GPI Anchoring Mutants *gpi2* and *gpi3* Are Defective in the Synthesis of *N*-Acetylglucosaminyl Phosphatidylinositol;" *The Journal of Biological Chemistry*; Jun. 2, 1995; pp. 13029-13035; 270:22.

Leidich, Steven D., et al.; Sequence Listing; EMBL Accession No. U23788; Oct. 19, 1995.

Naik, Ramachandra S., et al.; "Developmental Stage-specific Biosynthesis of Glycosylphosphatidylinositol Anchors in Intraerythrocytic *Plasmodium falciparum* and Its Inhibition in a Novel Manner by Mannosamine;" *The Journal of Biological Chemistry*; Aug. 11, 2000; pp. 24506-24511; 275:32.

(Continued)

*Primary Examiner* — Rodney P. Swartz
(74) *Attorney, Agent, or Firm* — Kilpatrick Townsend & Stockton LLP

(57) ABSTRACT

The present inventors succeeded in isolating GWT1 (Pf-GWT1), which is one of the enzymes involved in GPI biosynthesis in the malaria parasite *P. falciparum*. In addition, the inventors revealed that degenerate mutant DNAs, with a lower AT content than the DNA encoding the PfGWT1 protein, can complement the phenotype of GWT1-deficient yeast. Based on the findings, the present invention provides the GWT1 protein of malaria parasites and the use of the protein in methods of screening for antimalarial drugs. The present invention also provides degenerate mutant DNAs encoding proteins involved in GPI biosynthesis, and which have a lower AT content than the original DNAs. The present invention also provides methods of screening for antimalarial drugs which use the degenerate mutant DNAs.

23 Claims, 3 Drawing Sheets

OTHER PUBLICATIONS

Pan, Weiqing, et al.; "Vaccine candidate MSP-1 from *Plasmodium falciparum*: a redesigned 4917 bp polynucleotide enables synthesis and isolation of full-length protein for *Escherichia coli* and mammalian cells;" *Nucleic Acids Research*; Feb. 15, 1999; pp. 1094-1103; 27:4.

Shams-Eldin, Hosam; Sequence Listing; EMBL Accession No. AJ401202; Jul. 1, 2000.

Shams-Eldin, Hosam, et al.; "The GPI1 homologue from *Plasmodium falciparum* complements a *Saccharomyces cerevisiae* GPI1 anchoring mutant;" *Molecular and Biochemical Parasitology*; Mar. 2002; pp. 73-81; 120:1.

Shams-Eldin, Hosam, et al.; Sequence Listing; EMBL Accession No. AJ249657; Feb. 11, 2002.

Umemura, Mariko, et al.; "*GWT1* Gene Is Required for Inositol Acylation of Glycosylphosphatidylinositol Anchors in Yeast;" *The Journal of Biological Chemistry*; Jun. 27, 2002; pp. 23639-23647; 278:26.

Withers-Martinez, Chrislaine, et al.; "PCR-based gene synthesis as an efficient approach for expression of the A+T-rich malaria genome;" *Protein Engineering*; Dec. 12, 1999; pp. 1113-1120; 12:12.

Wooden, Jason M., et al.; "Analysis in yeast of antimalaria drugs that target the dihydrofolate reductase of *Plasmodium falciparum*;" *Molecular and Biochemical Parasitology*; Mar. 1997; pp. 25-40; 85:1.

Zhang, Hanbang, et al.; "Analysis of the Antimalarial Drug Resistance Protein Pfcrt Expressed in Yeast;" *The Journal of Biological Chemistry*; Dec. 20, 2002; pp. 49767-49775; 277:51.

Sequence Listings; Discloses the sequences of PfPIG-A, -B, -M, -O, PfGAA1 and PfDPM1, all 100% identical to Seq ID Nos. 11,13,15,17,21, respectively. [http://bioinf.wehi.edu.au/folders/mauro/GPI/proteins.seq.].

Cerevachi, I., et al., GenBank Accession No. AL844505 (GI:23498324): (http://www.ncbi.nlm.nih.gov/entrez/viewer.fcgi?23498324:OLD12:31840), 530 pgs. (Oct. 2, 2002).

Cerevachi, I., et al., GenBank Accession No. CAD50425: (http://www.ncbi.nlm.nih.gov/entrez/viewer.fcgi?db=protein&id=23498474), 2 pgs. (Jan. 29, 2003).

Smith, T., et al., "Substrate Specificity of the *Plasmodium falciparum* Glycosylphosphatidylinositol Biosynthetic Pathway and Inhibition by Species-Specific Suicide Substrates," *Biochemistry*, vol. 41, pp. 12395-12406 (2002).

Bowman, S., et al., EMBL Accession No. AL096783, 22 pgs. (Submitted: Jul. 2, 1999, Created: Jul. 2, 1999).

Uemura, H., EMBL Accession No. D29645, 2 pgs. (Submitted: Mar. 24, 1994, Created: Nov. 25, 1995).

YEp352GAPII-pfGWT1

YEp352GAPII-opfGWT1

SEQUENCE LISTING

```
<160> NUMBER OF SEQ ID NOS: 55

<210> SEQ ID NO 1
<211> LENGTH: 2625
<212> TYPE: DNA
<213> ORGANISM: Plasmodium falciparum
<220> FEATURE:
<221> NAME/KEY: CDS
<222> LOCATION: (1)...(2625)

<400> SEQUENCE: 1 atg agc aac atg aat ata ctt gcg tat ctt ttg ata tgt ccc ttt aac        48
Met Ser Asn Met Asn Ile Leu Ala Tyr Leu Leu Ile Cys Pro Phe Asn
 1               5                  10                  15 tta ata tat ata ttt gac ctt cct tca tat ata cct gag tta aat aaa        96
Leu Ile Tyr Ile Phe Asp Leu Pro Ser Tyr Ile Pro Glu Leu Asn Lys
             20                  25                  30 aag ctg gag aat gac gag gtg ttt ata tat gga aaa gaa ata aga aag       144
Lys Leu Glu Asn Asp Glu Val Phe Ile Tyr Gly Lys Glu Ile Arg Lys
         35                  40                  45 aat gaa tct gca tat tct tta cat tat gaa aaa tat tta tat gaa tta       192
Asn Glu Ser Ala Tyr Ser Leu His Tyr Glu Lys Tyr Leu Tyr Glu Leu
     50                  55                  60 tca aga aga tat tat gag ata ata tta aaa tat aat aag gag ctc ggg       240
Ser Arg Arg Tyr Tyr Glu Ile Ile Leu Lys Tyr Asn Lys Glu Leu Gly
 65                  70                  75                  80 gtt aat caa gaa aaa gaa tat aat tta ata ata agt aga gag ata gat       288
Val Asn Gln Glu Lys Glu Tyr Asn Leu Ile Ile Ser Arg Glu Ile Asp
                 85                  90                  95 aaa aaa aaa aaa aaa caa aaa aat agt aca caa gga gaa tat aat aat       336
```

```
Lys Lys Lys Lys Lys Gln Lys Asn Ser Thr Gln Gly Glu Tyr Asn Asn
            100                 105                 110 gat gat gat aat aat tgg aaa tta ttc caa ata tat gag aag gaa gaa        384
Asp Asp Asp Asn Asn Trp Lys Leu Phe Gln Ile Tyr Glu Lys Glu Glu
            115                 120                 125 ccc aga tca tac gaa tta ata cgt gtt gag att tac aaa aaa gat att        432
Pro Arg Ser Tyr Glu Leu Ile Arg Val Glu Ile Tyr Lys Lys Asp Ile
        130                 135                 140 ctt tta att tat aaa aat gaa aaa acc aaa tca tca ata aaa ttt ata        480
Leu Leu Ile Tyr Lys Asn Glu Lys Thr Lys Ser Ser Ile Lys Phe Ile
145                 150                 155                 160 ata aag aaa aga aaa gat ata aaa aat tat ttc tca tta tgt tat caa        528
Ile Lys Lys Arg Lys Asp Ile Lys Asn Tyr Phe Ser Leu Cys Tyr Gln
                165                 170                 175 aat tgt ata aat aaa tta gat aaa aat gat tat aat att tta aaa agt        576
Asn Cys Ile Asn Lys Leu Asp Lys Asn Asp Tyr Asn Ile Leu Lys Ser
            180                 185                 190 aca ata aat aat agt aaa gaa aat ata att aat agt gct tat ata tat        624
Thr Ile Asn Asn Ser Lys Glu Asn Ile Ile Asn Ser Ala Tyr Ile Tyr
        195                 200                 205 atg tat ata ata ttt ttc ttt tta tgt ata tat gta gaa aaa aat tta        672
Met Tyr Ile Ile Phe Phe Phe Leu Cys Ile Tyr Val Glu Lys Asn Leu
210                 215                 220 ttt tta tac ttt cct ata tta tta caa aag tat gaa ata cta aca aca        720
Phe Leu Tyr Phe Pro Ile Leu Leu Gln Lys Tyr Glu Ile Leu Thr Thr
225                 230                 235                 240 tta ttt att tta ttt att cct cta att ctt ttt gtt ttt ttt tat ttt        768
Leu Phe Ile Leu Phe Ile Pro Leu Ile Leu Phe Val Phe Phe Tyr Phe
                245                 250                 255 tat ttt act ata atc aag ttg ata tgt tct tgt cta gtt tta tat gta        816
Tyr Phe Thr Ile Ile Lys Leu Ile Cys Ser Cys Leu Val Leu Tyr Val
            260                 265                 270 aca ttt caa tta att tat tat act caa ggt atg cct ata tat atg gaa        864
Thr Phe Gln Leu Ile Tyr Tyr Thr Gln Gly Met Pro Ile Tyr Met Glu
        275                 280                 285 cat agc ata ttg aaa cat aaa gaa aaa gaa gaa att tgt gat gaa aaa        912
His Ser Ile Leu Lys His Lys Glu Lys Glu Glu Ile Cys Asp Glu Lys
290                 295                 300 gaa gaa att tgt gat gaa aaa gaa gaa att tgt gat gaa aaa gaa gaa        960
Glu Glu Ile Cys Asp Glu Lys Glu Glu Ile Cys Asp Glu Lys Glu Glu
305                 310                 315                 320 att tgt gat gaa aaa gaa gaa att tgt gat gaa aaa gaa gaa att tgt        1008
Ile Cys Asp Glu Lys Glu Glu Ile Cys Asp Glu Lys Glu Glu Ile Cys
                325                 330                 335 gat gaa aaa gaa gaa att ctt gat aaa aaa aaa aaa att cat gaa aaa        1056
Asp Glu Lys Glu Glu Ile Leu Asp Lys Lys Lys Lys Ile His Glu Lys
            340                 345                 350 aaa aaa aaa att cat gat aaa aaa gaa gaa att gat gaa aaa aaa aaa        1104
Lys Lys Lys Ile His Asp Lys Lys Glu Glu Ile Asp Glu Lys Lys Lys
        355                 360                 365 aaa att cat gat aaa aaa gac gaa agt cat gat aaa aat gaa gac ata        1152
Lys Ile His Asp Lys Lys Asp Glu Ser His Asp Lys Asn Glu Asp Ile
370                 375                 380 aca tat cct gtt caa tat aat ata gaa aat gat tta tgg tac agc tca        1200
Thr Tyr Pro Val Gln Tyr Asn Ile Glu Asn Asp Leu Trp Tyr Ser Ser
385                 390                 395                 400 aaa aat gta gat att aaa atg tat tca tct tca aat aaa gga gaa gaa        1248
Lys Asn Val Asp Ile Lys Met Tyr Ser Ser Ser Asn Lys Gly Glu Glu
                405                 410                 415 tat att ata cag aat aca tta aaa cat ttt aga tta atg aat atg tgt        1296
```

```
Tyr Ile Ile Gln Asn Thr Leu Lys His Phe Arg Leu Met Asn Met Cys
            420                 425                 430 atg aca tat ata tgt atc ttt gct gtt gat ttt tat ttc ttt cca aat      1344
Met Thr Tyr Ile Cys Ile Phe Ala Val Asp Phe Tyr Phe Phe Pro Asn
        435                 440                 445 cat ttt tgt aaa tcc tat tat tat gga aat aca cta atg gat ata ggg      1392
His Phe Cys Lys Ser Tyr Tyr Tyr Gly Asn Thr Leu Met Asp Ile Gly
    450                 455                 460 ata ggt gct tct ata agc tcc agt gca tat tct caa gaa ata aaa aag      1440
Ile Gly Ala Ser Ile Ser Ser Ser Ala Tyr Ser Gln Glu Ile Lys Lys
465                 470                 475                 480 ttt aca tat ata aaa gag aag aaa aga ata att gaa tta aaa cat ata      1488
Phe Thr Tyr Ile Lys Glu Lys Lys Arg Ile Ile Glu Leu Lys His Ile
            485                 490                 495 gtt tta ttt att tta gga ata tct aga ttt att gga ata tat ctt ttt      1536
Val Leu Phe Ile Leu Gly Ile Ser Arg Phe Ile Gly Ile Tyr Leu Phe
        500                 505                 510 aat tat aat tat aat ata agt gaa tat gga ata cat tgg aat ttc ttt      1584
Asn Tyr Asn Tyr Asn Ile Ser Glu Tyr Gly Ile His Trp Asn Phe Phe
    515                 520                 525 tta aca tta tgt act aca ttt ctt ata tct aat ata tgt ttt att tta      1632
Leu Thr Leu Cys Thr Thr Phe Leu Ile Ser Asn Ile Cys Phe Ile Leu
530                 535                 540 tta aaa agg ata cgt tat att ttt ctt ttt agt ata atc tct ata att      1680
Leu Lys Arg Ile Arg Tyr Ile Phe Leu Phe Ser Ile Ile Ser Ile Ile
545                 550                 555                 560 ctt ttt gaa ata gcc ata tac tat ttt gac tta cat aat tat ata tta      1728
Leu Phe Glu Ile Ala Ile Tyr Tyr Phe Asp Leu His Asn Tyr Ile Leu
            565                 570                 575 tta aaa aat gat aga tta aat ttc ttt tca tca aac aaa gaa ggc tta      1776
Leu Lys Asn Asp Arg Leu Asn Phe Phe Ser Ser Asn Lys Glu Gly Leu
        580                 585                 590 ttt aat att ata ggt tct gtt aat ttg tat tta ttt tct ttc tca tta      1824
Phe Asn Ile Ile Gly Ser Val Asn Leu Tyr Leu Phe Ser Phe Ser Leu
    595                 600                 605 ttt aaa tat tta aca aaa caa agg aca tac ata aca acc tcg aac att      1872
Phe Lys Tyr Leu Thr Lys Gln Arg Thr Tyr Ile Thr Thr Ser Asn Ile
610                 615                 620 cca aaa aat aaa aag gat atg aat aat tct atg tat tca aag aac ggt      1920
Pro Lys Asn Lys Lys Asp Met Asn Asn Ser Met Tyr Ser Lys Asn Gly
625                 630                 635                 640 aac cac aca aat agc aat ata aat aat agg aat cat aaa att gta att      1968
Asn His Thr Asn Ser Asn Ile Asn Asn Arg Asn His Lys Ile Val Ile
            645                 650                 655 cgg aat aat cat ata aat aaa tat gaa caa gat aac aca aat aag tat      2016
Arg Asn Asn His Ile Asn Lys Tyr Glu Gln Asp Asn Thr Asn Lys Tyr
        660                 665                 670 att aat aaa caa ata aat aat aat aag aat aaa ctt gat gaa gaa gaa      2064
Ile Asn Lys Gln Ile Asn Asn Asn Lys Asn Lys Leu Asp Glu Glu Glu
    675                 680                 685 aaa tta aaa aaa tta aaa aaa tta aaa aac aaa aaa aaa aat tta aaa      2112
Lys Leu Lys Lys Leu Lys Lys Leu Lys Asn Lys Lys Lys Asn Leu Lys
690                 695                 700 aaa aaa att aaa tat tat ttg tta tac ctt caa tat ata ata aat ata      2160
Lys Lys Ile Lys Tyr Tyr Leu Leu Tyr Leu Gln Tyr Ile Ile Asn Ile
705                 710                 715                 720 tat aaa gaa gaa tat tat act att tat tat aat ata aaa tta att ata      2208
Tyr Lys Glu Glu Tyr Tyr Thr Ile Tyr Tyr Asn Ile Lys Leu Ile Ile
            725                 730                 735 tca tct ttt att ttt tat tta tta cat ata att ctt aat tta tat aaa      2256
```

```
Ser Ser Phe Ile Phe Tyr Leu Leu His Ile Ile Leu Asn Leu Tyr Lys
            740                 745                 750 aat tat agt gtg cgt ata tta tgt aat gca aat tat att ttt tta ata    2304
Asn Tyr Ser Val Arg Ile Leu Cys Asn Ala Asn Tyr Ile Phe Leu Ile
        755                 760                 765 aca tca ttg ggt ttg ttt tct tgt gcc ttg agt ttt tcc tta gaa gat    2352
Thr Ser Leu Gly Leu Phe Ser Cys Ala Leu Ser Phe Ser Leu Glu Asp
770                 775                 780 ata tta tta aga tat aaa aaa tat aaa ata aat att gat ata aca gta    2400
Ile Leu Leu Arg Tyr Lys Lys Tyr Lys Ile Asn Ile Asp Ile Thr Val
785                 790                 795                 800 ttg gat aag ata aat aaa aat aca ttg ata gtt ttt ctt ttc tcg aat    2448
Leu Asp Lys Ile Asn Lys Asn Thr Leu Ile Val Phe Leu Phe Ser Asn
            805                 810                 815 ata ctt gtg ggc atg ttc aat att cta ttt caa act tta tta cct        2496
Ile Leu Val Gly Met Phe Asn Ile Leu Phe Gln Thr Leu Leu Pro
                820                 825                 830 ctt ata ttt gta ata cct ata ttg gta ttt tat tct ttc tta ata ctg    2544
Leu Ile Phe Val Ile Pro Ile Leu Val Phe Tyr Ser Phe Leu Ile Leu
        835                 840                 845 ctt ttt aca aaa tgc tta cca cct tcc ata cgc cat cca aaa aaa aaa    2592
Leu Phe Thr Lys Cys Leu Pro Pro Ser Ile Arg His Pro Lys Lys Lys
850                 855                 860 aca cat cat gag gaa aag caa aaa aaa gaa tga                        2625
Thr His His Glu Glu Lys Gln Lys Lys Glu *
865                 870

<210> SEQ ID NO 2
<211> LENGTH: 874
<212> TYPE: PRT
<213> ORGANISM: Plasmodium falciparum

<400> SEQUENCE: 2

Met Ser Asn Met Asn Ile Leu Ala Tyr Leu Leu Ile Cys Pro Phe Asn
1               5                   10                  15

Leu Ile Tyr Ile Phe Asp Leu Pro Ser Tyr Ile Pro Glu Leu Asn Lys
            20                  25                  30

Lys Leu Glu Asn Asp Glu Val Phe Ile Tyr Gly Lys Glu Ile Arg Lys
        35                  40                  45

Asn Glu Ser Ala Tyr Ser Leu His Tyr Glu Lys Tyr Leu Tyr Glu Leu
    50                  55                  60

Ser Arg Arg Tyr Tyr Glu Ile Ile Leu Lys Tyr Asn Lys Glu Leu Gly
65                  70                  75                  80

Val Asn Gln Glu Lys Glu Tyr Asn Leu Ile Ile Ser Arg Glu Ile Asp
                85                  90                  95

Lys Lys Lys Lys Lys Gln Lys Asn Ser Thr Gln Gly Glu Tyr Asn Asn
            100                 105                 110

Asp Asp Asp Asn Asn Trp Lys Leu Phe Gln Ile Tyr Glu Lys Glu Glu
        115                 120                 125

Pro Arg Ser Tyr Glu Leu Ile Arg Val Glu Ile Tyr Lys Lys Asp Ile
    130                 135                 140

Leu Leu Ile Tyr Lys Asn Glu Lys Thr Lys Ser Ser Ile Lys Phe Ile
145                 150                 155                 160

Ile Lys Lys Arg Lys Asp Ile Lys Asn Tyr Phe Ser Leu Cys Tyr Gln
                165                 170                 175

Asn Cys Ile Asn Lys Leu Asp Lys Asn Asp Tyr Asn Ile Leu Lys Ser
            180                 185                 190

Thr Ile Asn Asn Ser Lys Glu Asn Ile Ile Asn Ser Ala Tyr Ile Tyr
```

-continued

```
                195                 200                 205
Met Tyr Ile Ile Phe Phe Phe Leu Cys Ile Tyr Val Glu Lys Asn Leu
210                 215                 220

Phe Leu Tyr Phe Pro Ile Leu Leu Gln Lys Tyr Glu Ile Leu Thr Thr
225                 230                 235                 240

Leu Phe Ile Leu Phe Ile Pro Leu Ile Leu Phe Val Phe Phe Tyr Phe
                245                 250                 255

Tyr Phe Thr Ile Ile Lys Leu Ile Cys Ser Cys Leu Val Leu Tyr Val
                260                 265                 270

Thr Phe Gln Leu Ile Tyr Tyr Thr Gln Gly Met Pro Ile Tyr Met Glu
                275                 280                 285

His Ser Ile Leu Lys His Lys Glu Lys Glu Ile Cys Asp Glu Lys
290                 295                 300

Glu Glu Ile Cys Asp Glu Lys Glu Ile Cys Asp Glu Lys Glu Glu
305                 310                 315                 320

Ile Cys Asp Glu Lys Glu Glu Ile Cys Asp Glu Lys Glu Glu Ile Cys
                325                 330                 335

Asp Glu Lys Glu Glu Ile Leu Asp Lys Lys Lys Ile His Glu Lys
                340                 345                 350

Lys Lys Lys Ile His Asp Lys Lys Glu Glu Ile Asp Glu Lys Lys Lys
                355                 360                 365

Lys Ile His Asp Lys Lys Asp Glu Ser His Asp Lys Asn Glu Asp Ile
                370                 375                 380

Thr Tyr Pro Val Gln Tyr Asn Ile Glu Asn Asp Leu Trp Tyr Ser Ser
385                 390                 395                 400

Lys Asn Val Asp Ile Lys Met Tyr Ser Ser Asn Lys Gly Glu Glu
                405                 410                 415

Tyr Ile Ile Gln Asn Thr Leu Lys His Phe Arg Leu Met Asn Met Cys
                420                 425                 430

Met Thr Tyr Ile Cys Ile Phe Ala Val Asp Phe Tyr Phe Pro Asn
                435                 440                 445

His Phe Cys Lys Ser Tyr Tyr Tyr Gly Asn Thr Leu Met Asp Ile Gly
450                 455                 460

Ile Gly Ala Ser Ile Ser Ser Ser Ala Tyr Ser Gln Glu Ile Lys Lys
465                 470                 475                 480

Phe Thr Tyr Ile Lys Glu Lys Lys Arg Ile Ile Glu Leu Lys His Ile
                485                 490                 495

Val Leu Phe Ile Leu Gly Ile Ser Arg Phe Ile Gly Ile Tyr Leu Phe
                500                 505                 510

Asn Tyr Asn Tyr Asn Ile Ser Glu Tyr Gly Ile His Trp Asn Phe Phe
                515                 520                 525

Leu Thr Leu Cys Thr Thr Phe Leu Ile Ser Asn Ile Cys Phe Ile Leu
                530                 535                 540

Leu Lys Arg Ile Arg Tyr Ile Phe Leu Phe Ser Ile Ile Ser Ile Ile
545                 550                 555                 560

Leu Phe Glu Ile Ala Ile Tyr Tyr Phe Asp Leu His Asn Tyr Ile Leu
                565                 570                 575

Leu Lys Asn Asp Arg Leu Asn Phe Phe Ser Asn Lys Glu Gly Leu
                580                 585                 590

Phe Asn Ile Ile Gly Ser Val Asn Leu Tyr Leu Phe Ser Phe Ser Leu
                595                 600                 605

Phe Lys Tyr Leu Thr Lys Gln Arg Thr Tyr Ile Thr Thr Ser Asn Ile
610                 615                 620
```

```
Pro Lys Asn Lys Lys Asp Met Asn Asn Ser Met Tyr Ser Lys Asn Gly
625                 630                 635                 640

Asn His Thr Asn Ser Asn Ile Asn Asn Arg Asn His Lys Ile Val Ile
            645                 650                 655

Arg Asn Asn His Ile Asn Lys Tyr Glu Gln Asp Asn Thr Asn Lys Tyr
            660                 665                 670

Ile Asn Lys Gln Ile Asn Asn Lys Asn Lys Leu Asp Glu Glu Glu
            675                 680                 685

Lys Leu Lys Lys Leu Lys Lys Leu Asn Lys Lys Asn Leu Lys
690                 695                 700

Lys Lys Ile Lys Tyr Tyr Leu Leu Tyr Leu Gln Tyr Ile Ile Asn Ile
705                 710                 715                 720

Tyr Lys Glu Glu Tyr Tyr Thr Ile Tyr Tyr Asn Ile Lys Leu Ile Ile
                725                 730                 735

Ser Ser Phe Ile Phe Tyr Leu Leu His Ile Ile Leu Asn Leu Tyr Lys
            740                 745                 750

Asn Tyr Ser Val Arg Ile Leu Cys Asn Ala Asn Tyr Ile Phe Leu Ile
            755                 760                 765

Thr Ser Leu Gly Leu Phe Ser Cys Ala Leu Ser Phe Ser Leu Glu Asp
    770                 775                 780

Ile Leu Arg Tyr Lys Lys Tyr Lys Ile Asn Ile Asp Ile Thr Val
785                 790                 795                 800

Leu Asp Lys Ile Asn Lys Asn Thr Leu Ile Val Phe Leu Phe Ser Asn
                805                 810                 815

Ile Leu Val Gly Met Phe Asn Ile Leu Phe Gln Thr Leu Leu Leu Pro
            820                 825                 830

Leu Ile Phe Val Ile Pro Ile Leu Val Phe Tyr Ser Phe Leu Ile Leu
            835                 840                 845

Leu Phe Thr Lys Cys Leu Pro Pro Ser Ile Arg His Pro Lys Lys Lys
            850                 855                 860

Thr His His Glu Glu Lys Gln Lys Lys Glu
865                 870

<210> SEQ ID NO 3
<211> LENGTH: 1956
<212> TYPE: DNA
<213> ORGANISM: Plasmodium vivax
<220> FEATURE:
<221> NAME/KEY: CDS
<222> LOCATION: (1)...(1956)

<400> SEQUENCE: 3 atg gcg cat ttg aac ctc ctc gtc tac ctc atc atg tgc ccc ttc aat      48
Met Ala His Leu Asn Leu Leu Val Tyr Leu Ile Met Cys Pro Phe Asn
1               5                   10                  15 gtg agg cac atg ctg gat gcg ccc agc ttc cca ttc cgg tta gga agc      96
Val Arg His Met Leu Asp Ala Pro Ser Phe Pro Phe Arg Leu Gly Ser
            20                  25                  30 aaa gca gca agt ggt gaa acc ttc acg tat gga gcg act gca aga gag     144
Lys Ala Ala Ser Gly Glu Thr Phe Thr Tyr Gly Ala Thr Ala Arg Glu
        35                  40                  45 aac ctg ggg agt tac tct ccc gca cat gac gag cta tac atg tta gag     192
Asn Leu Gly Ser Tyr Ser Pro Ala His Asp Glu Leu Tyr Met Leu Glu
    50                  55                  60 tta gcc aaa atg tac tat aaa att gtg tta aca tat aag aag gat gtt     240
Leu Ala Lys Met Tyr Tyr Lys Ile Val Leu Thr Tyr Lys Lys Asp Val
65                  70                  75                  80 agg aaa gga cag gag gag agt tac aac ttg gtg gta ggc tcc ttt ggg     288
```

```
Arg Lys Gly Gln Glu Glu Ser Tyr Asn Leu Val Val Gly Ser Phe Gly
             85                  90                  95 aag gaa gcc aaa ggg gag gtc tcc ctc caa aga gtt ctc atc aca aat    336
Lys Glu Ala Lys Gly Glu Val Ser Leu Gln Arg Val Leu Ile Thr Asn
            100                 105                 110 gat gcc gtg tac ctg tcg tac cag gat gtg caa aac gaa cgt ggg atc    384
Asp Ala Val Tyr Leu Ser Tyr Gln Asp Val Gln Asn Glu Arg Gly Ile
        115                 120                 125 caa gtt aag ata aaa agg ggg gaa ata tct tcc tat tta gac ctc cta    432
Gln Val Lys Ile Lys Arg Gly Glu Ile Ser Ser Tyr Leu Asp Leu Leu
    130                 135                 140 tcg tgg gat tct tgt ttg tat aag ctt aac tca gac gat tat aat tta    480
Ser Trp Asp Ser Cys Leu Tyr Lys Leu Asn Ser Asp Asp Tyr Asn Leu
145                 150                 155                 160 atg aag agc gca tcg gat cat agc aag cca atg gtg gtc agc aca tac    528
Met Lys Ser Ala Ser Asp His Ser Lys Pro Met Val Val Ser Thr Tyr
                165                 170                 175 cac ata tac atg ctg ctg ctg gtg ttt tct ctt tgc act tac gtg gag    576
His Ile Tyr Met Leu Leu Leu Val Phe Ser Leu Cys Thr Tyr Val Glu
            180                 185                 190 aag agc ctc ctg ctt gaa ttc cct gcg ttg aaa aag tgc caa gta ttt    624
Lys Ser Leu Leu Leu Glu Phe Pro Ala Leu Lys Lys Cys Gln Val Phe
        195                 200                 205 cta acc cta tgt ttg gtg tac tgc ccg ata atc agt tac ctt ttt ttt    672
Leu Thr Leu Cys Leu Val Tyr Cys Pro Ile Ile Ser Tyr Leu Phe Phe
    210                 215                 220 ttt tac tcc cat gtg agc cta ctt ggg gtg tta ctc gtc tat gtg ttt    720
Phe Tyr Ser His Val Ser Leu Leu Gly Val Leu Leu Val Tyr Val Phe
225                 230                 235                 240 ttt tgc ggg ctc ttc agg ggc gtc tct tgc aga agg ggg ggg cag cac    768
Phe Cys Gly Leu Phe Arg Gly Val Ser Cys Arg Arg Gly Gly Gln His
                245                 250                 255 atg ggg gag caa acg ggc caa cac acg ggc gat tgg cac acc atc cgc    816
Met Gly Glu Gln Thr Gly Gln His Thr Gly Asp Trp His Thr Ile Arg
            260                 265                 270 ggc aac cca caa ggt gat gat acg caa gag gag aga cgc aag tgt ttg    864
Gly Asn Pro Gln Gly Asp Asp Thr Gln Glu Glu Arg Arg Lys Cys Leu
        275                 280                 285 gtc cat atg agg cta gcc aac ctg tgc atc acc tac ata tgc ata ttc    912
Val His Met Arg Leu Ala Asn Leu Cys Ile Thr Tyr Ile Cys Ile Phe
    290                 295                 300 gct gtg gac ttt tat ttt ttc cca agg caa ttt tcc aag tct ttt ttt    960
Ala Val Asp Phe Tyr Phe Phe Pro Arg Gln Phe Ser Lys Ser Phe Phe
305                 310                 315                 320 ttt ggt aac act ttg atg gat tta ggg gtg ggg ggg tgc atc aca tcg   1008
Phe Gly Asn Thr Leu Met Asp Leu Gly Val Gly Gly Cys Ile Thr Ser
                325                 330                 335 agc gcg tat tct cta aac agt aaa aag ctc cat tct gcg aac cgc aag   1056
Ser Ala Tyr Ser Leu Asn Ser Lys Lys Leu His Ser Ala Asn Arg Lys
            340                 345                 350 gga cac cta atc gat tgg aag cat ttc att tta ttt ttc ctt gga ata   1104
Gly His Leu Ile Asp Trp Lys His Phe Ile Leu Phe Phe Leu Gly Ile
        355                 360                 365 gct aga tac att gca gtg aag ctt ttc aat tat aat tac agc tta act   1152
Ala Arg Tyr Ile Ala Val Lys Leu Phe Asn Tyr Asn Tyr Ser Leu Thr
    370                 375                 380 gag tat ggg atg cac tgg aat ttt ttt ctt act ctc ttt ttt act ctc   1200
Glu Tyr Gly Met His Trp Asn Phe Phe Leu Thr Leu Phe Phe Thr Leu
385                 390                 395                 400 cta act tgt aac gcc cta ctc tgc ttg ata aga ggg gtt aaa cgc acc   1248
```

-continued

| | | |
|---|---|---|
| Leu Thr Cys Asn Ala Leu Leu Cys Leu Ile Arg Gly Val Lys Arg Thr<br>                       405                       410                  415 | |

```
ttt cac ctg agc tgc gtc ctc atc tgt ttg tat gaa att ata att tgg     1296
Phe His Leu Ser Cys Val Leu Ile Cys Leu Tyr Glu Ile Ile Ile Trp
            420                 425                 430 cgc ctg gac att acg agt tat tta gtg gtt gac gag gca gaa cgg agc     1344
Arg Leu Asp Ile Thr Ser Tyr Leu Val Val Asp Glu Ala Glu Arg Ser
        435                 440                 445 ggc ttt ttt tcg cag aac aga gag ggc ctt atg aac gtc atc ggg tcc     1392
Gly Phe Phe Ser Gln Asn Arg Glu Gly Leu Met Asn Val Ile Gly Ser
    450                 455                 460 gtc aat ttg tac ctc ttt tcg ttt tcg cta tgg aat ggc tat gtg ttt     1440
Val Asn Leu Tyr Leu Phe Ser Phe Ser Leu Trp Asn Gly Tyr Val Phe
465                 470                 475                 480 ccg gat gag ggg cag cag tgg gag cga gga aag gcg gcg cga aga ccg     1488
Pro Asp Glu Gly Gln Gln Trp Glu Arg Gly Lys Ala Ala Arg Arg Pro
                485                 490                 495 gat gag gcg gcg cga acg ccg ggg gag gga cat ggc cag cgc tcc cct     1536
Asp Glu Ala Ala Arg Thr Pro Gly Glu Gly His Gly Gln Arg Ser Pro
            500                 505                 510 gtc cgc ctc acc ctg aag ttg ctt gcc ctg tcc ctc ctc ttc cac ctg     1584
Val Arg Leu Thr Leu Lys Leu Leu Ala Leu Ser Leu Leu Phe His Leu
        515                 520                 525 ctg cac ctg ctg ttg aat tac tac cga aat tac agt gtg cgc atc ctt     1632
Leu His Leu Leu Leu Asn Tyr Tyr Arg Asn Tyr Ser Val Arg Ile Leu
    530                 535                 540 tgc aac gcg aac tac ata tgt gtt gtc tcc tcc gtg agt ctc ttc gcg     1680
Cys Asn Ala Asn Tyr Ile Cys Val Val Ser Ser Val Ser Leu Phe Ala
545                 550                 555                 560 gct gcc ctg agc tac ctc gta gag aag gta ctc ctc cgc gag aag acc     1728
Ala Ala Leu Ser Tyr Leu Val Glu Lys Val Leu Leu Arg Glu Lys Thr
                565                 570                 575 acc acc atc cca gtt ttg caa caa atg aac cgg cac tcc ctg gca gtg     1776
Thr Thr Ile Pro Val Leu Gln Gln Met Asn Arg His Ser Leu Ala Val
            580                 585                 590 ttc ctc ttt tgc aac gta aca atg ggc act ttc aac ctc ctc ttt cag     1824
Phe Leu Phe Cys Asn Val Thr Met Gly Thr Phe Asn Leu Leu Phe Gln
        595                 600                 605 tct ctc ttg ttt ccc cta ttt ttt gcg tgc ctc gtt ttg gcg gcg tac     1872
Ser Leu Leu Phe Pro Leu Phe Phe Ala Cys Leu Val Leu Ala Ala Tyr
    610                 615                 620 tcc tat ggc atg ttg cgc ttc gcc tcc ctg ttg ccc ggc ccc gcg cag     1920
Ser Tyr Gly Met Leu Arg Phe Ala Ser Leu Leu Pro Gly Pro Ala Gln
625                 630                 635                 640 ggg gag aag gga gag aag cgg gag aag cag caa taa                    1956
Gly Glu Lys Gly Glu Lys Arg Glu Lys Gln Gln  *
                645                 650
```

<210> SEQ ID NO 4
<211> LENGTH: 651
<212> TYPE: PRT
<213> ORGANISM: Plasmodium vivax

<400> SEQUENCE: 4

```
Met Ala His Leu Asn Leu Leu Val Tyr Leu Ile Met Cys Pro Phe Asn
 1               5                  10                  15

Val Arg His Met Leu Asp Ala Pro Ser Phe Pro Phe Arg Leu Gly Ser
                20                  25                  30

Lys Ala Ala Ser Gly Glu Thr Phe Thr Tyr Gly Ala Thr Ala Arg Glu
            35                  40                  45
```

```
Asn Leu Gly Ser Tyr Ser Pro Ala His Asp Glu Leu Tyr Met Leu Glu
 50                  55                  60

Leu Ala Lys Met Tyr Tyr Lys Ile Val Leu Thr Tyr Lys Lys Asp Val
 65                  70                  75                  80

Arg Lys Gly Gln Glu Glu Ser Tyr Asn Leu Val Val Gly Ser Phe Gly
                 85                  90                  95

Lys Glu Ala Lys Gly Glu Val Ser Leu Gln Arg Val Leu Ile Thr Asn
                100                 105                 110

Asp Ala Val Tyr Leu Ser Tyr Gln Asp Val Gln Asn Glu Arg Gly Ile
            115                 120                 125

Gln Val Lys Ile Lys Arg Gly Glu Ile Ser Ser Tyr Leu Asp Leu Leu
130                 135                 140

Ser Trp Asp Ser Cys Leu Tyr Lys Leu Asn Ser Asp Tyr Asn Leu
145                 150                 155                 160

Met Lys Ser Ala Ser Asp His Ser Lys Pro Met Val Val Ser Thr Tyr
                165                 170                 175

His Ile Tyr Met Leu Leu Leu Val Phe Ser Leu Cys Thr Tyr Val Glu
            180                 185                 190

Lys Ser Leu Leu Leu Glu Phe Pro Ala Leu Lys Lys Cys Gln Val Phe
                195                 200                 205

Leu Thr Leu Cys Leu Val Tyr Cys Pro Ile Ile Ser Tyr Leu Phe Phe
            210                 215                 220

Phe Tyr Ser His Val Ser Leu Leu Gly Val Leu Leu Val Tyr Val Phe
225                 230                 235                 240

Phe Cys Gly Leu Phe Arg Gly Val Ser Cys Arg Arg Gly Gly Gln His
                245                 250                 255

Met Gly Glu Gln Thr Gly Gln His Thr Gly Asp Trp His Thr Ile Arg
                260                 265                 270

Gly Asn Pro Gln Gly Asp Asp Thr Gln Glu Glu Arg Arg Lys Cys Leu
            275                 280                 285

Val His Met Arg Leu Ala Asn Leu Cys Ile Thr Tyr Ile Cys Ile Phe
290                 295                 300

Ala Val Asp Phe Tyr Phe Phe Pro Arg Gln Phe Ser Lys Ser Phe Phe
305                 310                 315                 320

Phe Gly Asn Thr Leu Met Asp Leu Gly Val Gly Gly Cys Ile Thr Ser
                325                 330                 335

Ser Ala Tyr Ser Leu Asn Ser Lys Lys Leu His Ser Ala Asn Arg Lys
            340                 345                 350

Gly His Leu Ile Asp Trp Lys His Phe Ile Leu Phe Phe Leu Gly Ile
                355                 360                 365

Ala Arg Tyr Ile Ala Val Lys Leu Phe Asn Tyr Asn Tyr Ser Leu Thr
370                 375                 380

Glu Tyr Gly Met His Trp Asn Phe Phe Leu Thr Leu Phe Phe Thr Leu
385                 390                 395                 400

Leu Thr Cys Asn Ala Leu Leu Cys Leu Ile Arg Gly Val Lys Arg Thr
                405                 410                 415

Phe His Leu Ser Cys Val Leu Ile Cys Leu Tyr Glu Ile Ile Ile Trp
            420                 425                 430

Arg Leu Asp Ile Thr Ser Tyr Leu Val Val Asp Glu Ala Glu Arg Ser
                435                 440                 445

Gly Phe Phe Ser Gln Asn Arg Glu Gly Leu Met Asn Val Ile Gly Ser
            450                 455                 460

Val Asn Leu Tyr Leu Phe Ser Phe Ser Leu Trp Asn Gly Tyr Val Phe
465                 470                 475                 480
```

```
Pro Asp Glu Gly Gln Gln Trp Glu Arg Gly Lys Ala Ala Arg Arg Pro
                485                 490                 495
Asp Glu Ala Ala Arg Thr Pro Gly Glu Gly His Gly Gln Arg Ser Pro
            500                 505                 510
Val Arg Leu Thr Leu Lys Leu Leu Ala Leu Ser Leu Leu Phe His Leu
                515                 520                 525
Leu His Leu Leu Leu Asn Tyr Tyr Arg Asn Tyr Ser Val Arg Ile Leu
            530                 535                 540
Cys Asn Ala Asn Tyr Ile Cys Val Val Ser Ser Val Ser Leu Phe Ala
545                 550                 555                 560
Ala Ala Leu Ser Tyr Leu Val Glu Lys Val Leu Leu Arg Glu Lys Thr
                565                 570                 575
Thr Thr Ile Pro Val Leu Gln Gln Met Asn Arg His Ser Leu Ala Val
            580                 585                 590
Phe Leu Phe Cys Asn Val Thr Met Gly Thr Phe Asn Leu Leu Phe Gln
                595                 600                 605
Ser Leu Leu Phe Pro Leu Phe Phe Ala Cys Leu Val Leu Ala Ala Tyr
            610                 615                 620
Ser Tyr Gly Met Leu Arg Phe Ala Ser Leu Leu Pro Gly Pro Ala Gln
625                 630                 635                 640
Gly Glu Lys Gly Glu Lys Arg Glu Lys Gln Gln
                645                 650
```

<210> SEQ ID NO 5
<211> LENGTH: 2625
<212> TYPE: DNA
<213> ORGANISM: Artificial Sequence
<220> FEATURE:
<223> OTHER INFORMATION: Artificially synthesized sequence

<400> SEQUENCE: 5

```
atgagtaaca tgaacatcct ggcctacctg ctgatctgtc cattcaacct gatctacatc      60
ttcgacctgc ctagctacat ccctgagcta acaagaaagc tggagaacga cgaagtcttc    120
atctacggta aggagatccg taagaacgaa tccgcatact ctctacacta cgagaagtac    180
ctatacgaat tgtcacgaag atactacgag atcatcctga agtacaacaa ggagttggga    240
gtcaaccaag agaaggaata caacctgatt atctccagag agatcgataa agaagaagaag  300
aagcagaaga atagtaccca gggtgaatac aataacgacg atgataacaa ttggaagttg    360
ttccagattt acgagaagga agaacctagg agctatgaat tgatcagggt agagatatac    420
aagaaggaca ttctgttgat ctacaagaat gagaagacga agtcctctat caagttcatt    480
atcaagaagc gtaaggatat caagaattac ttctccttgt gttaccagaa ctgtatcaat    540
aagctggaca gaatgattaa cacatcttg aagtctacca tcaacaattc caaggaaaac   600
attatcaact ctgcatacat ttacatgtac attatcttct tcttcctgtg catatacgtc    660
gagaagaacc tgttcttgta cttcccaata ttgcttcaga agtatgagat ctcactacg     720
ttgttcatcc tcttcatccc attgatccta ttcgtattct ctatttctac ttcacgatt    780
atcaagctga tttgctcatg cttagtccta tacgtgactt tccagttgat ctactatacg    840
cagggaatgc ctatttacat ggaacatagt attctcaagc acaaggagaa ggaagagatt    900
tgcgatgaga aggaggaaat ctgtgatgaa aaggaagaga tttgcgatga aaggaagag     960
atttgcgatg agaaggaaga gatttgtgat gagaaggaag aaatctgcga tgagaaagaa   1020
gaaatccttg ataagaagaa gaagatccac gagaagaaga agaagatcca tgataagaaa   1080
```

```
gaggaaatcg atgagaagaa gaagaagatt catgacaaaa aggacgaaag tcatgataag    1140
aacgaggaca ttacgtatcc agtccagtac aatatcgaga atgacctatg gtattcatcc    1200
aagaacgtgg acatcaagat gtattcatcc agcaacaagg gtgaagaata cattatccag    1260
aacacgttga acatttccg attgatgaac atgtgtatga cgtacatttg tatcttcgct    1320
gttgacttct acttcttccc taaccatttc tgcaagtcct actattacgg aaatacgttg    1380
atggacattg gaatcggtgc atccatttct tccagtgcat actcgcagga gatcaagaag    1440
ttcacgtaca ttaaggagaa gaaacgaatt atcgagttga acatatcgt gttattcatt    1500 ctgggaatta gcagatttat cggtatctac ctattcaact ataactacaa catttctgag    1560
tatggaatcc attggaactt ctttcttacg ctatgtacaa cctttctgat tagcaacatt    1620
tgtttcatcc tcctcaagag gattcgttat atcttcctat tcagtattat ctcgatcatc    1680
ttattcgaaa tcgctatttta ctacttcgat ctacataatt acatcctcct gaagaatgac    1740
cgtttaaact tcttctcttc taacaaggag ggtctattca acattatcgg ttccgtgaac    1800
ctttatttgt tcagtttctc actcttcaag taccttacga agcagcgtac gtatatcacg    1860
acgtccaata tccctaagaa caagaaagat atgaataact caatgtattc gaagaatgga    1920
aaccatacta attcgaatat caacaaccgt aaccataaga tcgtcatccg taataaccac    1980
attaacaagt atgagcagga caacacgaac aagtacatca acaagcaaat caataacaac    2040
aagaacaaat tggatgagga agagaagctg aagaaactca agaagcttaa gaataagaag    2100
aagaacctca agaagaaaat caagtactat ctattgtacc ttcagtatat catcaacatc    2160
tacaaggagg aatactatac gatctactat aacatcaagc taatcatttc gtcgtttata    2220
ttctacctcc ttcacataat ccttaatctg tacaagaact actctgtgcg tattctgtgt    2280
aatgcaaact acatcttcct gattacgagt ctgggtctgt tctcctgtgc attatccttc    2340
tccctggagg acatcctact ccgttataag aaatacaaga tcaatatcga tattactgtg    2400
ctagataaga ttaacaagaa caccttaatc gtgttcctgt ttagtaatat cctagtggga    2460
atgttcaaca tcctgttcca aactttgctc ctaccactga tattcgttat ccctattcta    2520
gtattctaca gcttcttgat cctgctgttc accaagtgtt tgccaccttc tatccgacat    2580
cctaagaaga agacgcatca cgaagagaag cagaagaaag agtga               2625
```

<210> SEQ ID NO 6
<211> LENGTH: 2010
<212> TYPE: DNA
<213> ORGANISM: Plasmodium falciparum

<400> SEQUENCE: 6

```
atgtgcacta caaaaaatga agacaataat aaagtgaatt atctgtatct catttattat     60
aataatatac ctatatttaa aaaaaaagt ggaaatgaac aaaacataag tgcgctattt    120
attttatatg atgtaaaaaa gtatgtgtat aatatggttc atgatcacgt aaatacatta    180
gtcctagaag cttttagaag agaagacata ataaaaaaaa taaagtaaa agaaaaacaa    240 aataataatg ataaaaataa agaaagtaat attgaaaaag ataaaaatga acaaaccaaa    300
tttacagata tatatgatac aaatagtaag agtgacaaag atatacaaaa gaataatatg    360
aacgatggtg atagtaataa taaaaatagt agttttattta ttgatccttt tgaaagtgat    420
tcatatgaaa agaataattt tagtaatgaa aaatgtgctt tccaaaatgt cgataaatca    480 aaaaagata agaacatat atattctgaa aatattactc ctagtagtag taataataat    540
aatgataata ataaagaaaa tgattgtgat aaggaacaat tagataaata taataaagat    600
```

-continued

```
aaagaaaata aattaaaatt aaatgataag gatgaatata tttctttcaa ttttattgaa     660
gataaattaa ccgaatcatt tcatatgaat caaataattc atttaattaa taaaaaatgt     720
gtatttacca aatgcctaga aaattataaa aatagatatt ttgtactgaa aaaagaagag     780
atttaaaaa aaaaaaaaaa gcaaaaaaaa atgtctatat tttcatatat tgtatcaatc     840
atattatttt ttacatatat catatcactt ataaatagtt gtttatatta tataatatgt     900
acaccaaaat tgttcagtga atatatattt tcaaaaaaat gtgatggata tctgcagaat     960
tcggcttacc ctaaatttat atttccttct gaatggcata atatattccg cagcttcatg    1020
aaaaataaac aaaacccatc tgaatattat aaatatagag aaatcttatt aattcgtatt    1080
atcaatttaa taatcgatat tttcttggga tttctgatat ttttactact ttattttaac    1140
gtaataaacc tacattatat atcagagaag gctcaaatat tttatggaac cagtacttta    1200
acttctatct tgggtacctt gttacagaat ccattaggat ttaaattaaa taataatttt    1260
acgtctttca ttggtagcat ccttgtttcg atattagaca aatgggattt atttacaaat    1320
accatccctg tgaataatag tacagttttg aattttgttg gatatacatc actgctgggt    1380
ttttcttttt ttttgtcttt tgttattgat tatttgagat tcgtaacagc acatgttacc    1440
attatttatt tattttttgaa aaaaatatgt acccttttc ataaaaatat gtattcctta    1500
tacctattat tcaatgggaa aaaatggaac atactaaaac taagagttga tacaaattac    1560
tactcaaatg aagaagtact tttaggaacc atattattta ccattttaat ttttttgtac    1620
cctaccattt ttgttcttgt tttggttttt ggtcttatat atcttataat aaatagaatt    1680
ataccttt tgtgtgttat ggagaaaata attttgtaca cccctttcta tattttcttt    1740
attcaaccga attgtaataa atatattagt aagggtttca agtttacaaa atatgaagtt    1800
ggggaacatg aactgttaaa aaggtatccg actaacagct acttgttgct agaaaagatt    1860
cattttttat ttttttgataa aataaaattg tttataaata ttttccttta ttttaaaaac    1920
ctcgagtcaa tgtcatcata ttcatatata tttatttctt tttgttttttg tcttttaaaa    1980
aaaaaatata tatatatata tataatataa                                      2010
```

<210> SEQ ID NO 7
<211> LENGTH: 669
<212> TYPE: PRT
<213> ORGANISM: Plasmodium falciparum

<400> SEQUENCE: 7

```
Met Cys Thr Thr Lys Asn Glu Asp Asn Asn Lys Val Asn Tyr Leu Tyr
 1               5                  10                  15

Leu Ile Tyr Tyr Asn Asn Ile Pro Ile Phe Lys Lys Lys Ser Gly Asn
            20                  25                  30

Glu Gln Asn Ile Ser Ala Leu Phe Ile Leu Tyr Asp Val Lys Lys Tyr
        35                  40                  45

Val Tyr Asn Met Val His Asp His Val Asn Thr Leu Val Leu Glu Ala
    50                  55                  60

Phe Arg Arg Glu Asp Ile Ile Lys Lys Ile Lys Val Lys Glu Lys Gln
65                  70                  75                  80

Asn Asn Asn Asp Lys Asn Lys Glu Ser Asn Ile Glu Lys Asp Lys Asn
                85                  90                  95

Glu Gln Thr Lys Phe Thr Asp Ile Tyr Asp Thr Asn Ser Lys Ser Asp
            100                 105                 110

Lys Asp Ile Gln Lys Asn Asn Met Asn Asp Gly Asp Ser Asn Asn Lys
        115                 120                 125
```

-continued

```
Asn Ser Ser Leu Phe Ile Asp Pro Phe Glu Ser Asp Ser Tyr Glu Lys
            130                 135                 140

Asn Asn Phe Ser Asn Glu Lys Cys Ala Phe Gln Asn Val Asp Lys Ser
145                 150                 155                 160

Lys Lys Asp Lys Glu His Ile Tyr Ser Glu Asn Ile Thr Pro Ser Ser
                165                 170                 175

Ser Asn Asn Asn Asp Asn Asn Lys Glu Asn Asp Cys Asp Lys Glu
            180                 185                 190

Gln Leu Asp Lys Tyr Asn Lys Asp Lys Glu Asn Lys Leu Lys Leu Asn
                195                 200                 205

Asp Lys Asp Glu Tyr Ile Ser Phe Asn Phe Ile Glu Asp Lys Leu Thr
210                 215                 220

Glu Ser Phe His Met Asn Gln Ile Ile His Leu Ile Asn Lys Lys Cys
225                 230                 235                 240

Val Phe Thr Lys Cys Leu Glu Asn Tyr Lys Asn Arg Tyr Phe Val Leu
                245                 250                 255

Lys Lys Glu Glu Ile Leu Lys Lys Lys Lys Gln Lys Lys Met Ser
            260                 265                 270

Ile Phe Ser Tyr Ile Val Ser Ile Ile Leu Phe Phe Thr Tyr Ile Ile
                275                 280                 285

Ser Leu Ile Asn Ser Cys Leu Tyr Tyr Ile Ile Cys Thr Pro Lys Leu
            290                 295                 300

Phe Ser Glu Tyr Ile Phe Ser Lys Lys Cys Asp Gly Tyr Leu Gln Asn
305                 310                 315                 320

Ser Ala Tyr Pro Lys Phe Ile Phe Pro Ser Glu Trp His Asn Ile Phe
                325                 330                 335

Arg Ser Phe Met Lys Asn Lys Gln Asn Pro Ser Glu Tyr Tyr Lys Tyr
                340                 345                 350

Arg Glu Ile Leu Leu Ile Arg Ile Ile Asn Leu Ile Ile Asp Ile Phe
                355                 360                 365

Leu Gly Phe Leu Ile Phe Leu Leu Leu Tyr Phe Asn Val Ile Asn Leu
            370                 375                 380

His Tyr Ile Ser Glu Lys Ala Gln Ile Phe Tyr Gly Thr Ser Thr Leu
385                 390                 395                 400

Thr Ser Ile Leu Gly Thr Leu Leu Gln Asn Pro Leu Gly Phe Lys Leu
                405                 410                 415

Asn Asn Asn Phe Thr Ser Phe Ile Gly Ser Ile Leu Val Ser Ile Leu
            420                 425                 430

Asp Lys Trp Asp Leu Phe Thr Asn Thr Ile Pro Val Asn Asn Ser Thr
            435                 440                 445

Val Leu Asn Phe Val Gly Tyr Thr Ser Leu Leu Gly Phe Ser Phe Phe
450                 455                 460

Leu Ser Phe Val Ile Asp Tyr Leu Arg Phe Val Thr Ala His Val Thr
465                 470                 475                 480

Ile Ile Tyr Leu Phe Leu Lys Lys Ile Cys Thr Leu Phe His Lys Asn
                485                 490                 495

Met Tyr Ser Leu Tyr Leu Leu Phe Asn Gly Lys Lys Trp Asn Ile Leu
            500                 505                 510

Lys Leu Arg Val Asp Thr Asn Tyr Tyr Ser Asn Glu Val Leu Leu
            515                 520                 525

Gly Thr Ile Leu Phe Thr Ile Leu Ile Phe Leu Tyr Pro Thr Ile Phe
            530                 535                 540

Val Leu Val Leu Val Phe Gly Leu Ile Tyr Leu Ile Ile Asn Arg Ile
545                 550                 555                 560
```

Ile Tyr Leu Leu Cys Val Met Glu Lys Ile Ile Leu Tyr Thr Pro Phe
            565                 570                 575

Tyr Ile Phe Phe Ile Gln Pro Asn Cys Asn Lys Tyr Ile Ser Lys Gly
            580                 585                 590

Phe Lys Phe Thr Lys Tyr Glu Val Gly Glu His Glu Leu Leu Lys Arg
            595                 600                 605

Tyr Pro Thr Asn Ser Tyr Leu Leu Leu Glu Lys Ile His Phe Leu Phe
    610                 615                 620

Phe Asp Lys Ile Lys Leu Phe Ile Asn Ile Phe Leu Tyr Phe Lys Asn
625                 630                 635                 640

Leu Glu Ser Met Ser Ser Tyr Ser Tyr Ile Phe Ile Ser Phe Cys Phe
            645                 650                 655

Cys Leu Leu Lys Lys Lys Tyr Ile Tyr Ile Tyr Ile Ile
            660                 665

<210> SEQ ID NO 8
<211> LENGTH: 1482
<212> TYPE: DNA
<213> ORGANISM: Plasmodium falciparum

<400> SEQUENCE: 8

| | | | | | |
|---|---|---|---|---|---|
| atggggataa | aaattataat | ttatatattt | tttctatcgt | gggcgaaatg | ggtgtgtggg | 60 |
| tctgttaatt | ttaccggggtt | tgataacaaa | aatatgatag | gtaagcacgt | ggaactagaa | 120 | atgggataa aaattataat ttatatattt tttctatcgt gggcgaaatg ggtgtgtggg    60 tctgttaatt ttaccggggtt tgataacaaa atatgatag gtaagcacgt ggaactagaa   120 gggaggtata aaaaggaata tatagatagg ttttttttag aagaattaag aaaacacaat   180 tatatgaata acaatgttat attattaagt acatcaagac attattttaa ttatagacat   240 accactaatt tattgattgc atataaatat cttaaatatt tcggtgatac tatggataag   300 aatatttat taatgattcc atttgatcaa gcttgtgatt gtaggaatat aagagaaggt   360 caaatatttc gagaatatga attatttcct agtagtcata taaagaaac aaaaatagaa   420 aatataaatt tatatgagaa tttaaatatt gattataaaa ataataatgt acgtgatgaa   480 caaattagaa gagtacttag acatagatat gatgctttta cacctaaaaa aaatagatta   540 tataataatg gaaataatga gaaaaattta tttctttata tgaccggaca tggtggtgtg   600 aatttttaa aaattcaaga atttaatatt attagttctt ctgaatttaa tatatatata   660 caagaattac ttatcaaaaa ttttttataaa tatatattcg taattattga tacgtgtcaa   720 ggatatagtt tttatgatga tattctaaat tttgtatata aaaaaaaaat taataatatc   780 ttctttttat catcttctaa aagaaatgaa aatagttata gtttatttc cagtagttat   840 ttaagcgttt caacggtcga cagatttaca taccatttt ttaattatct tcaacaaata   900 cataaaatat atgaaaaaga accatctaaa aatataaaag ccttttcatt atataacatt   960 ttaaattatt taaaaacaca acatattatg tcagaaccta ctacaaataa ttctaaattt  1020 aattcgtcca ttttttaca tgataaaaat attcttttct tcaattctaa tttgttaatt  1080 atacataaag atgatgtttc tataatatat caagataaac aaacacacaa tcacaaatat  1140 atatgtttgg ataatctatc taaatgtggt catataaaaa ataatgtaca taaaaaaatg  1200 caaactctat atgaacaaac gttatattat aataataatc aacagaattt cttttctaat  1260 catatgtcta attttacaga ttattttttt acacatgata tataaatat atataatata  1320 tataatgtat ataatatata aatgtatat aatatatata atgtatatga tatatataat  1380 gtatattctt tcttatatt attgctctct ttattttta ttatgtgttc tcttcttaca  1440 tattatattg tttttttac agaaaaggct aaaatgacat aa                       1482

<210> SEQ ID NO 9
<211> LENGTH: 493
<212> TYPE: PRT
<213> ORGANISM: Plasmodium falciparum

<400> SEQUENCE: 9

```
Met Gly Ile Lys Ile Ile Tyr Ile Phe Phe Leu Ser Trp Ala Lys
  1               5                  10                  15

Trp Val Cys Gly Ser Val Asn Phe Thr Gly Phe Asp Asn Lys Asn Met
                 20                  25                  30

Ile Gly Lys His Val Glu Leu Glu Gly Arg Tyr Lys Lys Glu Tyr Ile
             35                  40                  45

Asp Arg Phe Phe Leu Glu Glu Leu Arg Lys His Asn Tyr Met Asn Asn
         50                  55                  60

Asn Val Ile Leu Leu Ser Thr Ser Arg His Tyr Phe Asn Tyr Arg His
 65                  70                  75                  80

Thr Thr Asn Leu Leu Ile Ala Tyr Lys Tyr Leu Lys Tyr Phe Gly Asp
                 85                  90                  95

Thr Met Asp Lys Asn Ile Leu Leu Met Ile Pro Phe Asp Gln Ala Cys
            100                 105                 110

Asp Cys Arg Asn Ile Arg Glu Gly Gln Ile Phe Arg Glu Tyr Glu Leu
        115                 120                 125

Phe Pro Ser Ser His Asn Lys Glu Thr Lys Ile Glu Asn Ile Asn Leu
    130                 135                 140

Tyr Glu Asn Leu Asn Ile Asp Tyr Lys Asn Asn Asn Val Arg Asp Glu
145                 150                 155                 160

Gln Ile Arg Arg Val Leu Arg His Arg Tyr Asp Ala Phe Thr Pro Lys
                165                 170                 175

Lys Asn Arg Leu Tyr Asn Asn Gly Asn Asn Glu Lys Asn Leu Phe Leu
            180                 185                 190

Tyr Met Thr Gly His Gly Gly Val Asn Phe Leu Lys Ile Gln Glu Phe
        195                 200                 205

Asn Ile Ile Ser Ser Ser Glu Phe Asn Ile Tyr Ile Gln Glu Leu Leu
    210                 215                 220

Ile Lys Asn Phe Tyr Lys Tyr Ile Phe Val Ile Ile Asp Thr Cys Gln
225                 230                 235                 240

Gly Tyr Ser Phe Tyr Asp Asp Ile Leu Asn Phe Val Tyr Lys Lys Lys
                245                 250                 255

Ile Asn Asn Ile Phe Phe Leu Ser Ser Ser Lys Arg Asn Glu Asn Ser
            260                 265                 270

Tyr Ser Leu Phe Ser Ser Ser Tyr Leu Ser Val Ser Thr Val Asp Arg
        275                 280                 285

Phe Thr Tyr His Phe Phe Asn Tyr Leu Gln Gln Ile His Lys Ile Tyr
    290                 295                 300

Glu Lys Glu Pro Ser Lys Asn Ile Lys Ala Phe Ser Leu Tyr Asn Ile
305                 310                 315                 320

Leu Asn Tyr Leu Lys Thr Gln His Ile Met Ser Glu Pro Thr Thr Asn
                325                 330                 335

Asn Ser Lys Phe Asn Ser Ser Ile Phe Leu His Asp Lys Asn Ile Leu
            340                 345                 350

Phe Phe Asn Ser Asn Leu Leu Ile Ile His Lys Asp Val Ser Ile
        355                 360                 365

Ile Tyr Gln Asp Lys Gln Thr His Asn His Lys Tyr Ile Cys Leu Asp
    370                 375                 380
```

-continued

```
Asn Leu Ser Lys Cys Gly His Ile Lys Asn Asn Val His Lys Lys Met
385                 390                 395                 400

Gln Thr Leu Tyr Glu Gln Thr Leu Tyr Tyr Asn Asn Asn Gln Gln Asn
            405                 410                 415

Phe Phe Ser Asn His Met Ser Asn Phe Thr Asp Tyr Phe Phe Thr His
        420                 425                 430

Asp Ile Tyr Asn Ile Tyr Asn Ile Tyr Asn Val Tyr Asn Ile Tyr Asn
    435                 440                 445

Val Tyr Asn Ile Tyr Asn Val Tyr Asp Ile Tyr Asn Val Tyr Ser Phe
450                 455                 460

Leu Ile Leu Leu Leu Ser Leu Phe Phe Ile Met Cys Ser Leu Leu Thr
465                 470                 475                 480

Tyr Tyr Ile Val Phe Phe Thr Glu Lys Ala Lys Met Thr
                485                 490
```

<210> SEQ ID NO 10
<211> LENGTH: 1494
<212> TYPE: DNA
<213> ORGANISM: Plasmodium falciparum

<400> SEQUENCE: 10

| | | |
|---|---|---|
| atggaaagtg cagttagcga atgcaatata tacaaaaagg aaaagataa aaatataatt | 60 |
| tacaaacaag aaagaaaatg ttgtatttgc atggtgagtg attttttta tccaaatttg | 120 |
| ggaggaatag aaactcacat ttttgaattg tctaagaatt tgataaaaaa gggtttcaag | 180 |
| gttatagttg taacaaattt taataataat aggcatggta agatggat gggtaatggt | 240 |
| attaaggttt attatttgcc cttccagcct tttttagatg tagtgagttt tccaaatatt | 300 |
| atagggactt taccactatg tagaaatata ttatataggg aaaaagtcga catagtacat | 360 |
| ggtcaccagg ctacgtcagc attagctcat caattcattc ttcatgccaa aaccttagga | 420 |
| ataaaaacta tttatacaga tcactcatta tacagttttt cagacaaagg atgcatacat | 480 |
| gtaaacaaat tattgaaata ttgtataaac gatgttgatc attctatatg tgtttcccat | 540 |
| acgaatagag aaaatttagt tttgagaaca gaaagtaatc catataaaac gtcagttata | 600 |
| ggaaatgccc ttgatactac aaaatttgtt ccttgtatta gtaaaagacc aaagtttcca | 660 |
| agaataaata ttattgttat aagtaggtta acatatagaa aaggtataga tttgatagtt | 720 |
| aaggtaatac cattagtatg tcaaaaatat ccattcataa aatttattat aggggagaa | 780 |
| ggtcctaaaa gattgttatt agaagaaatg agagaaaagt atcacttaca taattctgtt | 840 |
| gtattattag gaaaagtaaa acaagaaaat gtaaaaaata ttttacaaac tggtcatata | 900 |
| ttcttaaata catctttaac agaagctttt tgtatagcca taattgaagc agctagttgt | 960 |
| ggtttgcttg tcatatctac ggatgtaggt ggaatatctg aagttttacc acacgatatg | 1020 |
| atgattttag ctaaaccaaa tcatatcgaa ttatgtaaag cagtcgataa agcattaaaa | 1080 |
| attgtacaaa aggtggactc aaattattc cacgaaaggg taaacatgag tttattaaca | 1140 |
| tatgtaaata tatatatata tatatatata tatatatata taatatatat gaataatttt | 1200 |
| atttataatc taaccaaaat gtactcttgg gaaaaagtag cggaaaagac ggtaaaatca | 1260 |
| cataatacat atattatgaa tattgaaaag gtgtatatga acgtattaaa ttatgcaaat | 1320 |
| ccaagcttgt ttaatagaat aagaaaaata tacgaaatta atacacctat tcatgtttcc | 1380 |
| tttttttttt tttagacaa aatattgaag aggtcgttag ctttcctcat ttttatgatg | 1440 |
| acgaaaataa aaatgaaaaa taagagtttt aaaatgtcga tatataccac ataa | 1494 |

```
<210> SEQ ID NO 11
<211> LENGTH: 497
<212> TYPE: PRT
<213> ORGANISM: Plasmodium falciparum

<400> SEQUENCE: 11

Met Glu Ser Ala Val Ser Glu Cys Asn Ile Tyr Lys Lys Glu Lys Asp
 1               5                  10                  15

Lys Asn Ile Ile Tyr Lys Gln Glu Arg Lys Cys Cys Ile Cys Met Val
            20                  25                  30

Ser Asp Phe Phe Tyr Pro Asn Leu Gly Gly Ile Glu Thr His Ile Phe
        35                  40                  45

Glu Leu Ser Lys Asn Leu Ile Lys Lys Gly Phe Lys Val Ile Val Val
    50                  55                  60

Thr Asn Phe Asn Asn Asn Arg His Gly Ile Arg Trp Met Gly Asn Gly
65                  70                  75                  80

Ile Lys Val Tyr Tyr Leu Pro Phe Gln Pro Phe Leu Asp Val Val Ser
                85                  90                  95

Phe Pro Asn Ile Ile Gly Thr Leu Pro Leu Cys Arg Asn Ile Leu Tyr
            100                 105                 110

Arg Glu Lys Val Asp Ile Val His Gly His Gln Ala Thr Ser Ala Leu
        115                 120                 125

Ala His Gln Phe Ile Leu His Ala Lys Thr Leu Gly Ile Lys Thr Ile
    130                 135                 140

Tyr Thr Asp His Ser Leu Tyr Ser Phe Ser Lys Gly Cys Ile His
145                 150                 155                 160

Val Asn Lys Leu Leu Lys Tyr Cys Ile Asn Asp Val Asp His Ser Ile
                165                 170                 175

Cys Val Ser His Thr Asn Arg Glu Asn Leu Val Leu Arg Thr Glu Ser
            180                 185                 190

Asn Pro Tyr Lys Thr Ser Val Ile Gly Asn Ala Leu Asp Thr Thr Lys
        195                 200                 205

Phe Val Pro Cys Ile Ser Lys Arg Pro Lys Phe Pro Arg Ile Asn Ile
    210                 215                 220

Ile Val Ile Ser Arg Leu Thr Tyr Arg Lys Gly Ile Asp Leu Ile Val
225                 230                 235                 240

Lys Val Ile Pro Leu Val Cys Gln Lys Tyr Pro Phe Ile Lys Phe Ile
                245                 250                 255

Ile Gly Gly Glu Gly Pro Lys Arg Leu Leu Glu Glu Met Arg Glu
            260                 265                 270

Lys Tyr His Leu His Asn Ser Val Val Leu Leu Gly Lys Val Lys Gln
        275                 280                 285

Glu Asn Val Lys Asn Ile Leu Gln Thr Gly His Ile Phe Leu Asn Thr
    290                 295                 300

Ser Leu Thr Glu Ala Phe Cys Ile Ala Ile Glu Ala Ala Ser Cys
305                 310                 315                 320

Gly Leu Leu Val Ile Ser Thr Asp Val Gly Gly Ile Ser Glu Val Leu
                325                 330                 335

Pro His Asp Met Met Ile Leu Ala Lys Pro Asn His Ile Glu Leu Cys
            340                 345                 350

Lys Ala Val Asp Lys Ala Leu Lys Ile Val Gln Lys Val Asp Ser Asn
        355                 360                 365

Leu Phe His Glu Arg Val Asn Met Ser Leu Leu Thr Tyr Val Asn Ile
    370                 375                 380

Tyr Ile Tyr Ile Tyr Ile Tyr Ile Tyr Ile Ile Tyr Met Asn Asn Phe
```

```
                385                 390                 395                 400
Ile Tyr Asn Leu Thr Lys Met Tyr Ser Trp Glu Lys Val Ala Glu Lys
                    405                 410                 415

Thr Val Lys Ser His Asn Thr Tyr Ile Met Asn Ile Glu Lys Val Tyr
                420                 425                 430

Met Asn Val Leu Asn Tyr Ala Asn Pro Ser Leu Phe Asn Arg Ile Arg
            435                 440                 445

Lys Ile Tyr Glu Ile Asn Thr Pro Ile His Val Ser Phe Phe Phe
        450                 455                 460

Leu Asp Lys Ile Leu Lys Arg Ser Leu Ala Phe Leu Ile Phe Met Met
465                 470                 475                 480

Thr Lys Ile Lys Met Lys Asn Lys Ser Phe Lys Met Ser Ile Tyr Thr
                485                 490                 495

Thr

<210> SEQ ID NO 12
<211> LENGTH: 2361
<212> TYPE: DNA
<213> ORGANISM: Plasmodium falciparum

<400> SEQUENCE: 12
atgatttaca atgacatttt aacattatgt gcaaataaat taagaggact aattgattca      60
aagatattta tttggttgtt aatattttt agaatattta attgtttatt tgttgtaaca     120
tcattttatc ctgatgaata ttttcaatct gtagaaattg ctcatttttg ggcttatgga     180
tatggacata tgtcatggga atgggaacct tgtgtagcat taagatcagt gataactcct     240
tttatttatt atgtattatt tttatttta aaacttatta acatagatca tcctgttttgt     300 gtattataca ttcctaaatt atgtcatggt atatgtgctg ctttgtgtga tttaggtatt     360
tataaattat tgatatattg gtatgttgaa ttgtataatg acgcatggat aaatgaagat     420
aatataaaac gtaatgagaa agatgaaaat aatggaaata caacaacaa taataataat     480 aacaataata ataacaataa taataataat tattattatc ataataatat attatacaac     540
acaaatgaca ttatttctac aattctatgt tgtcattttt tttgttggtt ttattttat     600 tccatatgta ggacatcctc gcattccttt gaatgcttgt ttaatatatg gggtgtatat     660 ttttatcac aaaattatta ccccttgaaa atcaatcaa acaaaataga aaagatagac     720
ttattattac agaacgatgt aatcatacaa aaggaaaga acatttaaa tgaatggaca     780 aatttaaaag aaagaaggaa tgatcatcat tttgatacat acgaaaataa ttttatatat     840
cataaaggaa cacaaaattg taaacaatat gataaaaata tggttgatca aatgtttgt     900 ggtcaaaata tggttgatca cataattcag aacaggaaca atttgtgtag gacacatttt     960
tattcctcca aatttaacaa atacaagag gcaaaaaatt tattattag tttattcttt    1020 agctccttgt ctgttatatt tcgtccaaac gctttagtat tttggttatc tttatatata    1080
ctatatatta taagaatat atttgaaaaa caaataaaa taattataa agaaatattc    1140 aaaataggta ttacgtacac tttttttttt taactatta ttattataat tgattcttat    1200
tattttgggc acattacatt tcccttttgg aattttttg tttataattt tttaagtgga    1260
aacaataaat attttggagg gcattctttt ttttttact ttgtatgtgt tatccttct    1320 atatatttaa ctttaacacc tttttttgtt tatggttatt acattatata taataatata    1380
ttgaataagg tgaagtataa gacaattaat atatatatgt atatattgaa acgaattgat    1440
tggatagtat atttagttac acacttagaa atcctatctt tatctttcag taagcataag    1500
```

-continued

```
gaacataaaa ttgttatagg atatataccg tttcttacaa tttttgttgg atatgcatta    1560
tatataataa aattacatta taaaaaatat aatggcaaaa atggaaagaa tatatataat    1620
aataataaaa tccaatatgg taatataacc ataaagggaa gaaataaata tatttttta    1680 atttcatctt ctcttttac aaatataagt ttttacttc aattttatg tattcttttt    1740 ttctgcctta tacataacag atcacctgaa catgtagcct cttattttag aaacttagaa    1800
acgaaagatg atcaaaatat ttatatattt ataacaaatt gttatgatat acctttatat    1860
tcgcatatac atagaaaatt caatatagga ttttagact gttctcctta tgacacgagt    1920
aatgatgaag ctaccaaaaa ttggagaaaa cgtatatatg aagataaatt taaggaacaa    1980
ttttttaata tttttcaaga aaaaaaaat aataatcatc atataaatag tacatatgga    2040
gatacaatta ctccatatat aataccagat aaatcatttt attggtttgg tcatcatcat    2100
tttaataaaa aaataattt tcaatatatt tatcaaaaca ttaatttgtc atgtttaaat    2160
tatagatttc atataccttt acaaggacaa ttacctactt atatagttac aacaactatt    2220
gaacttacac atttacaatt atttctgagt acatataatt ataaacttga aacaaagcct    2280 ttttttctt attttatgat aagtgaagca aaaggaatag ttccagtata tcattacata    2340
ttcaagaggg ttccttccta a                                             2361
```

<210> SEQ ID NO 13
<211> LENGTH: 786
<212> TYPE: PRT
<213> ORGANISM: Plasmodium falciparum

<400> SEQUENCE: 13

```
Met Ile Tyr Asn Asp Ile Leu Thr Leu Cys Ala Asn Lys Leu Arg Gly
  1               5                  10                  15

Leu Ile Asp Ser Lys Ile Phe Ile Trp Leu Leu Ile Phe Phe Arg Ile
             20                  25                  30

Phe Asn Cys Leu Phe Val Val Thr Ser Phe Tyr Pro Asp Glu Tyr Phe
         35                  40                  45

Gln Ser Val Glu Ile Ala His Phe Trp Ala Tyr Gly His Met
     50                  55                  60

Ser Trp Glu Trp Glu Pro Cys Val Ala Leu Arg Ser Val Ile Thr Pro
 65                  70                  75                  80

Phe Ile Tyr Tyr Val Leu Phe Leu Phe Leu Lys Leu Ile Asn Ile Asp
                 85                  90                  95

His Pro Val Cys Val Leu Tyr Ile Pro Lys Leu Cys His Gly Ile Cys
            100                 105                 110

Ala Ala Leu Cys Asp Leu Gly Ile Tyr Lys Leu Leu Ile Tyr Trp Tyr
        115                 120                 125

Val Glu Leu Tyr Asn Asp Ala Trp Ile Asn Glu Asp Asn Ile Lys Arg
    130                 135                 140

Asn Glu Lys Asp Glu Asn Asn Gly Asn Asn Asn Asn Asn Asn Asn Asn
145                 150                 155                 160

Asn Asn Asn Asn Asn Asn Asn Asn Asn Tyr Tyr Tyr His Asn Asn
                165                 170                 175

Ile Leu Tyr Asn Thr Asn Asp Ile Ile Ser Thr Ile Leu Cys Cys His
            180                 185                 190

Phe Phe Cys Trp Phe Tyr Phe Tyr Ser Ile Cys Arg Thr Ser Ser His
        195                 200                 205

Ser Phe Glu Cys Leu Phe Asn Ile Trp Gly Val Tyr Phe Leu Ser Gln
    210                 215                 220
```

```
Asn Tyr Tyr Pro Leu Lys Asn Gln Ser Asn Lys Ile Glu Lys Ile Asp
225                 230                 235                 240

Leu Leu Leu Gln Asn Asp Val Ile Ile Gln Lys Gly Lys Lys His Leu
            245                 250                 255

Asn Glu Trp Thr Asn Leu Lys Glu Arg Arg Asn Asp His His Phe Asp
            260                 265                 270

Thr Tyr Glu Asn Asn Phe Ile Tyr His Lys Gly Thr Gln Asn Cys Lys
        275                 280                 285

Gln Tyr Asp Lys Asn Met Val Asp Gln Asn Val Cys Gly Gln Asn Met
        290                 295                 300

Val Asp His Ile Ile Gln Asn Arg Asn Asn Leu Cys Arg Thr His Phe
305                 310                 315                 320

Tyr Ser Ser Lys Phe Asn Lys Ile Gln Glu Ala Lys Asn Leu Leu Phe
                325                 330                 335

Ser Leu Phe Phe Ser Ser Leu Ser Val Ile Phe Arg Pro Asn Ala Leu
            340                 345                 350

Val Phe Trp Leu Ser Leu Tyr Ile Leu Tyr Ile Ile Lys Asn Ile Phe
            355                 360                 365

Glu Lys Gln Asn Lys Ile Asn Tyr Lys Glu Ile Phe Lys Ile Gly Ile
370                 375                 380

Thr Tyr Thr Phe Phe Leu Thr Ile Ile Ile Ile Asp Ser Tyr
385                 390                 395                 400

Tyr Phe Gly His Ile Thr Phe Pro Phe Trp Asn Phe Val Tyr Asn
                405                 410                 415

Phe Leu Ser Gly Asn Asn Lys Tyr Phe Gly His Ser Phe Phe Phe
            420                 425                 430

Tyr Phe Val Cys Val Ile Pro Ser Ile Tyr Leu Thr Leu Thr Pro Phe
            435                 440                 445

Leu Phe Tyr Gly Tyr Tyr Ile Ile Tyr Asn Asn Ile Leu Asn Lys Val
450                 455                 460

Lys Tyr Lys Thr Ile Asn Ile Tyr Met Tyr Ile Leu Lys Arg Ile Asp
465                 470                 475                 480

Trp Ile Val Tyr Leu Val Thr His Leu Glu Ile Leu Ser Leu Ser Phe
                485                 490                 495

Ser Lys His Lys Glu His Lys Ile Val Ile Gly Tyr Ile Pro Phe Leu
            500                 505                 510

Thr Ile Phe Val Gly Tyr Ala Leu Tyr Ile Ile Lys Leu His Tyr Lys
            515                 520                 525

Lys Tyr Asn Gly Lys Asn Gly Lys Asn Ile Tyr Asn Asn Lys Ile
            530                 535                 540

Gln Tyr Gly Asn Ile Thr Ile Lys Gly Arg Asn Lys Tyr Ile Phe Leu
545                 550                 555                 560

Ile Ser Ser Ser Leu Phe Thr Asn Ile Ser Phe Leu Leu Gln Phe Leu
                565                 570                 575

Cys Ile Leu Phe Phe Cys Leu Ile His Asn Arg Ser Pro Glu His Val
            580                 585                 590

Ala Ser Tyr Phe Arg Asn Leu Glu Thr Lys Asp Asp Gln Asn Ile Tyr
            595                 600                 605

Ile Phe Ile Thr Asn Cys Tyr Asp Ile Pro Leu Tyr Ser His Ile His
            610                 615                 620

Arg Lys Phe Asn Ile Gly Phe Leu Asp Cys Ser Pro Tyr Asp Thr Ser
625                 630                 635                 640

Asn Asp Glu Ala Thr Lys Asn Trp Arg Lys Arg Ile Tyr Glu Asp Lys
                645                 650                 655
```

Phe Lys Glu Gln Phe Phe Asn Ile Phe Gln Glu Lys Lys Asn Asn Asn
                660                 665                 670

His His Ile Asn Ser Thr Tyr Gly Asp Thr Ile Thr Pro Tyr Ile Ile
            675                 680                 685

Pro Asp Lys Ser Phe Tyr Trp Phe Gly His His Phe Asn Lys Lys
    690                 695                 700

Asn Asn Phe Gln Tyr Ile Tyr Gln Asn Ile Asn Leu Ser Cys Leu Asn
705                 710                 715                 720

Tyr Arg Phe His Ile Pro Leu Gln Gly Gln Leu Pro Thr Tyr Ile Val
                725                 730                 735

Thr Thr Thr Ile Glu Leu Thr His Leu Gln Leu Phe Leu Ser Thr Tyr
            740                 745                 750

Asn Tyr Lys Leu Glu Thr Lys Pro Phe Phe Ser Tyr Phe Met Ile Ser
            755                 760                 765

Glu Ala Lys Gly Ile Val Pro Val Tyr His Tyr Ile Phe Lys Arg Val
770                 775                 780

Pro Ser
785

<210> SEQ ID NO 14
<211> LENGTH: 1233
<212> TYPE: DNA
<213> ORGANISM: Plasmodium falciparum

<400> SEQUENCE: 14 atgggcata cacataaaga atataaaaac aatgagaaga gtgcaatatt ttttgagtgg      60
ttgatttttt ttgtgggtat aataattcgt ataattattt attattatgg aaggtggcaa    120
gataaaaact ttaatgttaa gtttacagat gtagattatt atgttttttc tgatgctgca    180
aaatatgtac ttatgaacaa atcaccatat gaaagatata catatagata tacaccttta    240
ttagcatata taatgatacc aaatttttttt gttcattttt cttttgggaa atattattt    300
tcatttatcg atattcttgt tactattctt ataaatcaaa ttataaaaat caaatatact    360
aattgtaaaa attatatatt ttatacttgt ttatggtttt taaatccatt agtcataatt    420
atatcccttc gaggtaatgc agatgttatc ccatgcttct taataatagt aacaatctttt   480
tgtatatata aaaaacatat ctttttgtct tcgattttttt atggactagc tgtgaacttt    540
aaaatatata caattatttta tgcactacca ttcatgttat atttaaataa aaattattta    600
cttggggaaa atattttttca attaaatgaa aaaaaaaaaa aaaaaaaaaa tgacttccta    660
ttaaacacat ttttttatat ttttcgtatt atatctaatt ttttttgtgga attatttaaa    720
ttaaattatg aacagttttt atttgccata tgtagttcct cggtatttct aattttaaac    780
tgtgtattct atatcatata tggatatgaa ttttttgtatg agtctttttat atatcatatt    840
attagacgtg atcataggca taacttttcc ctttttttttt accttatgta tttaagtatt    900
gagaagaatt caaagattat tcccttaata acctttgtac cacaaataat tttagtagcc    960
ttatttggat taaatatgc aagaacgaat ttggaattat ccatgttttt acaaactatt   1020
tctttttattg cattgaataa agtgtgcaca tctcagtatt tcatttggtg tattccattt   1080
ttaccaatta tactttgtgc cataacctta agcaagagaa atatgttttct tataatatcc  1140
tccatttat tttttttattgt ggcaaaagtg ggctcaaaaa gatttctttt attatataaa  1200
tatgtctttt catatattat tttttttttca tga                               1233

<210> SEQ ID NO 15

<211> LENGTH: 410
<212> TYPE: PRT
<213> ORGANISM: Plasmodium falciparum

<400> SEQUENCE: 15

```
Met Gly His Thr His Lys Glu Tyr Lys Asn Asn Glu Lys Ser Ala Ile
1               5                   10                  15

Phe Phe Glu Trp Leu Ile Phe Val Gly Ile Ile Arg Ile Ile
            20                  25                  30

Ile Tyr Tyr Tyr Gly Arg Trp Gln Asp Lys Asn Phe Asn Val Lys Phe
        35                  40                  45

Thr Asp Val Asp Tyr Tyr Val Phe Ser Asp Ala Ala Lys Tyr Val Leu
50                  55                  60

Met Asn Lys Ser Pro Tyr Glu Arg Tyr Thr Tyr Arg Tyr Thr Pro Leu
65                  70                  75                  80

Leu Ala Tyr Ile Met Ile Pro Asn Phe Phe Val His Phe Ser Phe Gly
                85                  90                  95

Lys Ile Leu Phe Ser Phe Ile Asp Ile Leu Val Thr Ile Leu Ile Asn
            100                 105                 110

Gln Ile Ile Lys Ile Lys Tyr Thr Asn Cys Lys Asn Tyr Ile Phe Tyr
        115                 120                 125

Thr Cys Leu Trp Phe Leu Asn Pro Leu Val Ile Ile Ser Leu Arg
130                 135                 140

Gly Asn Ala Asp Val Ile Pro Cys Phe Leu Ile Val Thr Ile Phe
145                 150                 155                 160

Cys Ile Tyr Lys Lys His Ile Phe Leu Ser Ser Ile Phe Tyr Gly Leu
                165                 170                 175

Ala Val Asn Phe Lys Ile Tyr Thr Ile Ile Tyr Ala Leu Pro Phe Met
            180                 185                 190

Leu Tyr Leu Asn Lys Asn Tyr Leu Leu Gly Glu Asn Ile Phe Gln Leu
        195                 200                 205

Asn Glu Lys Lys Lys Lys Lys Asn Asp Phe Leu Leu Asn Thr Phe
210                 215                 220

Phe Tyr Ile Phe Arg Ile Ile Ser Asn Phe Phe Val Glu Leu Phe Lys
225                 230                 235                 240

Leu Asn Tyr Glu Gln Phe Leu Phe Ala Ile Cys Ser Ser Ser Val Phe
                245                 250                 255

Leu Ile Leu Asn Cys Val Phe Tyr Ile Ile Tyr Gly Tyr Glu Phe Leu
            260                 265                 270

Tyr Glu Ser Phe Ile Tyr His Ile Arg Arg Asp His Arg His Asn
        275                 280                 285

Phe Ser Leu Phe Phe Tyr Leu Met Tyr Leu Ser Ile Glu Lys Asn Ser
290                 295                 300

Lys Ile Ile Pro Leu Ile Thr Phe Val Pro Gln Ile Ile Leu Val Ala
305                 310                 315                 320

Leu Phe Gly Phe Lys Tyr Ala Arg Thr Asn Leu Glu Leu Ser Met Phe
                325                 330                 335

Leu Gln Thr Ile Ser Phe Ile Ala Leu Asn Lys Val Cys Thr Ser Gln
            340                 345                 350

Tyr Phe Ile Trp Cys Ile Pro Phe Leu Pro Ile Leu Cys Ala Ile
        355                 360                 365

Thr Leu Ser Lys Arg Asn Met Phe Leu Ile Ile Ser Ser Ile Leu Phe
370                 375                 380

Phe Ile Val Ala Lys Val Gly Ser Lys Arg Phe Leu Leu Leu Tyr Lys
385                 390                 395                 400
```

Tyr Val Phe Ser Tyr Ile Ile Phe Phe Ser
            405                 410

<210> SEQ ID NO 16
<211> LENGTH: 3852
<212> TYPE: DNA
<213> ORGANISM: Plasmodium falciparum

<400> SEQUENCE: 16

| | | | | | |
|---|---|---|---|---|---|
| atgaaaatta | aaataatat | taaaaaaaaa | aatgataacc | tacatcattt | cataagtaat | 60 |
| catacgctaa | tattttctat | tatcctactt | ataaatctat | tgatttttt | ctcatttatc | 120 |
| aatggctatt | tttatgcaag | acaaaaactt | gaagaaaaat | cagaaaacct | tgagctttt | 180 |
| agtaggaaag | tatttggaga | tgaatacgta | gaaagtttga | aaagaaaaa | aaatactttt | 240 |
| tcgattatta | atgcaccata | tgataaagtt | gttatacttt | taatagattc | cttaagattt | 300 |
| gattttaccc | tatacgatac | taattatgaa | aaggaattca | taggaaaaga | aaaaaataca | 360 |
| gatatctaca | ataatatatc | tagcgaaaaa | aaaaatatat | caaatgatgg | ggaaaaaaaa | 420 |
| aactcattat | ttttttaaa | taatatgata | aatgtacatc | acattttaca | aaatgaaaaa | 480 |
| aacaacactt | tattattccg | gtttgatgca | gatgcccta | caataacaac | ttcaaggata | 540 |
| aaatctatat | ttatgggtac | ataccaaat | tatatgaaag | taaatgaaaa | ctttagtcct | 600 |
| acgactagtg | ttgaagataa | tttttttgaa | cagcttcatt | taaataataa | aaaagtaatt | 660 |
| gctatcggtg | ataataccat | tactcatttg | atgaaacatt | tttctaaaga | attagtttat | 720 |
| gagagcttta | atgttttga | tttttattca | ttagatattg | ctgcaaagaa | acatttttat | 780 |
| gaagaatacg | aatcaaatga | ttgggatatt | atgtatatac | atatgttggg | agttgatcat | 840 |
| attggacata | taaaaacacc | caactcaaaa | atcatgggag | atgccttaaa | agattttgat | 900 |
| acattcatat | atgatattat | aaataaaata | aaattagata | atcttaaaaa | tattagcaca | 960 |
| gaagaaaaag | aaaaaatgaa | aataataaaa | aaaaaatat | ataaaactta | tcgaaacggt | 1020 |
| catcacatac | aaaatgaaaa | tgatcatatt | attgataata | tacaaaatga | aaatgatcat | 1080 |
| attattgata | atatacaaaa | tgaaaatgat | catactattg | ataatataca | aagtgaaaat | 1140 |
| gatcatacta | ttgataatat | acaaaatgaa | aatgatcata | ctattgaaga | tatacaaatt | 1200 |
| gataatgatc | atactattga | agatattgaa | atcaaagtg | aacaaaaaaa | tgatgataaa | 1260 |
| aaaacactgt | tcatattttt | tggtgatcat | ggacagctag | atacaggaga | tcacggagga | 1320 |
| tacagcttgg | acgaaaccca | tagtgctctt | tttgcatatt | cacccttaaa | ctttatatct | 1380 |
| ttagataatg | acatcattca | aaataatttt | gttttatatg | ataaagataa | attaaaaaaa | 1440 |
| aatgtgaata | cactgaatga | agaaaataat | aataatgaga | atatagataa | ttataaaaaa | 1500 |
| tatcattcat | atttaaaaga | tagaaataaa | aaatattctt | accattataa | tgttaaatat | 1560 |
| acaaaacaag | taaatttaat | gagtacctta | tccttattaa | ttggatcaac | attaccttat | 1620 |
| ggaaatatag | gaaatattat | tatggatttc | attcccaatg | catatataaa | aaataataat | 1680 |
| aaaaaaaaaa | ataataataa | taataataat | aataataatt | cttcattacc | taatgaacag | 1740 |
| acaaatttat | attatgatct | tttaaattta | cattatattg | ctgaattaaa | ttatgctaac | 1800 |
| ttatggcaat | tgaatagata | cctgaatgaa | tatgaaaaaa | agtataatat | aataaaaaat | 1860 |
| gaagattatc | atttattaa | atcctcatgg | catattatac | aaaaagacaa | aaagaattg | 1920 |
| tttttcaac | caaataaaaa | atttattaaa | aatgacattt | tattaaaaaa | agaaaaagaa | 1980 |
| tcatatatag | aattcataaa | tgaaatgaca | actctaatgg | atatcacaca | aaaatatttt | 2040 |

-continued

```
tactatatat tcaacataaa agaaaaatat ttcttaattt tatctattgt tttaaatata    2100
ttcttattat tattttaaa acattttat tattattcta aattaaatta ttaccataaa    2160
ttaattaaag taacctttaa tgattttaat aaaatatttt atttattact ttgtatatgt    2220
gcattacttt tatattttt tatcttctgt ttatcaatta agaatataaa agatatattc    2280
cgaatatttt ctcatgctaa atcattttc ataagcaata atatagatat gataatacct    2340
agtataaaaa attaccatat gagcgctaaa cgtaacatga atattacgaa taatgacacc    2400
taccatacat cacataagga tcggaaatca ttcacaaata aagaagagaa acaaaataat    2460
acacttatga atatattcta taatattatt tatttcttaa gaataattcg aaaaaaaatt    2520
gttcagtata taatctttat acatttgaca atatacaatc taactatagg taatattatc    2580
tttattctat ttaaattatt tccgaaaatt ataactaatt catttcaaat attaagaagt    2640
aattatttcc ttttgtttgt tattatatgg agctgttgtg aaatgtcctt taattatata    2700
gataaagaaa gatattatat tcattacatt ttaattgtat atgttatatt tgggatgctt    2760
aaatggaagt atcaccgtgt ctttaatata ctaaaagcct tcattttgtt ggtgcttcta    2820
ataattaatg ctttgtatag ccatacaccc gaatattttg accatggtaa agaaaaaata    2880
tatttaaaag aatctgtact aaaatcagtt tttccaatat catcttatat tcttagctta    2940
atattaataa atagtggtat taataattta ctgaaaaaac gaataaaaat aataataacc    3000
caaatatgga cattacaata tatcctcgtt tttttgttct taaataatat ataccataga    3060
tatattcaat ttataacacc cccaagtatt tatttcttaa ccatttcaac cttcatattc    3120
atattcaata caaatttagg tgtattattt ctctttatta tgacatttct ttttttctac    3180
tttattctta taagttccaa ttgttcagaa aatatgatcc aaatgaatga cataacatcg    3240
acatggataa atgaaaatat acataataga aatgatccta taattacaaa aggaaatttg    3300
gagaataaag aaaagtgtac ttcatgtaat acatctataa aagaaaaatt ttattataaa    3360
ttaatgatag aaaaattcaa attattaaat acatgctctg tattaaatga agaagaaata    3420
atgggaatac aaatttataa attaattaga gatatttctt attttttatat aaatgaaaca    3480 gattttata ttttatcatg tgtacttta atatattctt ttttttataac gggacataaa    3540 tttattttaa ataacttacc actagtttca ggttatgttg gattgtataa atatgtgtgg    3600
ccaataagtc agtttatat ttttaatcat attttttttc cattcttctt ttcgttattt    3660
tttatcattt atatttataa cataagaagg ataaaaatta taaattcttt taagcaattt    3720
gatttgtatt attttatgt ttatccacta atgaactttt ccttcaaggc ctccttttg    3780 ttttgttgca agtttattat atctgtatgg gtttcatatt acttgaatct gcacataatg    3840
gtaaaaatat aa                                                      3852
```

<210> SEQ ID NO 17
<211> LENGTH: 1283
<212> TYPE: PRT
<213> ORGANISM: Plasmodium falciparum

<400> SEQUENCE: 17

```
Met Lys Ile Lys Asn Asn Ile Lys Lys Lys Asn Asp Asn Leu His His
 1               5                  10                  15

Phe Ile Ser Asn His Thr Leu Ile Phe Ser Ile Ile Leu Leu Ile Asn
             20                  25                  30

Leu Leu Ile Phe Phe Ser Phe Ile Asn Gly Tyr Phe Tyr Ala Arg Gln
         35                  40                  45

Lys Leu Glu Glu Lys Ser Glu Asn Leu Glu Leu Phe Ser Arg Lys Val
```

```
                50                  55                  60
Phe Gly Asp Glu Tyr Val Glu Ser Leu Lys Lys Lys Asn Thr Phe
 65                  70                  75                  80

Ser Ile Ile Asn Ala Pro Tyr Asp Lys Val Ile Leu Leu Ile Asp
                     85                  90                  95

Ser Leu Arg Phe Asp Phe Thr Leu Tyr Asp Thr Asn Tyr Glu Lys Glu
                100                 105                 110

Phe Ile Gly Lys Glu Lys Asn Thr Asp Ile Tyr Asn Asn Ile Ser Ser
                115                 120                 125

Glu Lys Lys Asn Ile Ser Asn Asp Gly Glu Lys Lys Asn Ser Leu Phe
                130                 135                 140

Phe Leu Asn Asn Met Ile Asn Val His His Ile Leu Gln Asn Glu Lys
145                 150                 155                 160

Asn Asn Thr Leu Leu Phe Arg Phe Asp Ala Asp Ala Pro Thr Ile Thr
                    165                 170                 175

Thr Ser Arg Ile Lys Ser Ile Phe Met Gly Thr Ile Pro Asn Tyr Met
                    180                 185                 190

Glu Val Asn Glu Asn Phe Ser Pro Thr Thr Ser Val Glu Asp Asn Phe
                    195                 200                 205

Phe Glu Gln Leu His Leu Asn Asn Lys Lys Val Ile Ala Ile Gly Asp
210                 215                 220

Asn Thr Ile Thr His Leu Met Lys His Phe Ser Lys Glu Leu Val Tyr
225                 230                 235                 240

Glu Ser Phe Asn Val Phe Asp Phe Tyr Ser Leu Asp Ile Ala Ala Lys
                    245                 250                 255

Lys His Phe Tyr Glu Glu Tyr Glu Ser Asn Asp Trp Asp Ile Met Tyr
                    260                 265                 270

Ile His Met Leu Gly Val Asp His Ile Gly His Ile Lys Thr Pro Asn
                    275                 280                 285

Ser Lys Ile Met Gly Asp Ala Leu Lys Asp Phe Asp Thr Phe Ile Tyr
                    290                 295                 300

Asp Ile Ile Asn Lys Ile Lys Leu Asp Asn Leu Lys Asn Ile Ser Thr
305                 310                 315                 320

Glu Glu Lys Glu Lys Met Lys Ile Ile Lys Lys Lys Ile Tyr Lys Thr
                    325                 330                 335

Tyr Arg Asn Gly His His Ile Gln Asn Glu Asn Asp His Ile Ile Asp
                340                 345                 350

Asn Ile Gln Asn Glu Asn Asp His Ile Ile Asp Asn Ile Gln Asn Glu
                355                 360                 365

Asn Asp His Thr Ile Asp Asn Ile Gln Ser Glu Asn Asp His Thr Ile
                370                 375                 380

Asp Asn Ile Gln Asn Glu Asn Asp His Thr Ile Glu Asp Ile Gln Ile
385                 390                 395                 400

Asp Asn Asp His Thr Ile Glu Asp Ile Glu Asn Gln Ser Glu Gln Lys
                    405                 410                 415

Asn Asp Asp Lys Lys Thr Leu Phe Ile Phe Phe Gly Asp His Gly Gln
                    420                 425                 430

Leu Asp Thr Gly Asp His Gly Gly Tyr Ser Leu Asp Glu Thr His Ser
                435                 440                 445

Ala Leu Phe Ala Tyr Ser Pro Leu Asn Phe Ile Ser Leu Asp Asn Asp
                450                 455                 460

Ile Ile Gln Asn Asn Phe Val Leu Tyr Asp Lys Asp Lys Leu Lys Lys
465                 470                 475                 480
```

```
Asn Val Asn Thr Leu Asn Glu Glu Asn Asn Asn Asn Glu Asn Ile Asp
                485                 490                 495

Asn Tyr Lys Lys Tyr His Ser Tyr Leu Lys Asp Arg Asn Lys Lys Tyr
            500                 505                 510

Ser Tyr His Tyr Asn Val Lys Tyr Thr Lys Gln Val Asn Leu Met Ser
            515                 520                 525

Thr Leu Ser Leu Leu Ile Gly Ser Thr Leu Pro Tyr Gly Asn Ile Gly
            530                 535                 540

Asn Ile Ile Met Asp Phe Ile Pro Asn Ala Tyr Ile Lys Asn Asn Asn
545                 550                 555                 560

Lys Lys Lys Asn Asn Asn Asn Asn Asn Asn Asn Ser Ser Leu
                565                 570                 575

Pro Asn Glu Gln Thr Asn Leu Tyr Tyr Asp Leu Leu Asn Leu His Tyr
            580                 585                 590

Ile Ala Glu Leu Asn Tyr Ala Asn Leu Trp Gln Leu Asn Arg Tyr Leu
            595                 600                 605

Asn Glu Tyr Glu Lys Lys Tyr Asn Ile Ile Lys Asn Glu Asp Tyr His
            610                 615                 620

Phe Ile Lys Ser Ser Trp His Ile Ile Gln Lys Asp Lys Lys Glu Leu
625                 630                 635                 640

Phe Phe Gln Pro Asn Lys Lys Phe Ile Lys Asn Asp Ile Leu Leu Lys
                645                 650                 655

Lys Glu Lys Glu Ser Tyr Ile Glu Phe Ile Asn Glu Met Thr Thr Leu
            660                 665                 670

Met Asp Ile Thr Gln Lys Tyr Phe Tyr Tyr Ile Phe Asn Ile Lys Glu
            675                 680                 685

Lys Tyr Phe Leu Ile Leu Ser Ile Val Leu Asn Ile Phe Leu Leu Leu
            690                 695                 700

Phe Leu Lys His Phe Tyr Tyr Ser Lys Leu Asn Tyr Tyr His Lys
705                 710                 715                 720

Leu Ile Lys Val Thr Phe Asn Asp Phe Asn Lys Asn Ile Tyr Leu Leu
                725                 730                 735

Leu Cys Ile Cys Ala Leu Leu Leu Tyr Phe Phe Ile Phe Cys Leu Ser
            740                 745                 750

Ile Lys Glu Tyr Lys Asp Ile Phe Arg Ile Phe Ser His Ala Lys Ile
            755                 760                 765

Ile Phe Ile Ser Asn Asn Ile Asp Met Ile Ile Pro Ser Ile Lys Asn
            770                 775                 780

Tyr His Met Ser Ala Lys Arg Asn Met Asn Ile Thr Asn Asn Asp Thr
785                 790                 795                 800

Tyr His Thr Ser His Lys Asp Arg Lys Ser Phe Thr Asn Lys Glu Glu
                805                 810                 815

Lys Gln Asn Asn Thr Leu Met Asn Ile Phe Tyr Asn Ile Ile Tyr Phe
            820                 825                 830

Leu Arg Ile Ile Arg Lys Lys Ile Val Gln Tyr Ile Phe Ile His
            835                 840                 845

Leu Thr Ile Tyr Asn Leu Thr Ile Gly Asn Ile Phe Ile Leu Phe
            850                 855                 860

Lys Leu Phe Pro Lys Ile Ile Thr Asn Ser Phe Gln Ile Leu Arg Ser
865                 870                 875                 880

Asn Tyr Phe Leu Leu Phe Val Ile Ile Trp Ser Cys Cys Glu Met Ser
                885                 890                 895

Phe Asn Tyr Ile Asp Lys Glu Arg Tyr Tyr Ile His Tyr Ile Leu Ile
            900                 905                 910
```

Val Tyr Val Ile Phe Gly Met Leu Lys Trp Lys Tyr His Arg Val Phe
            915                 920                 925

Asn Ile Leu Lys Ala Phe Ile Leu Val Leu Leu Ile Ile Asn Ala
        930                 935                 940

Leu Tyr Ser His Thr Pro Glu Tyr Phe Asp His Gly Lys Glu Lys Ile
945                 950                 955                 960

Tyr Leu Lys Glu Ser Val Leu Lys Ser Val Phe Pro Ile Ser Ser Tyr
                965                 970                 975

Ile Leu Ser Leu Ile Leu Ile Asn Ser Gly Ile Asn Asn Leu Leu Lys
            980                 985                 990

Lys Arg Ile Lys Ile Ile Ile Thr Gln Ile Trp Thr Leu Gln Tyr Ile
        995                 1000                1005

Leu Val Phe Leu Phe Leu Asn Asn Ile Tyr His Arg Tyr Ile Gln Phe
    1010                1015                1020

Ile Thr Pro Pro Ser Ile Tyr Phe Leu Thr Ile Ser Thr Phe Ile Phe
1025                1030                1035                1040

Ile Phe Asn Thr Asn Leu Gly Val Leu Phe Leu Phe Tyr Met Thr Phe
                1045                1050                1055

Leu Phe Phe Tyr Phe Ile Leu Ile Ser Ser Asn Cys Ser Glu Asn Met
            1060                1065                1070

Ile Gln Met Asn Asp Ile Thr Ser Thr Trp Ile Asn Glu Asn Ile His
        1075                1080                1085

Asn Arg Asn Asp Pro Ile Ile Thr Lys Gly Asn Leu Glu Asn Lys Glu
    1090                1095                1100

Lys Cys Thr Ser Cys Asn Thr Ser Ile Lys Glu Lys Phe Tyr Tyr Lys
1105                1110                1115                1120

Leu Met Ile Glu Lys Phe Lys Leu Leu Asn Thr Cys Ser Val Leu Asn
                1125                1130                1135

Glu Glu Glu Ile Met Gly Ile Gln Ile Tyr Lys Leu Ile Arg Asp Ile
            1140                1145                1150

Ser Tyr Phe Tyr Ile Asn Glu Thr Asp Phe Tyr Ile Leu Ser Cys Val
        1155                1160                1165

Leu Leu Ile Tyr Ser Phe Phe Ile Thr Gly His Lys Phe Ile Leu Asn
    1170                1175                1180

Asn Leu Pro Leu Val Ser Gly Tyr Val Gly Leu Tyr Lys Tyr Val Trp
1185                1190                1195                1200

Pro Ile Ser Gln Phe Tyr Ile Phe Asn His Ile Phe Phe Pro Phe Phe
                1205                1210                1215

Phe Ser Leu Phe Phe Ile Ile Tyr Ile Tyr Asn Ile Arg Arg Ile Lys
            1220                1225                1230

Ile Ile Asn Ser Phe Lys Gln Phe Asp Leu Tyr Tyr Phe Tyr Val Tyr
        1235                1240                1245

Pro Leu Met Asn Phe Ser Phe Lys Ala Ser Phe Leu Phe Cys Cys Lys
    1250                1255                1260

Phe Ile Ile Ser Val Trp Val Ser Tyr Tyr Leu Asn Leu His Ile Met
1265                1270                1275                1280

Val Lys Ile

<210> SEQ ID NO 18
<211> LENGTH: 2433
<212> TYPE: DNA
<213> ORGANISM: Plasmodium falciparum

<400> SEQUENCE: 18

-continued

```
atgggattttt cagaaaatcc caaattctgc ctgctcataa ataagcttat caagaaatct    60
aaagttatag gcgttttctt atcaattatt ggtgtgattt tcttttggt gtttaataag    120
tttaataaga atgctgaatt agacgctagg acatttaccc aatttgttgg taattcagta   180
ttgaacaaaa agaatgagaa gttttataat gatacaaatt cttatttcat gaactataca   240
tatgaaggga aagaagatat aataaagttg atatatgatt atattagaaa aaatatatta   300
gtaaatgtag agaatgagat ggttaaaata aaattaacgg atagaattga acagaatata   360
ttgataagta atgtaggatg taaatattgt aataatatgg aaagtttagt tgtggtaata   420
aattttgatt ttaaagaaag gaaatatttt catagcgtaa ttatcggttt aacgttaatg   480
gaacattttt ctaaatgtaa ctatatgagt aaggatgtga cttttttatt taccaataaa   540
gaattattat attctttagg tgttcaagaa tttatacaaa atattttta taataatact   600
aatagaattg gaaaaaaaat tattagatct tctactatta ttgaatttga ttctatttat   660
ccttcttata ttaaaattaa ttatgaagga ttaaatggta tgttacctaa tcaagactta   720
atattattat taacaaatga acttcatttt tattctattc ctattaaaat ggagcttact   780
catggttcca tatttgatat ggccctagaa aagaattatg aaaatggtca catatacttt   840
ctgaggtaca aaaaaaaata tgaatatata cgtgatgata atgatgaaat caagaacatt   900
cccgcattta ctgcaacggg gggtagcaaa gtacccataa gaaataaaat gattaatttg   960
ttcaacttaa ccaaagcatt acaaagttat ttaagaagtc agagtaatac acatgaaggc  1020
ttttgtcatt cttcaaattt ttattttttt aatacattca gaaggcatat accaataagt  1080
atatattgtt atagtgttta tttaatatgc gcatatagca taatgaaatt atttaaatca  1140
acgatattta gaagctacat aaattttta acaggtttct acacttattt gattacaata  1200
ttaattattt ccctacctat atatttaatt tcaacaaata aaaaatttta tgagttgttg  1260
aatttttgaag aaaattatat tccttcatgt tatgaatggc atcctgataa ttttgataaa  1320
tatataaaaa ttgcaaatat atggtggaat gttttatttt tctcaatttt tggtgcattt  1380
tttttaatt tatttatttc ttttttagtt aataaaaaaa gaaagttat accaaaaaaa  1440
aatgatcaaa atgaatcatt tgatggctat aaaaaggtag agaaggtaga acgaattta   1500
atattagaaa aaatcaaaga attgcaaaat gaaataatga acgaaaagg tattacaaat   1560
aatcataata atattaaaaa ttataatatt tatacaaatg aaaatatata caataataat   1620
ataaataata taaataataa taataatatt tatgaaaact tatatgataa tggagaagta   1680
aaaaaaaaca ttctggttaa accaaaaatt ataaatagcg atgatgaaga ttttcttctt   1740
gaaaaaaaaa attccgaatt cattaaaaaa atagaaaaac aaatagaaat attagaagaa   1800
aaattggaat tttaagtaa tgatgaaaat gtaaaatata ttttttataa taattctata   1860
gcaccattta atacaatgat gatatatatg aatattttt atttcatatt agtagcgcta   1920
ttaagttcgt tatataattg gtcctattct gtattattta gcctgctatt tgtaattcct   1980
atatcaattt tacataattt aaaaacaaaa ccagtcagaa tttttaagaa gattattctt   2040
tcacttttta ttctttgtat gtttatttat atgtatccta atgataatca tctttggaat   2100
ataagacaga agctaactaa tttatttagg aataatatat caaaatgttg taaatattta   2160
gacaagcaca aaatattaca aagcaaatat ttcccagaaa gtttgcaatt tatttgttcg   2220
aataggttat ttgattcatt ttactcaaat aaatattttt tggataatct aaatattaaa   2280
tttagttatg tcttggatat tcaaaatgga ttccttattaa ctttatacaa tttagcaaga   2340
aatcattttt gtattggtac agctacctat cctttaatat gctttacctt attcccaata   2400
``` gtatttata tagtttttt atttttttgt taa 2433

<210> SEQ ID NO 19
<211> LENGTH: 810
<212> TYPE: PRT
<213> ORGANISM: Plasmodium falciparum

<400> SEQUENCE: 19

Met Gly Phe Ser Glu Asn Pro Lys Phe Cys Leu Leu Ile Asn Lys Leu
 1               5                  10                  15

Ile Lys Lys Ser Lys Val Ile Gly Val Phe Leu Ser Ile Ile Gly Val
             20                  25                  30

Ile Phe Phe Leu Val Phe Asn Lys Phe Asn Lys Asn Ala Glu Leu Asp
         35                  40                  45

Ala Arg Thr Phe Thr Gln Phe Val Gly Asn Ser Val Leu Asn Lys Lys
     50                  55                  60

Asn Glu Lys Phe Tyr Asn Asp Thr Asn Ser Tyr Phe Met Asn Tyr Thr
 65                  70                  75                  80

Tyr Glu Gly Lys Glu Asp Ile Ile Lys Leu Ile Tyr Asp Tyr Ile Arg
                 85                  90                  95

Lys Asn Ile Leu Val Asn Val Glu Asn Glu Met Val Lys Ile Lys Leu
            100                 105                 110

Thr Asp Arg Ile Glu Gln Asn Ile Leu Ile Ser Asn Val Gly Cys Lys
        115                 120                 125

Tyr Cys Asn Asn Met Glu Ser Leu Val Val Val Ile Asn Phe Asp Phe
    130                 135                 140

Lys Glu Arg Lys Tyr Phe His Ser Val Ile Ile Gly Leu Thr Leu Met
145                 150                 155                 160

Glu His Phe Ser Lys Cys Asn Tyr Met Ser Lys Asp Val Thr Phe Leu
                165                 170                 175

Phe Thr Asn Lys Glu Leu Leu Tyr Ser Leu Gly Val Gln Glu Phe Ile
            180                 185                 190

Gln Lys Tyr Phe Tyr Asn Asn Thr Asn Arg Ile Gly Lys Lys Ile Ile
        195                 200                 205

Arg Ser Ser Thr Ile Ile Glu Phe Asp Ser Ile Tyr Pro Ser Tyr Ile
    210                 215                 220

Lys Ile Asn Tyr Glu Gly Leu Asn Gly Met Leu Pro Asn Gln Asp Leu
225                 230                 235                 240

Ile Leu Leu Leu Thr Asn Glu Leu His Phe Tyr Ser Ile Pro Ile Lys
                245                 250                 255

Met Glu Leu Thr His Gly Ser Ile Phe Asp Met Ala Leu Glu Lys Asn
            260                 265                 270

Tyr Glu Asn Gly His Ile Tyr Phe Leu Arg Tyr Lys Lys Lys Tyr Glu
        275                 280                 285

Tyr Ile Arg Asp Asp Asn Asp Glu Ile Lys Asn Ile Pro Ala Phe Thr
    290                 295                 300

Ala Thr Gly Gly Ser Lys Val Pro Ile Arg Asn Lys Met Ile Asn Leu
305                 310                 315                 320

Phe Asn Leu Thr Lys Ala Leu Gln Ser Tyr Leu Arg Ser Gln Ser Asn
                325                 330                 335

Thr His Glu Gly Phe Cys His Ser Ser Asn Phe Tyr Phe Phe Asn Thr
            340                 345                 350

Phe Arg Arg His Ile Pro Ile Ser Ile Tyr Cys Tyr Ser Val Tyr Leu
        355                 360                 365

Ile Cys Ala Tyr Ser Ile Met Lys Leu Phe Lys Ser Thr Ile Phe Arg

-continued

```
            370                 375                 380
Ser Tyr Ile Asn Phe Leu Thr Gly Phe Tyr Thr Tyr Leu Ile Thr Ile
385                 390                 395                 400

Leu Ile Ile Ser Leu Pro Ile Tyr Leu Ile Ser Thr Asn Lys Lys Phe
                    405                 410                 415

Tyr Glu Leu Leu Asn Phe Glu Glu Asn Tyr Ile Pro Ser Cys Tyr Glu
                420                 425                 430

Trp His Pro Asp Asn Phe Asp Lys Tyr Ile Lys Ile Ala Asn Ile Trp
                    435                 440                 445

Trp Asn Val Leu Phe Phe Ser Ile Phe Gly Ala Phe Phe Asn Leu
450                 455                 460

Phe Ile Ser Phe Leu Val Asn Lys Lys Arg Lys Val Ile Pro Lys Lys
465                 470                 475                 480

Asn Asp Gln Asn Glu Ser Phe Asp Gly Tyr Lys Lys Val Glu Lys Val
                    485                 490                 495

Glu Arg Ile Leu Ile Leu Glu Lys Ile Lys Glu Leu Gln Asn Glu Ile
                500                 505                 510

Met Lys Arg Lys Gly Ile Thr Asn Asn His Asn Asn Ile Lys Asn Tyr
            515                 520                 525

Asn Ile Tyr Thr Asn Glu Asn Ile Tyr Asn Asn Asn Ile Asn Asn Ile
            530                 535                 540

Asn Asn Asn Asn Asn Ile Tyr Glu Asn Leu Tyr Asp Asn Gly Glu Val
545                 550                 555                 560

Lys Lys Asn Ile Leu Val Lys Pro Lys Ile Ile Asn Ser Asp Asp Glu
                565                 570                 575

Asp Phe Leu Leu Glu Lys Lys Asn Ser Glu Phe Ile Lys Lys Ile Glu
            580                 585                 590

Lys Gln Ile Glu Ile Leu Glu Glu Lys Leu Glu Phe Leu Ser Asn Asp
            595                 600                 605

Glu Asn Val Lys Tyr Ile Phe Tyr Asn Asn Ser Ile Ala Pro Phe Asn
            610                 615                 620

Thr Met Met Ile Tyr Met Asn Ile Phe Tyr Phe Ile Leu Val Ala Leu
625                 630                 635                 640

Leu Ser Ser Leu Tyr Asn Trp Ser Tyr Ser Val Leu Phe Ser Leu Leu
                    645                 650                 655

Phe Val Ile Pro Ile Ser Ile Leu His Asn Leu Lys Thr Lys Pro Val
                    660                 665                 670

Arg Ile Phe Lys Lys Ile Ile Leu Ser Leu Phe Ile Leu Cys Met Phe
                    675                 680                 685

Ile Tyr Met Tyr Pro Asn Asp Asn His Leu Trp Asn Ile Arg Gln Lys
            690                 695                 700

Leu Thr Asn Leu Phe Arg Asn Asn Ile Ser Lys Cys Cys Lys Tyr Leu
705                 710                 715                 720

Asp Lys His Lys Ile Leu Gln Ser Lys Tyr Phe Pro Glu Ser Leu Gln
                    725                 730                 735

Phe Ile Cys Ser Asn Arg Leu Phe Asp Ser Phe Tyr Ser Asn Lys Tyr
                740                 745                 750

Phe Leu Asp Asn Leu Asn Ile Lys Phe Ser Tyr Val Leu Asp Ile Gln
                    755                 760                 765

Asn Gly Phe Leu Leu Thr Leu Tyr Asn Leu Ala Arg Asn His Phe Cys
            770                 775                 780

Ile Gly Thr Ala Thr Tyr Pro Leu Ile Cys Phe Thr Leu Phe Pro Ile
785                 790                 795                 800
```

```
Val Phe Tyr Ile Val Phe Leu Phe Phe Cys
            805                 810
```

<210> SEQ ID NO 20
<211> LENGTH: 780
<212> TYPE: DNA
<213> ORGANISM: Plasmodium falciparum

<400> SEQUENCE: 20

```
atggttattc gattttcct gtttgtcatt acactcttag cttatgcat aaatatggtg      60
tgttgtaatt ttaaatattc gattatatta cctacttaca atgaaaaaga aacttacca    120
tatcttattt atatgataat tgatgaatta ataaacatg aaattaaatt tgaataatt    180
gtaatagatg ataatagtca agatggtact gcagatgtgt acaaaaagtt acaaaacatt  240
tttaaggatg aagaattatt attaatacaa agaaaaggaa attagggtt aggttctgca   300
tatatggaag gtttaaaaaa tgtaacagga gattttgtta ataatggg tgctgattta   360
tcacatcatc ctaaatatat ttataacttt attaaaaaac aaagagaaaa aaattgtgac  420
attgttacag cacaagata taagaaccaa ggtggaatat caggatggtc atttaataga  480
attataataa gtagagtagc aaattttta gctcaatttc tattattcat taatctatca  540
gatttaaccg ggtctttag attatataaa actaatgtac tgaaggaact tatgcaatct  600
attaataata caggttatgt ttttcaaatg gaagttcttg taagagcata taaatggga   660
aaatctatag aagaagttgg ttacgttttt gttgatagat tatttggaaa atcaaaactg  720
gaaactacag atatttaca atacttatca ggtcttttca gttattctg gtcaatataa   780
```

<210> SEQ ID NO 21
<211> LENGTH: 259
<212> TYPE: PRT
<213> ORGANISM: Plasmodium falciparum

<400> SEQUENCE: 21

```
Met Val Ile Arg Phe Phe Leu Phe Val Ile Thr Leu Leu Gly Leu Cys
  1               5                  10                  15

Ile Asn Met Val Cys Cys Asn Phe Lys Tyr Ser Ile Ile Leu Pro Thr
             20                  25                  30

Tyr Asn Glu Lys Glu Asn Leu Pro Tyr Leu Ile Tyr Met Ile Ile Asp
         35                  40                  45

Glu Leu Asn Lys His Glu Ile Lys Phe Glu Ile Ile Val Ile Asp Asp
     50                  55                  60

Asn Ser Gln Asp Gly Thr Ala Asp Val Tyr Lys Lys Leu Gln Asn Ile
 65                  70                  75                  80

Phe Lys Asp Glu Glu Leu Leu Leu Ile Gln Arg Lys Gly Lys Leu Gly
                 85                  90                  95

Leu Gly Ser Ala Tyr Met Glu Gly Leu Lys Asn Val Thr Gly Asp Phe
            100                 105                 110

Val Ile Ile Met Asp Ala Asp Leu Ser His His Pro Lys Tyr Ile Tyr
        115                 120                 125

Asn Phe Ile Lys Lys Gln Arg Glu Lys Asn Cys Asp Ile Val Thr Gly
    130                 135                 140

Thr Arg Tyr Lys Asn Gln Gly Gly Ile Ser Gly Trp Ser Phe Asn Arg
145                 150                 155                 160

Ile Ile Ile Ser Arg Val Ala Asn Phe Leu Ala Gln Phe Leu Leu Phe
                165                 170                 175

Ile Asn Leu Ser Asp Leu Thr Gly Ser Phe Arg Leu Tyr Lys Thr Asn
            180                 185                 190
```

Val Leu Lys Glu Leu Met Gln Ser Ile Asn Asn Thr Gly Tyr Val Phe
            195                 200                 205

Gln Met Glu Val Leu Val Arg Ala Tyr Lys Met Gly Lys Ser Ile Glu
        210                 215                 220

Glu Val Gly Tyr Val Phe Val Asp Arg Leu Phe Gly Lys Ser Lys Leu
225                 230                 235                 240

Glu Thr Thr Asp Ile Leu Gln Tyr Leu Ser Gly Leu Phe Lys Leu Phe
            245                 250                 255

Trp Ser Ile

<210> SEQ ID NO 22
<211> LENGTH: 843
<212> TYPE: DNA
<213> ORGANISM: Saccharomyces cerevisiae

<400> SEQUENCE: 22

| | |
|---|---|
| atgacaagat ctccctggaa gcgcctacta tggttgaaac aggagtaccc agataattat | 60 |
| acagatccaa gttttattga gttgagagca agacaaaagg ctgagagtaa ccagaagtct | 120 |
| gatagaaaat tatcagaagc tgctcgcgct caaattaggt tggattttat aagtttctac | 180 |
| caaaccatat tgaacacttc tttcatttac atcactttta catatattta ctattatggc | 240 |
| ttcgatccta ttccgccaac tatttttcctt tcatttataa cattgattat atcaaggacg | 300 |
| aaagtcgacc ctctattgtc ctcattcatg gacgtaaagt cttcgctgat tatcacattt | 360 |
| gcaatgttga ctctctctcc agtcctcaaa tctctttcta aaacaactgc atctgattcc | 420 |
| atatggacat tgtcttttttg gctgacccta tggtacattt tcgttatttc gtcaacaaag | 480 |
| tccaaagata aaccctctaa cctttccacc aatatacttg tcgcccttgt tgctgtccta | 540 |
| tcatcgaggc tttcgaccac aatcgacgta ttctgttttc ttttaatttg tattcagttg | 600 |
| aatatcattc tacccactta tttatcggtg acgaataagg tagtaccaat aatttcaaat | 660 |
| attattgtat actcattttt gaatgttgct ctaggttgga tttatatgct gttgattttc | 720 |
| tttgcttcag tattttatat tactgtttta cctaagtggt tcatctactg gaaaatcaat | 780 |
| tatcataaac gggataacga tctactaagt acatgggatg caagaacacc aatattggat | 840 |
| tag | 843 |

<210> SEQ ID NO 23
<211> LENGTH: 280
<212> TYPE: PRT
<213> ORGANISM: Saccharomyces cerevisiae

<400> SEQUENCE: 23

Met Thr Arg Ser Pro Trp Lys Arg Leu Leu Trp Leu Lys Gln Glu Tyr
1               5                   10                  15

Pro Asp Asn Tyr Thr Asp Pro Ser Phe Ile Glu Leu Arg Ala Arg Gln
            20                  25                  30

Lys Ala Glu Ser Asn Gln Lys Ser Asp Arg Lys Leu Ser Glu Ala Ala
        35                  40                  45

Arg Ala Gln Ile Arg Leu Asp Phe Ile Ser Phe Tyr Gln Thr Ile Leu
    50                  55                  60

Asn Thr Ser Phe Ile Tyr Ile Thr Phe Thr Tyr Ile Tyr Tyr Tyr Gly
65                  70                  75                  80

Phe Asp Pro Ile Pro Pro Thr Ile Phe Leu Ser Phe Ile Thr Leu Ile
            85                  90                  95

Ile Ser Arg Thr Lys Val Asp Pro Leu Leu Ser Ser Phe Met Asp Val

```
            100                 105                  110
Lys Ser Ser Leu Ile Ile Thr Phe Ala Met Leu Thr Leu Ser Pro Val
        115                 120                 125

Leu Lys Ser Leu Ser Lys Thr Thr Ala Ser Asp Ser Ile Trp Thr Leu
        130                 135                 140

Ser Phe Trp Leu Thr Leu Trp Tyr Ile Phe Val Ile Ser Ser Thr Lys
145                 150                 155                 160

Ser Lys Asp Lys Pro Ser Asn Leu Ser Thr Asn Ile Leu Val Ala Leu
                165                 170                 175

Val Ala Val Leu Ser Ser Arg Leu Ser Thr Thr Ile Asp Val Phe Cys
            180                 185                 190

Phe Leu Leu Ile Cys Ile Gln Leu Asn Ile Ile Leu Pro Thr Tyr Leu
        195                 200                 205

Ser Val Thr Asn Lys Val Val Pro Ile Ile Ser Asn Ile Ile Val Tyr
        210                 215                 220

Ser Phe Leu Asn Val Ala Leu Gly Trp Ile Tyr Met Leu Leu Ile Phe
225                 230                 235                 240

Phe Ala Ser Val Phe Tyr Ile Thr Val Leu Pro Lys Trp Phe Ile Tyr
                245                 250                 255

Trp Lys Ile Asn Tyr His Lys Arg Asp Asn Asp Leu Leu Ser Thr Trp
            260                 265                 270

Asp Ala Arg Thr Pro Ile Leu Asp
            275                 280

<210> SEQ ID NO 24
<211> LENGTH: 764
<212> TYPE: DNA
<213> ORGANISM: Saccharomyces cerevisiae

<400> SEQUENCE: 24
atgattagta aagagtatga atttggtaag actagtatac tgaatagaaa gaagtataca      60
ttagttatcg atgaagacaa gaatggcaat tttataagat ttaccgtttt acctgtatct     120
aaccgaaagt tcaaaaaagt caagcaaaat gggagggtag agattaacat ggcatacaa      180 tatcaccaaa ttgtacttat tttactactg aatattttgt tctatgtaat ttgcctaaga     240
tcaagatttc tcgaacatat taatagaact tttgaagtga caatcgcgcg aagtttccag     300
atcttaatta taatgggatt gtttgcctta ggtacaatta tacttgtgag gggacctagt     360
gtggaaactg taacaatttt caaagaaagt ggactacagc tgtccagagt gaagggtatg     420
gttatatttc ctcaacaatg gaatcggaag ttctttgaac aagtagagtt tatatccaat     480
gaaagaatta ttgatgtagt gatcaatgaa ggattctgtc ggggatttcg agtgatattc     540
tatcttgcag caattgtacg taaatcgtct acgcttaagc tattatttcc agtatgtatt     600
caagcgaatt taagattgtt tcttacttca acgatctgat tagaaatact aacacaacaa     660
tgcagtcaaa tttgcccagt atcgatgacc aacgtctaat atacaacata tctagaaaat     720
atctcagtaa gcaagaaaaa cccctgagca gaccaaaaga ttga                      764

<210> SEQ ID NO 25
<211> LENGTH: 229
<212> TYPE: PRT
<213> ORGANISM: Saccharomyces cerevisiae

<400> SEQUENCE: 25

Met Ile Ser Lys Glu Tyr Glu Phe Gly Lys Thr Ser Ile Leu Asn Arg
1               5                   10                  15
```

```
Lys Lys Tyr Thr Leu Val Ile Asp Glu Asp Lys Asn Gly Asn Phe Ile
            20                  25                  30
Arg Phe Thr Val Leu Pro Val Ser Asn Arg Lys Phe Lys Val Lys
        35                  40                  45
Gln Asn Gly Arg Val Glu Ile Asn Met Gly Ile Gln Tyr His Gln Ile
 50                  55                  60
Val Leu Ile Leu Leu Leu Asn Ile Leu Phe Tyr Val Ile Cys Leu Arg
 65                  70                  75                  80
Ser Arg Phe Leu Glu His Ile Asn Arg Thr Phe Glu Val Thr Ile Ala
                 85                  90                  95
Arg Ser Phe Gln Ile Leu Ile Ile Met Gly Leu Phe Ala Leu Gly Thr
            100                 105                 110
Ile Ile Leu Val Arg Gly Pro Ser Val Glu Thr Val Thr Ile Phe Lys
            115                 120                 125
Glu Ser Gly Leu Gln Leu Ser Arg Val Lys Gly Met Val Ile Phe Pro
130                 135                 140
Gln Gln Trp Asn Arg Lys Phe Phe Glu Gln Val Glu Phe Ile Ser Asn
145                 150                 155                 160
Glu Arg Ile Ile Asp Val Val Ile Asn Glu Gly Phe Cys Arg Gly Phe
                165                 170                 175
Arg Val Ile Phe Tyr Leu Ala Ala Ile Val Arg Lys Ser Ser Thr Leu
            180                 185                 190
Lys Leu Leu Phe Pro Ser Asn Leu Pro Ser Ile Asp Asp Gln Arg Leu
            195                 200                 205
Ile Tyr Asn Ile Ser Arg Lys Tyr Leu Ser Lys Gln Glu Lys Pro Leu
210                 215                 220
Ser Arg Pro Lys Asp
225

<210> SEQ ID NO 26
<211> LENGTH: 423
<212> TYPE: DNA
<213> ORGANISM: Saccharomyces cerevisiae

<400> SEQUENCE: 26
atgtatacaa aagagtacta ctggttttca caatatatga taataacaag cactttggtg     60
ctcaccataa tatggtccat cttaccatca tcgctgggtg aggctgcacc aaagcagttt    120
atcaacacgc tattggacat cttcccacaa agaagatgga ttattacctt ggagagcata    180
atgctgatgg gcatgctatg cacatacatc ggccttctga tgtacaatga agatacatta    240
acaccgccgc tagattctct atctacagta acggatgccg gtggtcaact tgtaatagag    300
gacgaccccgg acgtattcgt taagaaatgg gcctttaaag aaacaagtgg tatttacgat    360
ctgtctctga tggatgcctg ccaacttctc tacctatatg ataacgacca taccagcaca    420
tag                                                                  423

<210> SEQ ID NO 27
<211> LENGTH: 140
<212> TYPE: PRT
<213> ORGANISM: Saccharomyces cerevisiae

<400> SEQUENCE: 27

Met Tyr Thr Lys Glu Tyr Tyr Trp Phe Ser Gln Tyr Met Ile Ile Thr
 1               5                  10                  15
Ser Thr Leu Val Leu Thr Ile Ile Trp Ser Ile Leu Pro Ser Ser Leu
            20                  25                  30
```

Gly Glu Ala Ala Pro Lys Gln Phe Ile Asn Thr Leu Leu Asp Ile Phe
                35                  40                  45

Pro Gln Arg Arg Trp Ile Ile Thr Leu Glu Ser Ile Met Leu Met Gly
 50                  55                  60

Met Leu Cys Thr Tyr Ile Gly Leu Leu Met Tyr Asn Glu Asp Thr Leu
 65                  70                  75                  80

Thr Pro Pro Leu Asp Ser Leu Ser Thr Val Thr Asp Ala Gly Gly Gln
                85                  90                  95

Leu Val Ile Glu Asp Asp Pro Asp Val Phe Val Lys Lys Trp Ala Phe
                100                 105                 110

Lys Glu Thr Ser Gly Ile Tyr Asp Leu Ser Leu Met Asp Ala Cys Gln
                115                 120                 125

Leu Leu Tyr Leu Tyr Asp Asn Asp His Thr Ser Thr
130                 135                 140

<210> SEQ ID NO 28
<211> LENGTH: 915
<212> TYPE: DNA
<213> ORGANISM: Saccharomyces cerevisiae

<400> SEQUENCE: 28

```
atgaagatgt tgaggcgtac aaaggtaaat ttttcaaaat tgctttacaa gattactaaa    60
ctagcaatag tactgacgat cctatatatt tattttacgc ccaaaatcgt ctcccgaaac   120
aatgcatcat tgcagcatat ttttcctcat aaatatggcg attatgaaat caatttggtc   180
atagcgcacc ctgacgacga agttatgttt ttttccccca taatttctca actgaattcg   240
tactttccga gaaccgtccc atttaacata atctgcttat caagggcaa cgccgaaggt   300
cttggcgaaa ccagggtaag agaattaaat gagtcggccg cttttattgct acacaatgaa   360
agagcagtct ccgtacaggt gatggatttc caggatggta tggacgaaat atgggatatt   420
gattctataa cttcttctct ttcacaaaag atagatataa agaatcataa cttgaaccag   480
attatcgtta cctttgattc atatggtgta tcaaatcata tcaaccacaa aagctgttat   540
gctgccgtta aaaagttggt ggatgattat gctcaaccta agaccaaaag aaatgaacaa   600
ccacctcatg tcactgcgct ttatttgaga agctacaaga caacatcgt tttaaagtac   660
aactccttta tttgggaaat cctaaaaata ctttacgacc tgatttctcc attccgtaga   720
ataattcagg cgcttccgcc taacacagcc gccgaaaaag acaagctttc acttatgaat   780
acacatgcac aatacgtact agcgtttgcc actatgctaa atgctcacga atcccaagtt   840
gtgtggttta gatacggatg gtggatattt tccagatttg tcttcgttaa tgaatttgat   900
gtttatacat attag                                                    915
```

<210> SEQ ID NO 29
<211> LENGTH: 304
<212> TYPE: PRT
<213> ORGANISM: Saccharomyces cerevisiae

<400> SEQUENCE: 29

Met Lys Met Leu Arg Arg Thr Lys Val Asn Phe Ser Lys Leu Leu Tyr
  1               5                  10                  15

Lys Ile Thr Lys Leu Ala Ile Val Leu Thr Ile Leu Tyr Ile Tyr Phe
                20                  25                  30

Thr Pro Lys Ile Val Ser Arg Asn Asn Ala Ser Leu Gln His Ile Phe
                35                  40                  45

Pro His Lys Tyr Gly Asp Tyr Glu Ile Asn Leu Val Ile Ala His Pro
 50                  55                  60

Asp Asp Glu Val Met Phe Phe Ser Pro Ile Ile Ser Gln Leu Asn Ser
 65                  70                  75                  80

Tyr Phe Pro Arg Thr Val Pro Phe Asn Ile Ile Cys Leu Ser Lys Gly
             85                  90                  95

Asn Ala Glu Gly Leu Gly Glu Thr Arg Val Arg Glu Leu Asn Glu Ser
        100                 105                 110

Ala Ala Leu Leu Leu His Asn Glu Arg Ala Val Ser Val Gln Val Met
    115                 120                 125

Asp Phe Gln Asp Gly Met Asp Glu Ile Trp Asp Ile Asp Ser Ile Thr
130                 135                 140

Ser Ser Leu Ser Gln Lys Ile Asp Ile Lys Asn His Asn Leu Asn Gln
145                 150                 155                 160

Ile Ile Val Thr Phe Asp Ser Tyr Gly Val Ser Asn His Ile Asn His
                165                 170                 175

Lys Ser Cys Tyr Ala Ala Val Lys Lys Leu Val Asp Asp Tyr Ala Gln
            180                 185                 190

Pro Lys Thr Lys Arg Asn Glu Gln Pro Pro His Val Thr Ala Leu Tyr
        195                 200                 205

Leu Arg Ser Tyr Lys Asn Asn Ile Val Leu Lys Tyr Asn Ser Phe Ile
    210                 215                 220

Trp Glu Ile Leu Lys Ile Leu Tyr Asp Leu Ile Ser Pro Phe Arg Arg
225                 230                 235                 240

Ile Ile Gln Ala Leu Pro Pro Asn Thr Ala Ala Glu Lys Asp Lys Leu
                245                 250                 255

Ser Leu Met Asn Thr His Ala Gln Tyr Val Leu Ala Phe Ala Thr Met
            260                 265                 270

Leu Asn Ala His Glu Ser Gln Val Val Trp Phe Arg Tyr Gly Trp Trp
        275                 280                 285

Ile Phe Ser Arg Phe Val Phe Val Asn Glu Phe Asp Val Tyr Thr Tyr
    290                 295                 300

<210> SEQ ID NO 30
<211> LENGTH: 2760
<212> TYPE: DNA
<213> ORGANISM: Saccharomyces cerevisiae

<400> SEQUENCE: 30
atgtggaaca aaaccagaac gacgcttctg gctgttggtg tcttatttca tttattttac        60
ctatggtcta tttttgatat ctatttcatt tcaccgctcg ttcatggtat gagcccatat       120
caaagtactc caacccctcc tgcaaagaga ttgttttttga ttgtcggtga tggtttacgt      180
gcagatacca cttttgataa agtcactcat ccagtatccg gaaaaacaga atttctggca       240
ccttttatta gatctttggt aatgaataat gccacctacg gtatatcaca taccagaatg      300
ccaactgaat cccgtcctgg tcatgttgct atgattgctg ggttttacga agatgttagt       360
gccgtcacaa aaggttggaa gtcaaaccct gtcaatttcg atagtttttt caaccaatct      420
actcatactt attcattcgg ttcacctgac attttaccta tgttcaaaga tggcgcttct      480
gacccaaata aagttgacac ttggatgtat gatcatactt tcgaggattt tacgcaatct      540
tccatcgagc tggatgcttt tgtctttaga cacttggatc aattattcca caattccaca      600
ctgaactcaa cattggatta tgaaattagg caagacggta atgtattctt tctacatcta      660
ctaggttgcg atactgccgg acattcttat agaccatatt ctgccgagta ttatgacaat      720
gtcaaatata ttgatgatca aatccctatc cttatagaca aagtcaacaa gttttttgcg       780

```
gacgacaaaa ccgcatttat ttttacagca gatcatggta tgagtgcatt tggatcacat      840
ggtgacggtc atcctaacaa cacaaggacc cctcttgttg cttggggtgc gggtttgaat      900
aaaccagtac ataatccttt tccggtatcc gacaactata ctgaaaattg ggagctttcg      960
agcattaaaa gaaatgatgt caagcaagca gatattgctt ctttaatgtc atacttgatt     1020
ggtgtgaact atcctaaaaa ttcagttggt gagttaccaa tagcatatat cgatggaaaa     1080
gaaagtgaca agcttgccgc attgtacaac aacgcaagaa gcattttaga gcagtactta     1140
gtcaagcaag atgaggtaat agactctcaa ttttttttata aggaatactt caagtttgtt     1200
gaaaagtctc attcacatta cttagaagag atagaaacct taattcagcg tatatctgaa     1260
ggagaaaact atttggaaca agaagcaatc acccttacag aggaattaat gcagataaca     1320
ttggaaggtt tacattattt gacaacctat aattggagat cattagaac tattgttaca     1380 tttgggtttg ttgggtggat ctttttttct tttataatat ttttgaaatc attcatatta     1440
gagaatgtaa ttgatgacca aaaagcgtca ccattaagcc atgcagtatt tggttccata     1500
ggaattttac taaattggat tttgttctac caacattctc cgttcaattt ttacatgtac     1560
cttcttttcc cattatactt ttggagctat atttttacaa atagatccgt actacgttca     1620
ggtatcaagg aattcttcaa aggtacctct ccttggaaaa gagttttaat aacaatctct     1680
attatatcag tttatgaggg aattgtatat ggattttcc atagatggac gtttacgcta     1740
attacaaata tattggcgtt ttacccgttt atttgtgggg tgagagagct atccgtgaat     1800
atattgtgga tcataactag tgttctttta tctacattta ccttatttga cgctgttaaa     1860
attgaggact tgaaccagat acatctagca gggttattaa tcattctcag tgccttttat     1920
gctctttaca aaatacattc caggataaat tcctacacgc gtgctatatt tgccattcaa     1980
atttccttgg tggctgccat gttggcggtt actcatcgtt cagttatctc tttacagcta     2040
agacaagggt taccaagaga gtcacaggtc gctggatgga taattttttt tgtatctctt     2100
tttgtaatgc caattttaca ttataggaag cccaacaatg attacaaagt gagattattg     2160
atcatttatt taaccttcgc accatccttt atcattttga ctatatcatt cgaatccctt     2220
ttctacttct tgttcactag ttacatggta caatggattg aaattgagaa caaaatcaaa     2280
gaaatgaaga cccaaaaaga tgaaaattgg ttacaagtgc taagagtttc agtaatcggg     2340 ttcttttttac ttcaagtcgc attctttgga actggtaacg tcgcttcaat ctcttcattt     2400
tcattggagt ctgtttgtag attgttgcca atttttgatc ctttcctgat gggcgcatta     2460
ttgatgttga aattgataat tccctacggg ctattgtcca catgcctagg tatactgaat     2520
ttaaaactta acttcaagga ctacacaatc tcatcattaa ttatttccat gagtgatatt     2580
ctgtcgttga atttttctcta cctttttaaga acggaggggt cgtggttgga tattggcata     2640
accatttcca actattgttt ggcgatccta tcatctttgt tcatgcttat tttggaagta     2700
ctcggtcatg tgttgctaaa aaatgtcatc atacaggata aaccaaaaa aacacaatag    2760
```

<210> SEQ ID NO 31
<211> LENGTH: 919
<212> TYPE: PRT
<213> ORGANISM: Saccharomyces cerevisiae

<400> SEQUENCE: 31

Met Trp Asn Lys Thr Arg Thr Thr Leu Leu Ala Val Gly Val Leu Phe
 1               5                  10                  15

His Leu Phe Tyr Leu Trp Ser Ile Phe Asp Ile Tyr Phe Ile Ser Pro
             20                  25                  30

-continued

```
Leu Val His Gly Met Ser Pro Tyr Gln Ser Thr Pro Thr Pro Pro Ala
         35                  40                  45
Lys Arg Leu Phe Leu Ile Val Gly Asp Gly Leu Arg Ala Asp Thr Thr
 50                  55                  60
Phe Asp Lys Val Thr His Pro Val Ser Gly Lys Thr Glu Phe Leu Ala
 65                  70                  75                  80
Pro Phe Ile Arg Ser Leu Val Met Asn Asn Ala Thr Tyr Gly Ile Ser
                 85                  90                  95
His Thr Arg Met Pro Thr Glu Ser Arg Pro Gly His Val Ala Met Ile
             100                 105                 110
Ala Gly Phe Tyr Glu Asp Val Ser Ala Val Thr Lys Gly Trp Lys Ser
             115                 120                 125
Asn Pro Val Asn Phe Asp Ser Phe Phe Asn Gln Ser Thr His Thr Tyr
130                 135                 140
Ser Phe Gly Ser Pro Asp Ile Leu Pro Met Phe Lys Asp Gly Ala Ser
145                 150                 155                 160
Asp Pro Asn Lys Val Asp Thr Trp Met Tyr Asp His Thr Phe Glu Asp
                165                 170                 175
Phe Thr Gln Ser Ser Ile Glu Leu Asp Ala Phe Val Phe Arg His Leu
             180                 185                 190
Asp Gln Leu Phe His Asn Ser Thr Leu Asn Ser Thr Leu Asp Tyr Glu
         195                 200                 205
Ile Arg Gln Asp Gly Asn Val Phe Leu His Leu Leu Gly Cys Asp
 210                 215                 220
Thr Ala Gly His Ser Tyr Arg Pro Tyr Ser Ala Glu Tyr Tyr Asp Asn
225                 230                 235                 240
Val Lys Tyr Ile Asp Asp Gln Ile Pro Ile Leu Ile Asp Lys Val Asn
                245                 250                 255
Lys Phe Phe Ala Asp Asp Lys Thr Ala Phe Ile Phe Thr Ala Asp His
             260                 265                 270
Gly Met Ser Ala Phe Gly Ser His Gly Asp Gly His Pro Asn Asn Thr
             275                 280                 285
Arg Thr Pro Leu Val Ala Trp Gly Ala Gly Leu Asn Lys Pro Val His
290                 295                 300
Asn Pro Phe Pro Val Ser Asp Asn Tyr Thr Glu Asn Trp Glu Leu Ser
305                 310                 315                 320
Ser Ile Lys Arg Asn Asp Val Lys Gln Ala Asp Ile Ala Ser Leu Met
                325                 330                 335
Ser Tyr Leu Ile Gly Val Asn Tyr Pro Lys Asn Ser Val Gly Glu Leu
             340                 345                 350
Pro Ile Ala Tyr Ile Asp Gly Lys Glu Ser Asp Lys Leu Ala Ala Leu
             355                 360                 365
Tyr Asn Asn Ala Arg Ser Ile Leu Glu Gln Tyr Leu Val Lys Gln Asp
370                 375                 380
Glu Val Ile Asp Ser Gln Phe Phe Tyr Lys Glu Tyr Phe Lys Phe Val
385                 390                 395                 400
Glu Lys Ser His Ser His Tyr Leu Glu Glu Ile Glu Thr Leu Ile Gln
                405                 410                 415
Arg Ile Ser Glu Gly Glu Asn Tyr Leu Glu Gln Glu Ala Ile Thr Leu
             420                 425                 430
Thr Glu Glu Leu Met Gln Ile Thr Leu Glu Gly Leu His Tyr Leu Thr
             435                 440                 445
Thr Tyr Asn Trp Arg Phe Ile Arg Thr Ile Val Thr Phe Gly Phe Val
450                 455                 460
```

```
Gly Trp Ile Phe Phe Ser Phe Ile Ile Phe Leu Lys Ser Phe Ile Leu
465                 470                 475                 480

Glu Asn Val Ile Asp Asp Gln Lys Ala Ser Pro Leu Ser His Ala Val
                485                 490                 495

Phe Gly Ser Ile Gly Ile Leu Leu Asn Trp Ile Leu Phe Tyr Gln His
            500                 505                 510

Ser Pro Phe Asn Phe Tyr Met Tyr Leu Leu Phe Pro Leu Tyr Phe Trp
            515                 520                 525

Ser Tyr Ile Phe Thr Asn Arg Ser Val Leu Arg Ser Gly Ile Lys Glu
        530                 535                 540

Phe Phe Lys Gly Thr Ser Pro Trp Lys Arg Val Leu Ile Thr Ile Ser
545                 550                 555                 560

Ile Ile Ser Val Tyr Glu Gly Ile Val Tyr Gly Phe Phe His Arg Trp
                565                 570                 575

Thr Phe Thr Leu Ile Thr Asn Ile Leu Ala Phe Tyr Pro Phe Ile Cys
            580                 585                 590

Gly Val Arg Glu Leu Ser Val Asn Ile Leu Trp Ile Ile Thr Ser Val
        595                 600                 605

Leu Leu Ser Thr Phe Thr Leu Phe Asp Ala Val Lys Ile Glu Asp Leu
            610                 615                 620

Asn Gln Ile His Leu Ala Gly Leu Leu Ile Ile Leu Ser Ala Phe Tyr
625                 630                 635                 640

Ala Leu Tyr Lys Ile His Ser Arg Ile Asn Ser Tyr Thr Arg Ala Ile
                645                 650                 655

Phe Ala Ile Gln Ile Ser Leu Val Ala Ala Met Leu Ala Val Thr His
            660                 665                 670

Arg Ser Val Ile Ser Leu Gln Leu Arg Gln Gly Leu Pro Arg Glu Ser
        675                 680                 685

Gln Val Ala Gly Trp Ile Ile Phe Phe Val Ser Leu Phe Val Met Pro
            690                 695                 700

Ile Leu His Tyr Arg Lys Pro Asn Asn Asp Tyr Lys Val Arg Leu Leu
705                 710                 715                 720

Ile Ile Tyr Leu Thr Phe Ala Pro Ser Phe Ile Ile Leu Thr Ile Ser
                725                 730                 735

Phe Glu Ser Leu Phe Tyr Phe Leu Phe Thr Ser Tyr Met Val Gln Trp
            740                 745                 750

Ile Glu Ile Glu Asn Lys Ile Lys Glu Met Lys Thr Gln Lys Asp Glu
        755                 760                 765

Asn Trp Leu Gln Val Leu Arg Val Ser Val Ile Gly Phe Phe Leu Leu
            770                 775                 780

Gln Val Ala Phe Phe Gly Thr Gly Asn Val Ala Ser Ile Ser Ser Phe
785                 790                 795                 800

Ser Leu Glu Ser Val Cys Arg Leu Leu Pro Ile Phe Asp Pro Phe Leu
                805                 810                 815

Met Gly Ala Leu Leu Met Leu Lys Leu Ile Pro Tyr Gly Leu Leu
            820                 825                 830

Ser Thr Cys Leu Gly Ile Leu Asn Leu Lys Leu Asn Phe Lys Asp Tyr
        835                 840                 845

Thr Ile Ser Ser Leu Ile Ile Ser Met Ser Asp Ile Leu Ser Leu Asn
            850                 855                 860

Phe Phe Tyr Leu Leu Arg Thr Glu Gly Ser Trp Leu Asp Ile Gly Ile
865                 870                 875                 880

Thr Ile Ser Asn Tyr Cys Leu Ala Ile Leu Ser Ser Leu Phe Met Leu
```

```
                      885              890              895
Ile Leu Glu Val Leu Gly His Val Leu Leu Lys Asn Val Ile Ile Gln
                  900              905              910

Asp Lys Thr Lys Lys Thr Gln
            915

<210> SEQ ID NO 32
<211> LENGTH: 660
<212> TYPE: DNA
<213> ORGANISM: Saccharomyces cerevisiae

<400> SEQUENCE: 32
atgccagcta aaaaaggac tagaaagaca gtgaaaaaaa ccgtatcatt ctccgatgac      60
acaacattaa caacgcacca aaatcgtgag aaaaagaacg tagatcatga tcgtccacct     120
gtgtatgtga ggaaaacccc tctgatgaca tttccatacc atttagtagc actactttat    180
tactacgttt ttgtatcttc aaatttcaat acggtgaagt tgctaagttt tttgattcct    240
acacaagttg cttatttagt tttacaattc aataaatgca cagtttacgg taacaaaatc    300
attaagatca attactcatt gaccattatt tgtctaggtg ttacattttt gttgagcttt    360
cccacaatgt tattaactat attatttggt gcgccattaa tggacttatt gtgggaaacc    420
tggctgttgt cactgcattt tgcattttta gcatacctg cagtttattc tgtatttaat     480
tgtgatttca agtgggatt atggaagaag tatttatct ttatcgttgt aggggttgg      540 attagttgtg ttgtcattcc tttggattgg gatagagatt ggcagaattg gccaattcct    600
attgttgttg gaggttattt gggcgctttg gtgggctata ctatcggtgc ctatatataa    660

<210> SEQ ID NO 33
<211> LENGTH: 219
<212> TYPE: PRT
<213> ORGANISM: Saccharomyces cerevisiae

<400> SEQUENCE: 33

Met Pro Ala Lys Lys Arg Thr Arg Lys Thr Val Lys Lys Thr Val Ser
 1               5                  10                  15

Phe Ser Asp Asp Thr Thr Leu Thr Thr His Gln Asn Arg Glu Lys Lys
                20                  25                  30

Asn Val Asp His Asp Arg Pro Pro Val Tyr Val Arg Lys Thr Pro Leu
            35                  40                  45

Met Thr Phe Pro Tyr His Leu Val Ala Leu Leu Tyr Tyr Tyr Val Phe
        50                  55                  60

Val Ser Ser Asn Phe Asn Thr Val Lys Leu Leu Ser Phe Leu Ile Pro
65                  70                  75                  80

Thr Gln Val Ala Tyr Leu Val Leu Gln Phe Asn Lys Cys Thr Val Tyr
                85                  90                  95

Gly Asn Lys Ile Ile Lys Ile Asn Tyr Ser Leu Thr Ile Ile Cys Leu
            100                 105                 110

Gly Val Thr Phe Leu Leu Ser Phe Pro Thr Met Leu Leu Thr Ile Leu
        115                 120                 125

Phe Gly Ala Pro Leu Met Asp Leu Leu Trp Glu Thr Trp Leu Leu Ser
    130                 135                 140

Leu His Phe Ala Phe Leu Ala Tyr Pro Ala Val Tyr Ser Val Phe Asn
145                 150                 155                 160

Cys Asp Phe Lys Val Gly Leu Trp Lys Lys Tyr Phe Ile Phe Ile Val
                165                 170                 175

Val Gly Gly Trp Ile Ser Cys Val Val Ile Pro Leu Asp Trp Asp Arg
```

```
              180              185                  190
Asp Trp Gln Asn Trp Pro Ile Pro Ile Val Val Gly Gly Tyr Leu Gly
        195                 200                 205

Ala Leu Val Gly Tyr Thr Ile Gly Ala Tyr Ile
    210                 215
```

<210> SEQ ID NO 34
<211> LENGTH: 2493
<212> TYPE: DNA
<213> ORGANISM: Saccharomyces cerevisiae

<400> SEQUENCE: 34

| | | | | | |
|---|---|---|---|---|---|
| atgaacttga | agcagttcac | gtgcctatca | tgcgctcaat | tactcgctat | tctgctcttt | 60 |
| atctttgctt | ttttccctag | aaaaatcgtg | ctgacaggta | tatcaaagca | agatccggat | 120 |
| caagaccgtg | atctccagcg | cgataggccc | ttccagaaat | tggtgtttgt | gatcattgat | 180 |
| gctctcagat | cagactttct | ttttgattcg | cagatttccc | acttcaacaa | cgtgcaccaa | 240 |
| tggctcaata | cgggcgaagc | atggggttac | acgtcatttg | ctaatccgcc | taccgtgacg | 300 |
| ctgcctagac | tcaaaagtat | tactacggga | tctacaccta | gcttcattga | cttgctgctg | 360 |
| aatgtagccc | aggacataga | ttccaacgat | cttcggagc | acgattcctg | gctgcagcag | 420 |
| ttcatccaac | ataataacac | gattcgtttc | atgggcgatg | cacctggct | gaaactgttc | 480 |
| ccacagcaat | ggtttgactt | cgctgacccg | acacactcgt | tctttgtcag | tgatttcact | 540 |
| caagtcgata | taatgtgac | gaggaacttg | cccgggaaat | tatttcagga | atgggcccag | 600 |
| tgggacgtgg | ctatcctgca | ttacttgggt | cttgaccata | tcgggcataa | agatggcccg | 660 |
| cattcaaagt | ttatggctgc | taaacatcaa | gaaatggaca | gcattctgaa | gtcaatatat | 720 |
| gatgaagtgt | tggaacatga | agatgacgat | gatacactga | tttgtgttct | tggcgaccat | 780 |
| ggaatgaacg | aactgggcaa | ccatggtggc | tcttcagccg | gcgaaacatc | agcaggattg | 840 |
| ttgttttgt | cacctaagct | ggcgcaattt | gctaggccag | aatcgcaagt | aaactacaca | 900 |
| ttgcccatca | acgctagtcc | ggactggaat | ttccagtatt | tagagactgt | tcaacaaatt | 960 |
| gatatcgtcc | ccaccatagc | agcactgttt | ggtatgccaa | tccccatgaa | cagtgttggg | 1020 |
| ataataatac | ctgactttt | acaactgttg | cccaataagt | tggcaagtat | gaaagaaaat | 1080 |
| tttatgcatt | tgtggaaatt | atcagaccat | acgggcgagg | ttgctcttga | cgatttcact | 1140 |
| gccgaagata | tttatacaaa | gatgtacact | attcaagaaa | cgttaaccaa | gtctgcaaca | 1200 |
| aattataatt | atcctctttt | gacactggct | tttgttggtt | tcctcataat | aacaatcatc | 1260 |
| gccatttatg | tattattacg | ttattctggg | cctgattttt | ggcagttgcg | cgtttcttcc | 1320 |
| ctgtctgttc | tgttagtttc | cattatacta | ggcgtttcca | catttgcaag | tagtttcatt | 1380 |
| gaagaggagc | accaactgtg | gtggtggata | gtaactgcat | tctcggcggt | ccctctgttc | 1440 |
| gtataccgat | tgaatgtgct | cataatcgtg | cgctggttta | atgatggc | atgcgtacgc | 1500 |
| tcaatcaagt | tttggaataa | cagtggccag | aaattcattt | attctaacgt | tatgtccaat | 1560 |
| ctacttaatc | agaatccttc | ctggaagtgg | tgcttaaata | tgttgacatt | tctagtgctg | 1620 |
| ataatggcat | ctgctggttt | tcaagtacta | cattttattg | tcactactat | tttggtgggg | 1680 |
| ttgtgtttca | cgtacaaaat | ctcgtgggaa | atcgtcaatg | gtaaccaggc | agaaataccg | 1740 |
| ctctttatgc | atgatttact | ggctaagata | gactttgcac | caactgaaag | taacttgatt | 1800 |
| gtacttgcgc | gcgttttctt | ccaagcttgg | gctattgttg | tcatttcaag | gttggtcctg | 1860 |
| acgaaattga | aagtacttaa | caagaactac | ctcattaaag | atatgaaagt | ttatataaca | 1920 |

-continued

```
attcttttga tgttccaaac ttcttctcag aacataggtc aatttctcgt tttccaaata    1980
ttagagtccc aaattttta cttttccaa aatattccaa ccgcctcatt aacatcaaca    2040
agtaagattt attttcgaa tttggtgtcc ttaatttac aaaatttac attttccaa    2100 ttcggtggca caaattccat ttctactata gaccttggaa acgcatacca tggtgtttcc    2160
tcagactaca acatctacgt agtggggata ttaatgtccg ttgccaattt cgcgccggca    2220
atatactggt ccatgctacc gtggtcaata aactacgcct ctattccagc acaagttaag    2280
ttgcaaacgt tcatcagaag taagttacct gccttcacct atcattgtat atttggaact    2340
tgtttgatga cggcatgcgt cgttttgaga tttcatctct ttatttggtc cgttttcagt    2400
ccaaaattat gttattttct tgggtggaat tttgtgatgg gattgctgaa tggctggtta    2460
cctgaattgg ccctccttg cgctcttgat taa                                  2493
```

<210> SEQ ID NO 35
<211> LENGTH: 830
<212> TYPE: PRT
<213> ORGANISM: Saccharomyces cerevisiae

<400> SEQUENCE: 35

```
Met Asn Leu Lys Gln Phe Thr Cys Leu Ser Cys Ala Gln Leu Leu Ala
 1               5                   10                  15

Ile Leu Leu Phe Ile Phe Ala Phe Phe Pro Arg Lys Ile Val Leu Thr
            20                  25                  30

Gly Ile Ser Lys Gln Asp Pro Asp Gln Asp Arg Asp Leu Gln Arg Asp
        35                  40                  45

Arg Pro Phe Gln Lys Leu Val Phe Val Ile Ile Asp Ala Leu Arg Ser
    50                  55                  60

Asp Phe Leu Phe Asp Ser Gln Ile Ser His Phe Asn Asn Val His Gln
65                  70                  75                  80

Trp Leu Asn Thr Gly Glu Ala Trp Gly Tyr Thr Ser Phe Ala Asn Pro
                85                  90                  95

Pro Thr Val Thr Leu Pro Arg Leu Lys Ser Ile Thr Thr Gly Ser Thr
            100                 105                 110

Pro Ser Phe Ile Asp Leu Leu Leu Asn Val Ala Gln Asp Ile Asp Ser
        115                 120                 125

Asn Asp Leu Ser Glu His Asp Ser Trp Leu Gln Gln Phe Ile Gln His
    130                 135                 140

Asn Asn Thr Ile Arg Phe Met Gly Asp Asp Thr Trp Leu Lys Leu Phe
145                 150                 155                 160

Pro Gln Gln Trp Phe Asp Phe Ala Asp Pro Thr His Ser Phe Phe Val
                165                 170                 175

Ser Asp Phe Thr Gln Val Asp Asn Asn Val Thr Arg Asn Leu Pro Gly
            180                 185                 190

Lys Leu Phe Gln Glu Trp Ala Gln Trp Asp Val Ala Ile Leu His Tyr
        195                 200                 205

Leu Gly Leu Asp His Ile Gly His Lys Asp Gly Pro His Ser Lys Phe
    210                 215                 220

Met Ala Ala Lys His Gln Glu Met Asp Ser Ile Leu Lys Ser Ile Tyr
225                 230                 235                 240

Asp Glu Val Leu Glu His Glu Asp Asp Asp Thr Leu Ile Cys Val
                245                 250                 255

Leu Gly Asp His Gly Met Asn Glu Leu Gly Asn His Gly Gly Ser Ser
            260                 265                 270

Ala Gly Glu Thr Ser Ala Gly Leu Leu Phe Leu Ser Pro Lys Leu Ala
```

-continued

```
            275                 280                 285
Gln Phe Ala Arg Pro Glu Ser Gln Val Asn Tyr Thr Leu Pro Ile Asn
290                 295                 300
Ala Ser Pro Asp Trp Asn Phe Gln Tyr Leu Glu Thr Val Gln Gln Ile
305                 310                 315                 320
Asp Ile Val Pro Thr Ile Ala Ala Leu Phe Gly Met Pro Ile Pro Met
                    325                 330                 335
Asn Ser Val Gly Ile Ile Pro Asp Phe Leu Gln Leu Leu Pro Asn
                    340                 345                 350
Lys Leu Ala Ser Met Lys Glu Asn Phe Met His Leu Trp Lys Leu Ser
                    355                 360                 365
Asp His His Gly Glu Val Ala Leu Asp Asp Phe Thr Ala Glu Asp Ile
                    370                 375                 380
Tyr Thr Lys Met Tyr Thr Ile Gln Glu Thr Leu Thr Lys Ser Ala Thr
385                 390                 395                 400
Asn Tyr Asn Tyr Pro Leu Leu Thr Leu Ala Phe Val Gly Phe Leu Ile
                    405                 410                 415
Ile Thr Ile Ile Ala Ile Tyr Val Leu Leu Arg Tyr Ser Gly Pro Asp
                    420                 425                 430
Phe Trp Gln Leu Arg Val Ser Ser Leu Ser Val Leu Leu Val Ser Ile
                    435                 440                 445
Ile Leu Gly Val Ser Thr Phe Ala Ser Ser Phe Ile Glu Glu His
                    450                 455                 460
Gln Leu Trp Trp Trp Ile Val Thr Ala Phe Ser Ala Val Pro Leu Phe
465                 470                 475                 480
Val Tyr Arg Leu Asn Val Leu Ile Ile Val Arg Trp Phe Ile Met Met
                    485                 490                 495
Ala Cys Val Arg Ser Ile Lys Phe Trp Asn Asn Ser Gly Gln Lys Phe
                    500                 505                 510
Ile Tyr Ser Asn Val Met Ser Asn Leu Asn Gln Asn Pro Ser Trp
                    515                 520                 525
Lys Trp Cys Leu Asn Met Leu Thr Phe Leu Val Leu Ile Met Ala Ser
530                 535                 540
Ala Gly Phe Gln Val Leu His Phe Ile Val Thr Thr Ile Leu Val Gly
545                 550                 555                 560
Leu Cys Phe Thr Tyr Lys Ile Ser Trp Glu Ile Val Asn Gly Asn Gln
                    565                 570                 575
Ala Glu Ile Pro Leu Phe Met His Asp Leu Leu Ala Lys Ile Asp Phe
                    580                 585                 590
Ala Pro Thr Glu Ser Asn Leu Ile Val Leu Ala Arg Val Phe Phe Gln
                    595                 600                 605
Ala Trp Ala Ile Val Val Ile Ser Arg Leu Val Leu Thr Lys Leu Lys
                    610                 615                 620
Val Leu Asn Lys Asn Tyr Leu Ile Lys Asp Met Lys Val Tyr Ile Thr
625                 630                 635                 640
Ile Leu Leu Met Phe Gln Thr Ser Ser Gln Asn Ile Gly Gln Phe Leu
                    645                 650                 655
Val Phe Gln Ile Leu Glu Ser Gln Ile Phe Tyr Phe Gln Asn Ile
                    660                 665                 670
Pro Thr Ala Ser Leu Thr Ser Thr Ser Lys Ile Tyr Phe Ser Asn Leu
                    675                 680                 685
Val Ser Leu Ile Leu Gln Asn Phe Thr Phe Phe Gln Phe Gly Gly Thr
                    690                 695                 700
```

```
Asn Ser Ile Ser Thr Ile Asp Leu Gly Asn Ala Tyr His Gly Val Ser
705                 710                 715                 720

Ser Asp Tyr Asn Ile Tyr Val Val Gly Ile Leu Met Ser Val Ala Asn
            725                 730                 735

Phe Ala Pro Ala Ile Tyr Trp Ser Met Leu Pro Trp Ser Ile Asn Tyr
        740                 745                 750

Ala Ser Ile Pro Ala Gln Val Lys Leu Gln Thr Phe Ile Arg Ser Lys
            755                 760                 765

Leu Pro Ala Phe Thr Tyr His Cys Ile Phe Gly Thr Cys Leu Met Thr
        770                 775                 780

Ala Cys Val Val Leu Arg Phe His Leu Phe Ile Trp Ser Val Phe Ser
785                 790                 795                 800

Pro Lys Leu Cys Tyr Phe Leu Gly Trp Asn Phe Val Met Gly Leu Leu
            805                 810                 815

Asn Gly Trp Leu Pro Glu Leu Ala Leu Leu Cys Ala Leu Asp
            820                 825                 830

<210> SEQ ID NO 36
<211> LENGTH: 1605
<212> TYPE: DNA
<213> ORGANISM: Saccharomyces cerevisiae

<400> SEQUENCE: 36
atgtccaatg caaatctaag aaaatgggtt ggttttgct ttgttgccat ttatctcttt      60
ttaggtgttc cactgtggta caagctaact acagtttata gagcatcact accaataaat    120
tacattgagt cacttcaaaa taacaaattc aagatattc atctcgtaat accggtgtat    180
gttaagtcag atacttacag atttcctgac gttcatgacg ctatccaagt acaagttaac    240
catttattga attctcagga gcaacgggtc ccttggtctt tacaagttct tccatataat    300
gagactattg agcagatgga aagtgaaggc aaccagtttc atgtcgttac tttgaagtta    360
gacgaattta ttggttactc atcagcttac gacaccaaag aaacactagt atattacgac    420
gatgctgccg ttttaagtaa tgatctaccg ttttttgttg ctcaaacatt ggtagagcac    480
actttccaat tggaatggac gcatttgaat aaaacgtgtg aaggcgtttc tacaaacaac    540
gatgtcgcaa tatcttatga tccaaacatt catttaagtg taactttatt gtcaggtgat    600
gggaatcctg ttgcatggga aattgagcct acattaactg actacttttc accttttagg    660
aagttcttat caccactggt aaattttaca gtagattcat ccattgttta tcataatgat    720
ttgaatttgc attcattaaa tggatcatgt acaagcgtta cgtggtttga tctctctcat    780
actattgatc tttctgaact ttcttcaatg gcctattacc agaagattc tgcactgaat    840 ttagccatag tctttcctag tgcttcttca agtcccgatg gtctggcgtt cattaatggc    900
actcggattt cagacgaaat aaccacatta gattggaata gttatctagt tcctcaatgg    960
ggggttataa taataaataa aatgccgttg aagccaaatt cagtcattag cgaagattat   1020
ttagaaccta tgatgtaccg ttttgcgaca gatatttttc aactattggg attaacggag   1080
ggctcgcaag atttgttatc accttatatt accatagatt cattcaaaag gttgacaatt   1140
ttacagaatc tagataaagc tacggaaaca ttatggtcgt tagtgaaatt aactcaacaa   1200
tttcagggca tgtctatccc acgcgaagta tcggataatg ttatcgaagc tttagactta   1260
aggctacaga ttattgattt attaaatgat cctggaaagg gtggagatat cgtctggaac   1320
aatgccctgc atctaagtaa tgaattggtt aaactatgcg aaaaggcatt tttcaatgga   1380
gaaatggttc aacaaaattt cttcccacaa gagcacatga tagctgtgta tttaccttta   1440
```

-continued

```
ttaggcccaa tatcggcagt catgttcttt ggtttctaca acgtgatgaa ggaaaagaat    1500
caaaagagta aaagaatgg  aaccgagaga gaagttgcta aagaaaaatt agagttgaaa    1560
gaggctcaaa aattacatgc tattgatggt gaagatgaat tatga                   1605
```

```
<210> SEQ ID NO 37
<211> LENGTH: 534
<212> TYPE: PRT
<213> ORGANISM: Saccharomyces cerevisiae

<400> SEQUENCE: 37
```

| | | | | | | | | | | | | | | | |
|---|---|---|---|---|---|---|---|---|---|---|---|---|---|---|---|
| Met | Ser | Asn | Ala | Asn | Leu | Arg | Lys | Trp | Val | Gly | Phe | Cys | Phe | Val | Ala |
| 1 | | | | 5 | | | | | 10 | | | | | 15 | |
| Ile | Tyr | Leu | Phe | Leu | Gly | Val | Pro | Leu | Trp | Tyr | Lys | Leu | Thr | Thr | Val |
| | | | 20 | | | | | 25 | | | | | 30 | | |
| Tyr | Arg | Ala | Ser | Leu | Pro | Ile | Asn | Tyr | Ile | Glu | Ser | Leu | Gln | Asn | Asn |
| | | 35 | | | | | 40 | | | | | 45 | | | |
| Lys | Phe | Gln | Asp | Ile | His | Leu | Val | Ile | Pro | Val | Tyr | Val | Lys | Ser | Asp |
| | 50 | | | | | 55 | | | | | 60 | | | | |
| Thr | Tyr | Arg | Phe | Pro | Asp | Val | His | Asp | Ala | Ile | Gln | Val | Gln | Val | Asn |
| 65 | | | | | 70 | | | | | 75 | | | | | 80 |
| His | Leu | Leu | Asn | Ser | Gln | Glu | Gln | Arg | Val | Pro | Trp | Ser | Leu | Gln | Val |
| | | | | 85 | | | | | 90 | | | | | 95 | |
| Leu | Pro | Tyr | Asn | Glu | Thr | Ile | Glu | Gln | Met | Glu | Ser | Glu | Gly | Asn | Gln |
| | | | 100 | | | | | 105 | | | | | 110 | | |
| Phe | His | Val | Val | Thr | Leu | Lys | Leu | Asp | Glu | Phe | Ile | Gly | Tyr | Ser | Ser |
| | | 115 | | | | | 120 | | | | | 125 | | | |
| Ala | Tyr | Asp | Thr | Lys | Glu | Thr | Leu | Val | Tyr | Tyr | Asp | Asp | Ala | Ala | Val |
| | 130 | | | | | 135 | | | | | 140 | | | | |
| Leu | Ser | Asn | Asp | Leu | Pro | Phe | Phe | Val | Ala | Gln | Thr | Leu | Val | Glu | His |
| 145 | | | | | 150 | | | | | 155 | | | | | 160 |
| Thr | Phe | Gln | Leu | Glu | Trp | Thr | His | Leu | Asn | Lys | Thr | Cys | Glu | Gly | Val |
| | | | | 165 | | | | | 170 | | | | | 175 | |
| Ser | Thr | Asn | Asn | Asp | Val | Ala | Ile | Ser | Tyr | Asp | Pro | Asn | Ile | His | Leu |
| | | | 180 | | | | | 185 | | | | | 190 | | |
| Ser | Val | Thr | Leu | Leu | Ser | Gly | Asp | Gly | Asn | Pro | Val | Ala | Trp | Glu | Ile |
| | | 195 | | | | | 200 | | | | | 205 | | | |
| Glu | Pro | Thr | Leu | Thr | Asp | Tyr | Phe | Ser | Pro | Phe | Arg | Lys | Phe | Leu | Ser |
| | 210 | | | | | 215 | | | | | 220 | | | | |
| Pro | Leu | Val | Asn | Phe | Thr | Val | Asp | Ser | Ser | Ile | Val | Tyr | His | Asn | Asp |
| 225 | | | | | 230 | | | | | 235 | | | | | 240 |
| Leu | Asn | Leu | His | Ser | Leu | Asn | Gly | Ser | Cys | Thr | Ser | Val | Thr | Trp | Phe |
| | | | | 245 | | | | | 250 | | | | | 255 | |
| Asp | Leu | Ser | His | Thr | Ile | Asp | Leu | Ser | Glu | Leu | Ser | Ser | Met | Ala | Tyr |
| | | | 260 | | | | | 265 | | | | | 270 | | |
| Tyr | Pro | Glu | Asp | Ser | Ala | Leu | Asn | Leu | Ala | Ile | Val | Phe | Pro | Ser | Ala |
| | | 275 | | | | | 280 | | | | | 285 | | | |
| Ser | Ser | Ser | Pro | Asp | Gly | Leu | Ala | Phe | Ile | Asn | Gly | Thr | Arg | Ile | Ser |
| | 290 | | | | | 295 | | | | | 300 | | | | |
| Asp | Glu | Ile | Thr | Thr | Leu | Asp | Trp | Asn | Ser | Tyr | Leu | Val | Pro | Gln | Trp |
| 305 | | | | | 310 | | | | | 315 | | | | | 320 |
| Gly | Val | Ile | Ile | Ile | Asn | Lys | Met | Pro | Leu | Lys | Pro | Asn | Ser | Val | Ile |
| | | | | 325 | | | | | 330 | | | | | 335 | |
| Ser | Glu | Asp | Tyr | Leu | Glu | Pro | Met | Met | Tyr | Arg | Phe | Ala | Thr | Asp | Ile |
| | | | 340 | | | | | 345 | | | | | 350 | | |

```
Phe Gln Leu Leu Gly Leu Thr Glu Gly Ser Gln Asp Leu Leu Ser Pro
            355                 360                 365
Tyr Ile Thr Ile Asp Ser Phe Lys Arg Leu Thr Ile Leu Gln Asn Leu
        370                 375                 380
Asp Lys Ala Thr Glu Thr Leu Trp Ser Leu Val Lys Leu Thr Gln Gln
385                 390                 395                 400
Phe Gln Gly Met Ser Ile Pro Arg Glu Val Ser Asp Asn Val Ile Glu
                405                 410                 415
Ala Leu Asp Leu Arg Leu Gln Ile Ile Asp Leu Leu Asn Asp Pro Gly
            420                 425                 430
Lys Gly Gly Asp Ile Val Trp Asn Asn Ala Leu His Leu Ser Asn Glu
        435                 440                 445
Leu Val Lys Leu Cys Glu Lys Ala Phe Phe Asn Gly Glu Met Val Gln
450                 455                 460
Gln Asn Phe Phe Pro Gln Glu His Met Ile Ala Val Tyr Leu Pro Leu
465                 470                 475                 480
Leu Gly Pro Ile Ser Ala Val Met Phe Phe Gly Phe Tyr Asn Val Met
                485                 490                 495
Lys Glu Lys Asn Gln Lys Ser Lys Asn Gly Thr Glu Arg Glu Val
            500                 505                 510
Ala Lys Glu Lys Leu Glu Leu Lys Glu Ala Gln Lys Leu His Ala Ile
        515                 520                 525
Asp Gly Glu Asp Glu Leu
        530
```

<210> SEQ ID NO 38
<211> LENGTH: 1833
<212> TYPE: DNA
<213> ORGANISM: Saccharomyces cerevisiae

<400> SEQUENCE: 38

```
atgatcctca cactggccta tttcatgctg ggcactctac tactgggtgt gttcgcagaa     60
gacacggtgt cgcagattgg tataaatgac agtttatggt atccgtacga cgaagcactg    120
gtgttgaagc cgctgcccaa caatgatctg ctactctcat ttgcattcca actgcaatcg    180
gaaccgtttg acccggccgt atcatccatg tcatatgatg cgtatgagca ctacacgact    240
ttcccacggg ccatcccacc attgttggaa tctactgcca cgcgtcagtt tcatttaaga    300
tttaccagag gattctggga tgccctgtcg tggggacagt tgccacatgc tggaaaagag    360
gcaggtgcct caggtgtgga attgtggtcg caagtgcagg ccatggatca ggaacaggcg    420
ttccataatt ggaaaaaact gtccaattca ttgagcggat tgttttgttc ttctttaaat    480
tttatcgacg agtcaaggac gacctttccc cggcggtcat atgcttctga tataggagct    540
cctcttttca atagcaccga gaactgtac ctgatgcgag catcgttgcc caatgaaccc    600
atctgtaccg agaacttgac gccgttcata aaactattgc ctactagggg caaatccggt    660
ttgacatctc tcttggatgg tcataaattg ttcgactctc tatggaatag tatttccttg    720
gatattgcca ctatttgttc tgaagatgaa gatgctcttt gtcactacga gatggacgca    780
cgcatagaaa tggtaacaca cgttccctcc gccttggcaa gaggtgagag acctatcccc    840
aaacctttgg atgggaacac attgcgttgt gacacggata aacccttga ttcttaccaa    900
tgcttccctc taccggaacc ttcgcagact cacttcaagc tgtctcagct gtttgccaga    960
ccaataaaca atggcaacct gtttgctaat aggcccacaa gaatttgtgc agaagttgac   1020
cgttctacct ggactgcgtt tttgtcagtt gacgatacta ttttcagcac acatgataat   1080
```

-continued

```
tgctttgact tatcaaacga tcaaaatgag ggtggttcgg gctacgactt tattttagaa    1140
tcgacggaca ctactaaagt tactcccata gttcctgtcc caattcacgt aagcagatct    1200
ctgactggta atggacaaga tcgtggtgga atgcgtattg ttttccataa cgacaatgat    1260 accctgtga agttgattta tttcgaatca ttgccatggt tcatgagagt ttacctatcc     1320
tctcttcaaa ttacttctac tacctctccg caattgcaag aaaacgatat catcttagat    1380
aaatactatt tacaagcggc cgatagaaaa agacctggcc acttggagtt cacgatgtta    1440
attccagcta atacggacat tgtaatgact tatcaattcg ataaagctct tctgcaattt    1500
gccgagtatc caccagatgc aaaccatggt tttgaaatcg atgcagctgt aatcaccgtg    1560
ctatctttgg agtcctcatc gtctctttat gaaatgagaa cctctaccct attgttatcc    1620
ctgtctacac cggattttag tatgccgtat aacgtcatca ttctaacatc tacaatcatg    1680
ggactcatat tcggtatgct atacaatttg atggtgaaga gaatggtcac cgtcgaagag    1740
gccgataaga ttacgttgca atctggctta aaatacaaat tgctaaagct aaaggaaaag    1800
ttcctaggga aaaaaagac taaaacagac taa                                  1833
```

<210> SEQ ID NO 39
<211> LENGTH: 610
<212> TYPE: PRT
<213> ORGANISM: Saccharomyces cerevisiae

<400> SEQUENCE: 39

```
Met Ile Leu Thr Leu Ala Tyr Phe Met Leu Gly Thr Leu Leu Leu Gly
  1               5                  10                  15

Val Phe Ala Glu Asp Thr Val Ser Gln Ile Gly Ile Asn Asp Ser Leu
             20                  25                  30

Trp Tyr Pro Tyr Asp Glu Ala Leu Val Leu Lys Pro Leu Pro Asn Asn
         35                  40                  45

Asp Leu Leu Ser Phe Ala Phe Gln Leu Gln Ser Glu Pro Phe Asp
     50                  55                  60

Pro Ala Val Ser Ser Met Ser Tyr Asp Ala Tyr Glu His Tyr Thr Thr
 65                  70                  75                  80

Phe Pro Arg Ala Ile Pro Pro Leu Leu Glu Ser Thr Ala Thr Arg Gln
                 85                  90                  95

Phe His Leu Arg Phe Thr Arg Gly Phe Trp Asp Ala Leu Ser Trp Gly
            100                 105                 110

Gln Leu Pro His Ala Gly Lys Glu Ala Gly Ala Ser Gly Val Glu Leu
        115                 120                 125

Trp Ser Gln Val Gln Ala Met Asp Gln Glu Gln Ala Phe His Asn Trp
    130                 135                 140

Lys Lys Leu Ser Asn Ser Leu Ser Gly Leu Phe Cys Ser Ser Leu Asn
145                 150                 155                 160

Phe Ile Asp Glu Ser Arg Thr Thr Phe Pro Arg Arg Ser Tyr Ala Ser
                165                 170                 175

Asp Ile Gly Ala Pro Leu Phe Asn Ser Thr Glu Lys Leu Tyr Leu Met
            180                 185                 190

Arg Ala Ser Leu Pro Asn Glu Pro Ile Cys Thr Glu Asn Leu Thr Pro
        195                 200                 205

Phe Ile Lys Leu Leu Pro Thr Arg Gly Lys Ser Gly Leu Thr Ser Leu
    210                 215                 220

Leu Asp Gly His Lys Leu Phe Asp Ser Leu Trp Asn Ser Ile Ser Leu
225                 230                 235                 240

Asp Ile Ala Thr Ile Cys Ser Glu Asp Glu Asp Ala Leu Cys His Tyr
```

```
                      245                 250                 255
        Glu Met Asp Ala Arg Ile Glu Met Val Thr His Val Pro Ser Ala Leu
                    260                 265                 270

Ala Arg Gly Glu Arg Pro Ile Pro Lys Pro Leu Asp Gly Asn Thr Leu
                    275                 280                 285

Arg Cys Asp Thr Asp Lys Pro Phe Asp Ser Tyr Gln Cys Phe Pro Leu
                    290                 295                 300

Pro Glu Pro Ser Gln Thr His Phe Lys Leu Ser Gln Leu Phe Ala Arg
        305                 310                 315                 320

Pro Ile Asn Asn Gly Asn Leu Phe Ala Asn Arg Pro Thr Arg Ile Cys
                    325                 330                 335

Ala Glu Val Asp Arg Ser Thr Trp Thr Ala Phe Leu Ser Val Asp Asp
                    340                 345                 350

Thr Ile Phe Ser Thr His Asp Asn Cys Phe Asp Leu Ser Asn Asp Gln
                    355                 360                 365

Asn Glu Gly Gly Ser Gly Tyr Asp Phe Ile Leu Glu Ser Thr Asp Thr
                    370                 375                 380

Thr Lys Val Thr Pro Ile Val Pro Val Pro Ile His Val Ser Arg Ser
        385                 390                 395                 400

Leu Thr Gly Asn Gly Gln Asp Arg Gly Gly Met Arg Ile Val Phe His
                    405                 410                 415

Asn Asp Asn Asp Thr Pro Val Lys Leu Ile Tyr Phe Glu Ser Leu Pro
                    420                 425                 430

Trp Phe Met Arg Val Tyr Leu Ser Ser Leu Gln Ile Thr Ser Thr Thr
                    435                 440                 445

Ser Pro Gln Leu Gln Glu Asn Asp Ile Ile Leu Asp Lys Tyr Tyr Leu
                    450                 455                 460

Gln Ala Ala Asp Arg Lys Arg Pro Gly His Leu Glu Phe Thr Met Leu
        465                 470                 475                 480

Ile Pro Ala Asn Thr Asp Ile Val Met Thr Tyr Gln Phe Asp Lys Ala
                    485                 490                 495

Leu Leu Gln Phe Ala Glu Tyr Pro Pro Asp Ala Asn His Gly Phe Glu
                    500                 505                 510

Ile Asp Ala Ala Val Ile Thr Val Leu Ser Leu Glu Ser Ser Ser Ser
                    515                 520                 525

Leu Tyr Glu Met Arg Thr Ser Thr Leu Leu Leu Ser Leu Ser Thr Pro
                    530                 535                 540

Asp Phe Ser Met Pro Tyr Asn Val Ile Ile Leu Thr Ser Thr Ile Met
        545                 550                 555                 560

Gly Leu Ile Phe Gly Met Leu Tyr Asn Leu Met Val Lys Arg Met Val
                    565                 570                 575

Thr Val Glu Glu Ala Asp Lys Ile Thr Leu Gln Ser Gly Leu Lys Tyr
                    580                 585                 590

Lys Leu Leu Lys Leu Lys Glu Lys Phe Leu Gly Lys Lys Lys Thr Lys
                    595                 600                 605

Thr Asp
            610

<210> SEQ ID NO 40
<211> LENGTH: 1185
<212> TYPE: DNA
<213> ORGANISM: Saccharomyces cerevisiae

<400> SEQUENCE: 40
atggattcca cagcacttaa ggtagctcta ggctgtattg caattcgttt ggctgtgaac      60
```

```
agccttttc  cctctctaca  acaacaactg  gaccagtctg  tagaattctc  aactcccgta    120
acttcattta  ggtcactaca  ggaaggtata  tacctactgc  ggaacaacat  ccaagtatat    180
aatcatgggg  ttgttcacca  tcctccaatt  ttgattttt   ttctttccct  ctttaattcc    240
gacaggttaa  tttccctcat  atacgcttta  attgatggat  taattgcgta  tcagctgaca    300
gaggtaacaa  aggctttcaa  aaacttgaaa  ctgaaagttt  ggctacctgg  acttctttat    360
gccgtgaatc  ctttgaccct  tttatcgtgc  attagtcggt  catcaatcat  attcacaaat    420
tttgctattt  catcgtcatt  gtattgcata  ttagctgaag  gaaacgttct  tttgtcctct    480
gttatgattt  ctatatctgg  atatttgtca  gtataccta   ttctcctctt  aattccgcta    540
ttaggtatgc  tgaaaagttg  gaggcaaaga  atattatctg  ccattgtttc  catactatct    600
ttattaattc  tgctattatt  cagctacagt  atattaggca  gccaaagttg  gtcatttttg    660
acacaggttt  atggatctat  tataaccttt  gagaaggttt  ttccaaatct  gggtttgtgg    720
tggtacttct  tcattgaaat  gtttgacacc  ttcataccgt  tcttcaaggc  tgtattcaac    780
atttttattg  cagtattcat  tacaccattt  actttgcgct  atcataagca  gccattctac    840
gcattcattt  tatgcattgg  gtggattgtc  cttacaaagc  catatccctc  actaggtgac    900
gctggttttt  tcttcagctt  cctacctttc  ttcacgccac  tatttggata  tttaagatac    960
cccatcatat  cagcattact  gttttacac   gcaattgtt   tggcgccaat  tttctatcat   1020
ctttgggttg  ttttaggttc  agggaatagt  aattttttct  atgctatttc  cctagtttat   1080
gctctggcta  tagcatctat  attagttgac  ttgaactggg  cgatgctgag  aattgaatac   1140
gataacggta  tcccaaattt  caaattgaag  gtaacacaaa  tttaa                   1185
```

<210> SEQ ID NO 41
<211> LENGTH: 394
<212> TYPE: PRT
<213> ORGANISM: Saccharomyces cerevisiae

<400> SEQUENCE: 41

```
Met Asp Ser Thr Ala Leu Lys Val Ala Leu Gly Cys Ile Ala Ile Arg
  1               5                  10                  15

Leu Ala Val Asn Ser Leu Phe Pro Ser Leu Gln Gln Gln Leu Asp Gln
             20                  25                  30

Ser Val Glu Phe Ser Thr Pro Val Thr Ser Phe Arg Ser Leu Gln Glu
         35                  40                  45

Gly Ile Tyr Leu Leu Arg Asn Asn Ile Gln Val Tyr Asn His Gly Val
     50                  55                  60

Val His His Pro Pro Ile Leu Ile Phe Phe Leu Ser Leu Phe Asn Ser
 65                  70                  75                  80

Asp Arg Leu Ile Ser Leu Ile Tyr Ala Leu Ile Asp Gly Leu Ile Ala
                 85                  90                  95

Tyr Gln Leu Thr Glu Val Thr Lys Ala Phe Lys Asn Leu Lys Leu Lys
            100                 105                 110

Val Trp Leu Pro Gly Leu Leu Tyr Ala Val Asn Pro Leu Thr Leu Leu
        115                 120                 125

Ser Cys Ile Ser Arg Ser Ser Ile Ile Phe Thr Asn Phe Ala Ile Ser
    130                 135                 140

Ser Ser Leu Tyr Cys Ile Leu Ala Glu Gly Asn Val Leu Leu Ser Ser
145                 150                 155                 160

Val Met Ile Ser Ile Ser Gly Tyr Leu Ser Val Tyr Pro Ile Leu Leu
                165                 170                 175
```

```
Leu Ile Pro Leu Leu Gly Met Leu Lys Ser Trp Arg Gln Arg Ile Leu
        180                 185                 190

Ser Ala Ile Val Ser Ile Leu Ser Leu Leu Ile Leu Leu Leu Phe Ser
        195                 200                 205

Tyr Ser Ile Leu Gly Ser Gln Ser Trp Ser Phe Leu Thr Gln Val Tyr
        210                 215                 220

Gly Ser Ile Ile Thr Phe Glu Lys Val Phe Pro Asn Leu Gly Leu Trp
225                 230                 235                 240

Trp Tyr Phe Phe Ile Glu Met Phe Asp Thr Phe Ile Pro Phe Phe Lys
                245                 250                 255

Ala Val Phe Asn Ile Phe Ile Ala Val Phe Ile Thr Pro Phe Thr Leu
            260                 265                 270

Arg Tyr His Lys Gln Pro Phe Tyr Ala Phe Ile Leu Cys Ile Gly Trp
        275                 280                 285

Ile Val Leu Thr Lys Pro Tyr Pro Ser Leu Gly Asp Ala Gly Phe Phe
290                 295                 300

Phe Ser Phe Leu Pro Phe Phe Thr Pro Leu Phe Gly Tyr Leu Arg Tyr
305                 310                 315                 320

Pro Ile Ile Ser Ala Leu Leu Phe Leu His Ala Ile Val Leu Ala Pro
                325                 330                 335

Ile Phe Tyr His Leu Trp Val Val Leu Gly Ser Gly Asn Ser Asn Phe
            340                 345                 350

Phe Tyr Ala Ile Ser Leu Val Tyr Ala Leu Ala Ile Ala Ser Ile Leu
        355                 360                 365

Val Asp Leu Asn Trp Ala Met Leu Arg Ile Glu Tyr Asp Asn Gly Ile
370                 375                 380

Pro Asn Phe Lys Leu Lys Val Thr Gln Ile
385                 390

<210> SEQ ID NO 42
<211> LENGTH: 255
<212> TYPE: DNA
<213> ORGANISM: Homo sapiens

<400> SEQUENCE: 42
atggccacgg ggacagacca ggtggtggga ctcggcctcg tcgccgttag cctgatcatc    60
ttcacctact acaccgcctg ggtgattctc ttgccattca tcgacagtca gcatgtcatc   120
cacaagtatt tcctgccccg agcctatgct gtcgccatcc cactggctgc aggcctcctg   180
ctgctcctgt ttgtgggact gttcatctcc tatgtgatgc tgaagaccaa gagagtgacc   240
aagaaggctc agtga                                                     255

<210> SEQ ID NO 43
<211> LENGTH: 84
<212> TYPE: PRT
<213> ORGANISM: Homo sapiens

<400> SEQUENCE: 43

Met Ala Thr Gly Thr Asp Gln Val Val Gly Leu Gly Leu Val Ala Val
1               5                  10                  15

Ser Leu Ile Ile Phe Thr Tyr Tyr Thr Ala Trp Val Ile Leu Leu Pro
            20                  25                  30

Phe Ile Asp Ser Gln His Val Ile His Lys Tyr Phe Leu Pro Arg Ala
        35                  40                  45

Tyr Ala Val Ala Ile Pro Leu Ala Ala Gly Leu Leu Leu Leu Leu Phe
    50                  55                  60
```

Val Gly Leu Phe Ile Ser Tyr Val Met Leu Lys Thr Lys Arg Val Thr
 65                  70                  75                  80

Lys Lys Ala Gln

<210> SEQ ID NO 44
<211> LENGTH: 369
<212> TYPE: DNA
<213> ORGANISM: Homo sapiens

<400> SEQUENCE: 44
atgctctccg tgggcgggct tcggttgagt ttggtccgct tttcctttct gctcctcagg    60
ggagcattgc ttccttctct cgcagtgacc atgacgaaat tagcgcagtg ctttgggga    120 ctagcgatcc tgggctccac ctgggtggcc ctgaccacgg gagccttggg cctggagctg   180
cccttgtcct gccaggaagt cctgtggcca ctgcccgcct acttgctggt gtccgccggc   240
tgctatgccc tgggcactgt gggctatcgt gtggccactt tcatgactg cgaggacgcc    300 gcacgcgagc tgcagagcca gatacaggag gcccgagccg acttagcccg caggggctg    360 cgcttctga                                                           369

<210> SEQ ID NO 45
<211> LENGTH: 122
<212> TYPE: PRT
<213> ORGANISM: Homo sapiens

<400> SEQUENCE: 45

Met Leu Ser Val Gly Gly Leu Arg Leu Ser Leu Val Arg Phe Ser Phe
 1               5                  10                  15

Leu Leu Leu Arg Gly Ala Leu Leu Pro Ser Leu Ala Val Thr Met Thr
                 20                  25                  30

Lys Leu Ala Gln Trp Leu Trp Gly Leu Ala Ile Leu Gly Ser Thr Trp
         35                  40                  45

Val Ala Leu Thr Thr Gly Ala Leu Gly Leu Glu Leu Pro Leu Ser Cys
     50                  55                  60

Gln Glu Val Leu Trp Pro Leu Pro Ala Tyr Leu Leu Val Ser Ala Gly
 65                  70                  75                  80

Cys Tyr Ala Leu Gly Thr Val Gly Tyr Arg Val Ala Thr Phe His Asp
                 85                  90                  95

Cys Glu Asp Ala Ala Arg Glu Leu Gln Ser Gln Ile Gln Glu Ala Arg
            100                 105                 110

Ala Asp Leu Ala Arg Arg Gly Leu Arg Phe
        115                 120

<210> SEQ ID NO 46
<211> LENGTH: 744
<212> TYPE: DNA
<213> ORGANISM: Homo sapiens

<400> SEQUENCE: 46
atggcggccg aggcggacgg accgcttaaa cggctgctcg tgccgattct tttacctgag    60
aaatgctacg accaactttt cgttcagtgg gacttgcttc acgtcccctg cctcaagatt   120
ctcctcagca aaggcctggg gctgggcatt gtggctggct cacttctagt aaagctgccc    180
caggtgttta aaatccgggg agccaagagt gctgaagggt tgagtctcca gtctgtaatg   240
ctggagctag tggcattgac tgggaccatg gtctacagca tcactaacaa cttcccattc   300
agctcttggg gtgaagcctt attcctgatg ctccagacga tcaccatctg cttcctggtc   360
atgcactaca gaggacagac tgtgaaaggt gtcgctttcc tcgcttgcta cggcctggtc   420

```
ctgctggtgc ttctctcacc tctgacgccc ttgactgtag tcaccctgct ccaggcctcc    480
aatgtgcctg ctgtggtggt ggggaggctt ctccaggcag ccaccaacta ccacaacggg    540
tacacaggcc agctctcagc catcacagtc ttcctgctgt ttgggggctc cctggcccga    600
atcttcactt ccattcagga aaccggagat cccctgatgg ctgggacctt tgtggtctcc    660
tctctctgca acggcctcat cgccgcccag ctgctcttct actggaatgc aaagcctccc    720
cacaagcaga aaaaggcgca gtag                                           744

<210> SEQ ID NO 47
<211> LENGTH: 247
<212> TYPE: PRT
<213> ORGANISM: Homo sapiens

<400> SEQUENCE: 47
```

Met Ala Ala Glu Ala Asp Gly Pro Leu Lys Arg Leu Leu Val Pro Ile
 1               5                  10                  15

Leu Leu Pro Glu Lys Cys Tyr Asp Gln Leu Phe Val Gln Trp Asp Leu
             20                  25                  30

Leu His Val Pro Cys Leu Lys Ile Leu Leu Ser Lys Gly Leu Gly Leu
         35                  40                  45

Gly Ile Val Ala Gly Ser Leu Leu Val Lys Leu Pro Gln Val Phe Lys
     50                  55                  60

Ile Arg Gly Ala Lys Ser Ala Glu Gly Leu Ser Leu Gln Ser Val Met
65                  70                  75                  80

Leu Glu Leu Val Ala Leu Thr Gly Thr Met Val Tyr Ser Ile Thr Asn
                 85                  90                  95

Asn Phe Pro Phe Ser Ser Trp Gly Glu Ala Leu Phe Leu Met Leu Gln
            100                 105                 110

Thr Ile Thr Ile Cys Phe Leu Val Met His Tyr Arg Gly Gln Thr Val
        115                 120                 125

Lys Gly Val Ala Phe Leu Ala Cys Tyr Gly Leu Val Leu Leu Val Leu
    130                 135                 140

Leu Ser Pro Leu Thr Pro Leu Thr Val Val Thr Leu Leu Gln Ala Ser
145                 150                 155                 160

Asn Val Pro Ala Val Val Gly Arg Leu Leu Gln Ala Ala Thr Asn
                165                 170                 175

Tyr His Asn Gly Tyr Thr Gly Gln Leu Ser Ala Ile Thr Val Phe Leu
            180                 185                 190

Leu Phe Gly Gly Ser Leu Ala Arg Ile Phe Thr Ser Ile Gln Glu Thr
        195                 200                 205

Gly Asp Pro Leu Met Ala Gly Thr Phe Val Val Ser Ser Leu Cys Asn
    210                 215                 220

Gly Leu Ile Ala Ala Gln Leu Leu Phe Tyr Trp Asn Ala Lys Pro Pro
225                 230                 235                 240

His Lys Gln Lys Lys Ala Gln
                245

```
<210> SEQ ID NO 48
<211> LENGTH: 25
```

```
<212> TYPE: DNA
<213> ORGANISM: Artificial Sequence
<220> FEATURE:
<223> OTHER INFORMATION: Artificially synthesized primer sequence

<400> SEQUENCE: 48
atgacaatgt ggggaagtca acggg                                         25

<210> SEQ ID NO 49
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 49
tgtgtggtta ccgttctttg aatacataga                                    30

<210> SEQ ID NO 50
<211> LENGTH: 29
<212> TYPE: DNA
<213> ORGANISM: Artificial Sequence
<220> FEATURE:
<223> OTHER INFORMATION: Artificially synthesized primer sequence

<400> SEQUENCE: 50
atagaaaatg atttatggta cagctcaaa                                     29

<210> SEQ ID NO 51
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 51
agaccaaatt aattatgcct ttacatgtac                                    30

<210> SEQ ID NO 52
<211> LENGTH: 40
<212> TYPE: DNA
<213> ORGANISM: Artificial Sequence
<220> FEATURE:
<223> OTHER INFORMATION: Artificially synthesized primer sequence

<400> SEQUENCE: 52
agaattcacc atgagcaaca tgaatatact tgcgtatctt                         40

<210> SEQ ID NO 53
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 53
gaaattccaa tgtattccat attcacttat                                    30

<210> SEQ ID NO 54
<211> LENGTH: 42
<212> TYPE: DNA
<213> ORGANISM: Artificial Sequence
<220> FEATURE:
<223> OTHER INFORMATION: Artificially synthesized primer sequence

<400> SEQUENCE: 54
aagatctaat acattaaaac attttagatt aatgaatatg tg                      42
```

```
<210> SEQ ID NO 55
<211> LENGTH: 34
<212> TYPE: DNA
<213> ORGANISM: Artificial Sequence
<220> FEATURE:
<223> OTHER INFORMATION: Artificially synthesized primer sequence

<400> SEQUENCE: 55
aggtaccgta cactccactc tatgatgatc attc                              34
```

METHODS OF SCREENING FOR COMPOUNDS THAT INHIBIT THE BIOSYNTHESIS OF GPI IN MALARIA PARASITES

TECHNICAL FIELD

The present invention relates to methods of screening for compounds that inhibit the biosynthesis of GPI in malaria parasites.

BACKGROUND ART

Malaria is the most common infectious human disease caused by parasitic protozoans. The disease is caused by infection with malaria parasites and is mediated by the mosquito, *Anopheles gambiae*. Every year there are estimated 500 million cases of malaria infection, including more than two million fatal cases (Gardner, et al., Nature 419:498-511, 2003). At present 40% of the world's population lives in malaria-epidemic areas, where it is said that one in every three infants dies from malaria.

Glycosylphosphatidylinositol (GPI) is known to play a key role in the growth and infectivity of parasites, including malaria parasites. There are many GPI-anchored proteins on the cell surface of these parasites. GPI-anchored proteins include proteins such as MSP-1 that function when the parasites invade red blood cells. GPI-anchored proteins act as parasitic antigens and initiate an immune response in the host. Thus, they have long been the subject of research aimed at vaccine development.

GPI not only functions as an anchor to tether proteins to the cell membrane, but is also an abundant glycolipid component of malaria parasite cell membranes. Recent studies have revealed that GPI is toxic and causes lethal symptoms. GPI induces the expression of inflammatory cytokines such as TNF-α, and of adhesion molecules. As a result, infected red blood cells adhere to capillaries, obstructing vessels (sequestration), brain blood vessels in particular. This induces further inflammatory reactions that are believed to lead to encephalopathy. Very recently, Schofield et al. reported that an anti-GPI antibody reduces lethality in an in vivo infection model system using the murine malaria parasite *Plasmodium berghei*, and that in vitro, the antibody inhibits late inflammatory reactions caused by *Plasmodium falciparum* (Schofield L, et al., Nature 418:785-789, 2002). These findings suggest that GPI is a major factor in the lethality of malarial infections.

It has also been reported that the acylation of inositol is essential for binding mannose to GPI (Gerold, P. et al., Biochem. J. 344:731-738, 1999), and that the inhibition of inositol acylation, caused by excess glucosamine, inhibits the maturation of the malaria parasite *P. falciparum* (Naik, R. S. et al., J. Biol. Chem. 278:2036-2042, 2003). Thus, compounds that can selectively inhibit GPI biosynthesis, particularly the acylation of inositol, may be highly useful antimalarial drugs.

DISCLOSURE OF THE INVENTION

An objective of the present invention is to provide antimalarial drugs that inhibit the biosynthesis of GPI. More specifically, the present invention provides the malaria parasite DNA that encodes the GWT1 protein, which is a protein involved in the biosynthesis of GPI (GPI synthase). The present invention also provides a method of using this DNA in methods of screening for antimalarial drugs. The present invention also provides degenerate mutant DNAs of the DNA that encodes the malaria parasite GPI biosynthesis protein. These degenerate mutant DNAs have a lower AT content than the original DNA. The present invention also provides a method of using the degenerate mutant DNAs in methods of screening for antimalarial drugs.

The GWT1 gene was originally found to encode a fungal GPI-anchored protein synthase (WO 02/04626), and is conserved in organisms ranging from yeasts to humans. The present inventors confirmed that GWT1 homologues (PfGWT1 for *P. falciparum* GWT1; PyGWT1 for *P. yoelii* yoelii GWT1) are included in the entire genomic sequences of *Plasmodium falciparum* (*P. falciparum*) and *Plasmodium yoelii* yoelii (*P. yoelii* yoelii) (Gardner, et al., Nature 419:498-511, 2003; Carlton et al., Nature 419:512-519, 2003). The present inventors also found that the GWT1 gene product acts as a GlcN-PI acyltransferase in the GPI biosynthesis pathway. The PfGWT1 gene product is expected to have similar activity, and thus compounds that inhibit this activity can be promising antimalarial drugs.

In WO 02/04626, the present inventors disclosed a group of compounds that inhibit the activity of the fungal GWT1 gene product. Compounds inhibiting the activity of the PfGWT1 gene product were expected to be antimalarial drugs.

In the present invention, the present inventors succeeded in isolating a region thought to be almost the full length of the PfGWT1. Using the GWT1 gene products of malaria parasites such as *P. falciparum*, antimalarial drugs can be screened through binding assays, glucosaminyl(acyl)phosphatidylinositol (PI-GlcN) acyltransferase assays, or using GPI-anchored protein detection systems. Compounds obtained from such screenings can be promising antimalarial drugs. Furthermore, the present inventors revealed that degenerate mutant DNAs (degenerate mutants of the DNA that encodes the malaria parasite GPI biosynthesis protein) having a lower AT content than the original DNA, complement the phenotype of the GWT1 gene-deficient fungus. Thus, it is possible to screen for compounds that inhibit the activity of proteins involved in GPI biosynthesis in malarial parasites by using, as an index, the phenotype of a GPI synthase gene-deficient fungus, into which a degenerate mutant DNA with a lower AT content (than the DNA encoding the GPI biosynthesis protein in malaria parasites) has been introduced.

Specifically, the present invention provides the following [1] to [25]:

[1] a DNA according to any one of (a) to (d), which encodes a protein of a malaria parasite having a GlcN-PI acyltransferase activity:

(a) a DNA encoding a protein comprising the amino acid sequence of SEQ ID NO: 2 or 4, (b) a DNA comprising the nucleotide sequence of SEQ ID NO: 1 or 3, (c) a DNA hybridizing to a DNA comprising the nucleotide sequence of SEQ ID NO: 1 or 3 under stringent conditions, and (d) a DNA encoding a protein which comprises the amino acid sequence of SEQ ID NO: 2 or 4, in which one or more amino acids have been added, deleted, substituted, and/or inserted;

[2] a protein encoded by the DNA according to [1];

[3] a vector into which the DNA according to [1] is inserted;

[4] a transformant which retains, in an expressible state, the DNA according to [1] or the vector according to [3];

[5] an antimalarial drug which comprises as an active ingredient a compound that inhibits the activity of the protein according to [2];

[6] the antimalarial drug according to [5], wherein the compound that inhibits the activity of the protein according to [2] is at least one selected from the group consisting of the following compounds (1) to (5):

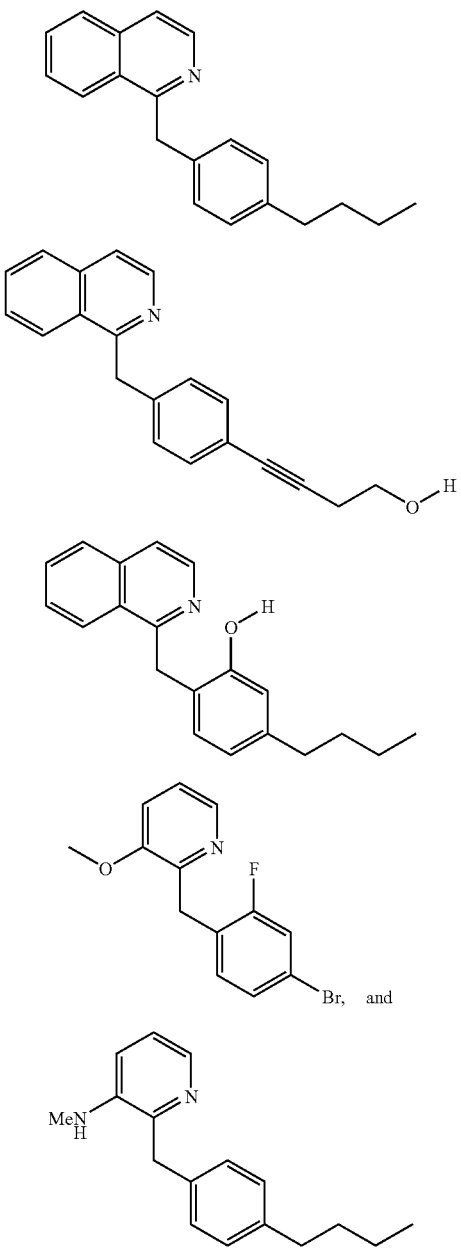

[7] a method of screening for a compound having antimalarial activity, which comprises the steps of:

(1) contacting the protein according to [2] with a test sample and a labeled compound that has the activity of binding to the protein, (2) detecting the labeled compound that binds to the protein, and, (3) selecting a test sample that decreases the amount of labeled compound that binds to the protein;

[8] the method according to [7], wherein the labeled compound that has the activity of binding to the protein is produced by labeling at least one compound selected from the group consisting of the compounds (1) to (5) according to [6];

[9] a method of screening for a compound having antimalarial activity, which comprises the steps of:

(1) contacting a test sample with the protein according to [2], (2) detecting GlcN-(acyl)PI, and, (3) selecting a test compound that decreases the level of GlcN-(acyl)PI;

[10] a method of screening for a compound having antimalarial activity, which comprises the steps of:

(1) contacting a test sample with a cell overexpressing the protein according to [2], (2) determining the amount of GPI-anchored protein transported to the cell wall, and, (3) selecting a test sample that decreases the amount of the GPI-anchored protein transported to the cell wall, as determined in step (2);

[11] a method for treating malaria, which comprises administering a compound that inhibits the activity of the protein according to [2];

[12] the method according to [11], wherein the compound that inhibits the activity of the protein according to [2] is the compound according to [5];

[13] a DNA encoding a protein that has the activity of complementing the phenotype of a GPI synthase gene-deficient yeast, which is a degenerate mutant of a DNA encoding a protein involved in GPI biosynthesis in malaria parasites, and that has a lower AT content than the original DNA;

[14] a DNA encoding a protein that has the activity of complementing the phenotype of a GPI synthase gene-deficient yeast, which is a degenerate mutant of a DNA encoding a protein involved in GPI biosynthesis in malaria parasites, and that has an AT content which is reduced by 70%;

[15] the DNA according t6 [13] or [14], which is selected from the group consisting of:

(a) a DNA encoding a protein that comprises any one of the amino acid sequences of SEQ ID NOs: 2 and 4, and odd sequence identification numbers in SEQ ID NOs: 6-47, (b) a DNA comprising any one of the nucleotide sequences of SEQ ID NOs: 1 and 3, and even sequence identification numbers in—SEQ ID NOs: 6-47, (c) a DNA hybridizing under stringent conditions to a DNA that comprises any one of the nucleotide sequences of SEQ ID NOs: 1 and 3, and even sequence identification numbers in SEQ ID NOs: 6-47, and, (d) a DNA encoding a protein which comprises any one of the amino acid sequences of SEQ ID NOs: 2 and 4, and odd sequence identification numbers in SEQ ID NOs: 6-47, in which one or more amino acids have been added, deleted, substituted, and/or inserted;

[16] a DNA comprising the nucleotide sequence of SEQ ID NO: 5;

[17] a vector in which a DNA according to any one of [13] to [16] is inserted;

[18] a transformant which retains, in an expressible state, the DNA according to any one of [13] to [16] or the vector according to [17];

[19] the transformant according to [18], which is a GPI synthase gene-deficient fungus;

[20] the transformant according to [18], which is a GPI synthase gene-deficient yeast;

[21] a method for producing a protein encoded by a DNA according to any one of [13] to [16], which comprises the steps of culturing the transformant according to any one of [18] to [20], and recovering the expressed protein from the transformant or the culture supernatant;

[22] a method of screening for a compound having antimalarial activity, which comprises the steps of:
  (1) contacting a test sample with a GPI synthase gene-deficient fungus expressing the DNA according to any one of [13] to [16],
  (2) assaying the growth of that fungus, and,
  (3) selecting a test compound that inhibits the growth of that fungus;
[23] a method of screening for a compound having antimalarial activity, which comprises the steps of:
  (1) contacting a test sample with a GPI synthase gene-deficient fungus expressing the DNA according to any one of [13] to [16],
  (2) determining the amount of a GPI-anchored protein transported to the fungal cell walls, and,
  (3) selecting a test sample that decreases the amount of the GPI-anchored protein transported to the cell wall, as determined in step (2);
[24] a method of screening for a compound having antimalarial activity, which comprises the steps of:
  (1) introducing the DNA according to any one of [13] to [16] into a GPI synthase gene-deficient fungus and expressing the protein encoded by the DNA,
  (2) preparing the protein expressed in step (1),
  (3) contacting the prepared protein with a test sample and a labeled compound that has the activity of binding to the protein,
  (4) detecting the labeled compound that binds to the protein, and,
  (5) selecting a test sample that decreases the amount of labeled compound that binds to the protein; and,
[25] a method of screening for a compound having antimalarial activity, which comprises the steps of:
  (1) introducing into a GWT1-deficient fungus, (i) a DNA encoding a protein that has the activity of complementing the phenotype of a GWT1-deficient yeast, wherein the DNA is a degenerate mutant of a DNA encoding a malaria parasite GWT1 protein that has a lower AT content than the original DNA, or (ii) a vector into which the degenerate mutant of DNA has been inserted, and expressing the protein encoded by the degenerate mutant DNA,
  (2) preparing the protein expressed in step (1),
  (3) contacting the prepared protein with a test sample,
  (4) detecting GlcN-(acyl)PI, and
  (5) selecting a test compound that decreases the level of GlcN-(acyl)PI.

The DNA encoding the GWT1 protein of Plasmodium falciparum (PfGWT1) was isolated for the first time in the present invention. The nucleotide sequence of the DNA encoding the PfGWT1 protein is shown in SEQ ID NO: 1, and the amino acid sequence of the PfGWT1 protein is set forth in SEQ ID NO: 2. In addition, the nucleotide sequence of the DNA encoding the GWT1 protein of Plasmodium vivax (PvGWT1) is shown in SEQ ID NO: 3, and the amino acid sequence of the PvGWT1 protein is set forth in SEQ ID NO: 4.

The GWT1 protein is involved in the biosynthesis of glycosylphosphatidylinositol (GPI), which is essential for the growth and infectivity of malaria parasites. Thus, compounds that inhibit the activity of the malaria parasite GWT1 protein can be used as antimalarial drugs. Such antimalarial drugs can be screened using this malaria parasite GWT1 protein.

The present invention provides DNAs encoding the malaria parasite GWT1 protein. Such DNAs include DNA encoding a protein comprising the amino acid sequence of SEQ ID NO: 2 or 4, and DNA comprising the nucleotide sequence of SEQ ID NO: 1 or 3.

The present invention also provides DNAs encoding proteins that are functionally equivalent to the protein comprising the amino acid sequence of SEQ ID NO: 2 or 4. Herein, the expression "functionally equivalent" refers to having biological properties equivalent to those of the protein of interest, comprising the amino acid sequence of SEQ ID NO: 2 or 4 (the PfGWT1 or PvGWT1 proteins). The biological properties of the PfGWT1 and PvGWT1 proteins include GlcN-PI acyltransferase activity. The GlcN-PI acyltransferase activity can be measured by the method reported by Costello and Orlean (J. Biol. Chem. (1992) 267:8599-8603), or Franzot and Doering (Biochem. J. (1999) 340:25-32).

DNAs encoding proteins functionally equivalent to the protein comprising the amino acid sequence of SEQ ID NO: 2 or 4 include: DNAs that hybridize under stringent conditions to the DNA comprising the nucleotide sequence of SEQ ID NO: 1 or 3, and DNA encoding a protein which comprises the amino acid sequence of SEQ ID NO: 2 or 4, in which one or more amino acids have been added, deleted, substituted, and/or inserted.

The DNAs of the present invention can be isolated by methods well known to those skilled in the art. Examples of such methods include the use of hybridization (Southern E. M., J. Mol. Biol. 98: 503-517, 1975) and the polymerase chain reaction (PCR) (Saiki R. K. et al., Science230: 1350-1354, 1985; Saiki R. K. et al., Science239: 487-491, 1988). More specifically, it would be routine experimentation for those skilled in the art to isolate, from malaria parasites, a DNA highly homologous to DNA comprising the nucleotide sequence of SEQ ID NO: 1 or 3, using the DNA of SEQ ID NO: 1 or 3 or portions thereof as a probe, or by using as a primer a DNA which specifically hybridizes to the DNA comprising the nucleotide sequence of SEQ ID NO: 1 or 3. Furthermore, DNAs that can be isolated by hybridization or PCR techniques, and that hybridize with the DNA comprising the nucleotide sequence of SEQ ID NO: 1 or 3, are also comprised in the DNAs of the present invention. Such DNAs include DNA encoding a malaria parasite homologue of the protein comprising the amino acid sequence of SEQ ID NO: 2 or 4. The malaria parasite homologue includes those of *Plasmodium falciparum*, *Plasmodium vivax*, *Plasmodium malariae*, and *Plasmodium ovale*, which comprise the amino acid sequence of SEQ ID NO: 2 or 4.

Preferably, a DNA described above is isolated using hybridization reactions under stringent hybridization conditions. As used herein, the expression "stringent hybridization conditions" refers to, for example, hybridization in 4×SSC at 65° C. followed by washing in 0.1×SSC at 65° C. for one hour. Alternative stringent conditions are hybridization in 4×SSC containing 50% formamide at 42° C. Further alternative stringent conditions are hybridization in PerfectHyb™ (TOYOBO) solution at 65° C. for 2.5 hours, followed by washing: (1) in 2×SSC containing 0.05% SDS at 25° C. for five minutes; (2) in 2×SSC containing 0.05% SDS at 25° C. for 15 minutes; and (3) in 0.1×SSC containing 0.1% SDS at 50° C. for 20 minutes. The DNA thus isolated is expected to encode a polypeptide with a high homology at the amino acid level to the amino acid sequence of SEQ ID NO: 2 or 4. Herein, "high homology" means a sequence identity of at least 70% or more, preferably 80% or more, more preferably 90% or more, and most preferably 95% or more, in the whole amino acid sequence.

The degree of identity at the amino acid sequence level or nucleotide sequence level can be determined using the BLAST algorithm of Karlin and Altschul (Karlin S, and Altschul S. F, Proc. Natl. Acad. Sci. USA. 87: 2264-2268, 1990; Karlin S, and Altschul S. F, Proc. Natl. Acad. Sci. USA. 90:

5873-5877, 1993). BLAST algorithm-based programs, called BLASTN and BLASTX, have been developed (Altschul S. F. et al. J. Mol. Biol. 215: 403, 1990). When a nucleotide sequence is analyzed using BLASTN, the parameters are set, for example, at score=100 and word length=12. On the other hand, when an amino acid sequence is analyzed using BLASTX, the parameters are set, for example, at score=50 and word length=3. When the BLAST and Gapped BLAST programs are used, the default parameters for each program are used. Specific procedures for such analysis are known.

DNAs of the present invention comprise genomic DNAs, cDNAs, and chemically synthesized DNAs. A Genomic DNA or cDNA can be prepared according to conventional methods known to those skilled in the art. For example, a genomic DNA can be prepared as follows: (i) extracting a genomic DNA from malaria parasites; (ii) constructing a genomic library (using, for example, a plasmid, phage, cosmid, BAC, or PAC, as a vector); (iii) spreading the library; and then (iv) conducting colony hybridization or plaque hybridization using probes prepared based on a DNA which encodes the malaria parasite GWT1 protein of the present invention (e.g., SEQ ID NO: 1 or 3). Alternatively, genomic DNA can be prepared by PCR, using primers specific to a DNA which encodes the malaria parasite GWT1 protein of the present invention. (e.g., SEQ ID NO: 1 or 3). On the other hand, cDNA can be prepared, for example, as follows: (i) synthesizing cDNA based on mRNA extracted from malaria parasites; (ii) constructing a cDNA library by inserting the synthesized cDNA into vectors such as XZAP; (iii) spreading the cDNA library; and (iv) conducting colony hybridization or plaque hybridization as described above. Alternatively, the cDNA can also be prepared using PCR.

The present invention also provides DNAs encoding proteins structurally similar to the protein comprising the amino acid sequence of SEQ ID NO: 2 or 4. Such DNAs include those which comprise nucleotide sequences encoding proteins comprising amino acid sequences in which one or more amino acid residues are substituted, deleted, inserted, and/or added. There is no limitation on the number and site of the amino acid mutation in proteins mentioned above, so long as the mutated protein retains functions of the original protein such as those described in Mark, D. F. et al., Proc. Natl. Acad. Sci. USA (1984) 81, 5662-5666; Zoller, M. J. & Smith, M., Nucleic Acids Research (1982) 10, 6487-6500; Wang, A. et al., Science 224, 1431-1433; Dalbadie-McFarland, G. et al., Proc. Natl. Acad. Sci. USA (1982) 79, 6409-6413. The percentage of mutated amino acids is typically 10% or less, preferably 5% or less, and more preferably 1% or less of the total amino acid residues. In addition, the number of mutated amino acids is usually 30 amino acids or less, preferably 15 amino acids or less, more preferably five amino acids or less, still more preferably three amino acids or less, even more preferably two amino acids or less.

It is preferable that the mutant amino acid residue be one that retains the properties of the side-chain after its mutation (a process known as conservative amino acid substitution). Examples of amino acid side chain properties are hydrophobicity (A, I, L, M, F, P, W, Y, V) and hydrophilicity (R, D, N, C, E, Q, G, H, K, S, T). Side chains include: aliphatic sidechains (G, A, V, L, I, P); side chains containing an hydroxyl group (S, T, Y); side chains containing a sulfur atom (C, M); side chains containing a carboxylic acid and an amide (D, N, E, Q); basic side-chains (R, K, H); and aromatic side-chains (H, F, Y, W).

A fusion protein comprising the malaria parasite GWT1 protein is an example of a protein to which one or more amino acids residues have been added. Fusion proteins can be made by techniques well known to a person skilled in the art. For example, and without limitation to this particular technique, the DNA encoding the malaria parasite GWT1 protein of the present invention can be combined with DNA encoding another peptide or protein such that their reading frames match. A protein of the present invention can form a fusion protein with a number of known peptides. Such peptides include FLAG (Hopp, T. P. et al., Biotechnology (1988) 6, 1204-1210), 6×His, 10×His, Influenza agglutinin (HA), human c-myc fragment, VSP-GP fragment, p18HIV fragment, T7-tag, HSV-tag, E-tag, SV40T antigen fragment, lck tag, α-tubulin fragment, B-tag, and Protein C fragment. Examples of proteins that may be fused to a protein of the present invention include glutathione-S-transferase (GST), HA, immunoglobulin constant region, β-galactosidase, and maltose-binding protein (MBP).

In addition to using the above-mentioned hybridization and PCR techniques, those skilled in the art could prepare the above-described DNA by methods including, for example, site-directed mutagenesis to introduce mutations in that DNA (Kramer W. and Fritz H-J., Methods Enzymol. 154: 350, 1987). A protein's amino acid sequence may also be mutated in nature due to mutation of the nucleotide sequence which encodes the protein. In addition, degenerate mutant DNAs, in which nucleotide mutations do not result in amino acid mutations in the proteins (degeneracy mutants), are also comprised in the present invention. Furthermore, the present invention also comprises proteins encoded by the above-described DNAs of this invention.

The present invention provides vectors containing the DNAs of the present invention, transformants retaining the DNAs or vectors of the present invention, and methods for producing proteins of the present invention which utilize these transformants.

A vector of the present invention is not limited so long as the DNA inserted into the vector is stably retained. For example, pBluescript® vector (Stratagene) is preferable as a cloning vector when using *E. coli* as a host. An expression vector is particularly useful when using a vector to produce a protein of the present invention. The expression vector is not specifically limited, so long as it expresses proteins in vitro, in *E. coli*, in cultured cells, and in vivo. Preferable examples of expression vectors include the pBEST vector (Promega Corporation) for in vitro expression, the pET vector (Novagen) for expression in *E. coli*, the pME18S-FL3 vector (GenBank Accession No. AB009864) for expression in cultured cells, and the pME18S vector (Mol. Cell Biol. 8: 466-472, 1988) for in vivo expression. The insertion of a DNA of the present invention into a vector can be carried out by conventional methods, for example, by a ligase reaction using restriction enzyme sites (Current Protocols in Molecular Biology, ed. by Ausubel et al., John Wiley & Sons, Inc. 1987, Section 11.4-11.11).

The host cell into which the vector of the present invention is introduced is not specifically limited, and various host cells can be used according to the objectives of this invention. For example, cells that can be used to express the proteins include, but are not limited to, bacterial cells (e.g., *Streptococcus, Staphylococcus, E. coli, Streptomyces, Bacillus subtilis*), fungal cells (e.g., yeast, *Aspergillus*), insect cells (e.g., Drosophila S2, Spodoptera SF9), animal cells (e.g., CHO, COS, HeLa, C127, 3T3, BHK, HEK293, Bowes melanoma cell), and plant cells. The transfection of a vector to a host cell can be carried out by conventional methods such as calcium phosphate precipitation, electroporation (Current protocols in Molecular Biology, ed. by Ausubel et al., John Wiley &

Sons, Inc. 1987, Section 9.1-9.9), the Lipofectamine method (GIBCO-BRL), and microinjection.

By incorporating an appropriate secretion signal into the protein of interest, the protein expressed in host cells can be secreted into the lumen of the endoplasmic reticulum, into cavities around the cells, or into the extracellular environment. These signals may be endogenous or exogenous to the protein of interest.

When a protein of the present invention is secreted into the culture medium, it is collected from that medium. If a protein of the present invention is produced intracellularly, the cells are lysed and then the protein is collected.

A protein of the present invention can be collected and purified from a recombinant cell culture using methods known in the art, including, but not limited to, ammonium sulfate or ethanol precipitation, acid extraction, anionic or cationic exchange chromatography, phosphocellulose chromatography, hydrophobic interaction chromatography, affinity chromatography, hydroxylapatite chromatography, and lectin chromatography.

Compounds including DNAs of the present invention are isolated compounds. Herein, the term "isolated" refers to being separated from the original environment (for example, the natural environment if it is naturally-occurring). A compound in a sample where the compound of interest is substantially abundant, and/or in a sample where the compound of interest has been partially or substantially purified, is an "isolated" compound. The term "substantially purified", as used herein, refers to a state where the compound has been separated from the original environment, and from which at least 60%, preferably 75%, and most preferably 90% of other coexisting natural components have been removed.

The present invention provides an antimalarial drug that inhibits the activity of the GWT1 gene product of malaria parasites. A preferred compound inhibiting the activity of the GWT1 gene product of malaria parasites is the compound described in WO 02/04626, and includes the compounds (1) to (5):

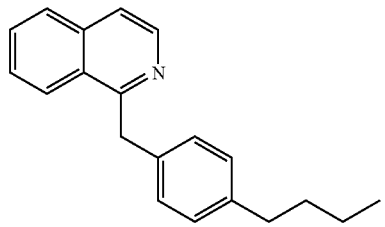

compound (1): 1-(4-butyl benzyl)isoquinoline

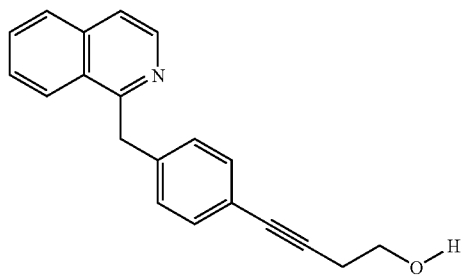

compound (2): 4-[4-(1-isoquinolyl methyl)phenyl]-3-butyne-1-ol

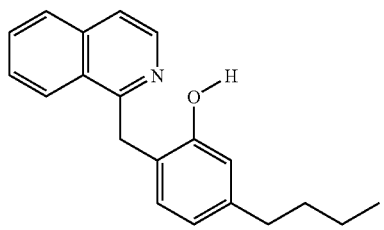

compound (3): 5-butyl-2-(1-isoquinolyl methyl)phenol

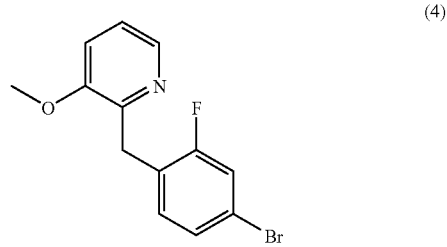

compound (4): 2-(4-bromo-2-fluorobenzyl)-3-methoxypyridine

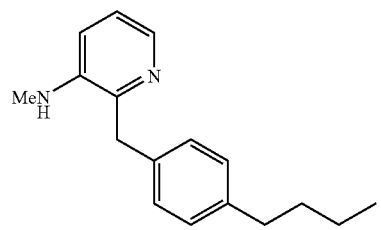

compound (5): N-[2-(4-butyl benzyl)-3-pyridyl]-N-methylamine

A Compound that inhibits the activity of the malaria parasite GWT1 gene product, or a salt thereof, or a hydrate thereof, can be administered as it is to mammals (preferably humans). It can also be formulated by a conventional method into a tablet, powder, fine granule, granule, coated tablet, capsule, syrup, troche, inhalant, suppository, injection, ointment, eye ointment, eye drop, nasal drop, ear drop, cataplasm, lotion, and such, and then administered.

For formulation of a pharmaceutical, auxiliary agents ordinarily used in pharmaceutical formulations (for example, fillers, binders, lubricants, coloring agents, flavoring agents, and as necessary, stabilizers, emulsifiers, absorbefacient, surfactants, pH regulators, antiseptics, and antioxidants) can be used. A pharmaceutical formulation can be prepared using an ordinary method combining components that are generally used as ingredients for pharmaceutical preparations.

For example, oral formulations can be produced by combining a compound of the present invention or a pharmaceutically acceptable salt thereof with a filler, and as necessary, a binder, disintegrator, lubricant, coloring agent, flavoring agent, and such, and then formulating the mixture into a powder, fine granule, granule, tablet, coated tablet, capsule, and such by usual methods.

Examples of these components include: animal fat and vegetable oils such as soybean oil, beef tallow, and synthetic glyceride, hydrocarbons such as liquid paraffin, squalene, and solid paraffin; ester oils such as octyldodecyl myristate and isopropyl myristate; higher alcohols such as cetostearyl alcohol and behenyl alcohol; silicone resin; silicone oil; surfactants such as polyoxyethylene fatty acid ester, sorbitan fatty acid ester, glycerol fatty acid ester, polyoxyethylene sorbitan fatty acid ester, polyoxyethylene hardened castor oil, and polyoxyethylene polyoxypropylene block copolymer; water-soluble macromolecules such as hydroxyethyl cellulose, polyacrylic acid, carboxyvinyl polymer, polyethylene glycol, polyvinyl pyrrolidone, and methyl cellulose; lower alcohols such as ethanol and isopropanol; polyhydric alcohols such as glycerol, propylene glycol, dipropylene glycol, and sorbitol; sugars such as glucose and sucrose; inorganic powder such as silicic acid anhydride, magnesium aluminum silicate, and aluminum silicate; and purified water. Examples of fillers include lactose, corn starch, refined white sugar, glucose, mannitol, sorbitol, crystalline cellulose, and silicon dioxide. Binders are polyvinyl alcohol, polyvinyl ether, methyl cellulose, ethyl cellulose, gum arabic, tragacanth, gelatin, shellac, hydroxypropylmethyl cellulose, hydroxypropyl cellulose, polyvinyl pyrrolidone, polypropyleneglycol polyoxyethylene block polymer, meglumine, and such. Examples of disintegrators include starch, agar, powdered gelatin, crystalline cellulose, calcium carbonate, sodium hydrogencarbonate, calcium citrate, dextrin, pectin, and calcium carboxymethylcellulose. Lubricants are magnesium stearate, talc, polyethyleneglycol, silica, hardened vegetable oil, and such. Examples of coloring agents are those accepted for addition to pharmaceuticals. Flavoring agents are cocoa powder, 1-menthol, aromatic dispersant, mint oil, borneol, cinnamon powder, and such. The use of sugar coating and other appropriate coating as necessary is of course permissible for these tablets and granules.

Furthermore, liquid formulations such as syrups and injections can be prepared using conventional methods. In such methods, pH regulators, solubilizers, isotonizing agents, and such, and as necessary solubilizing adjuvants, stabilizers, and so on, are added to the compounds of this invention or pharmaceutically acceptable salts thereof.

Methods for producing external formulations is not restricted and can be a conventional method. That is, base materials used for formulation can be selected from various materials ordinarily used for medicaments, quasi-drugs, cosmetics, and such. Specifically, the base materials to be used are, for example, animal fat and vegetable oils, mineral oils, ester oils, waxes, higher alcohols, fatty acids, silicone oils, surfactants, phospholipids, alcohols, polyhydric alcohols, water soluble macromolecules, clay minerals, and purified water. As necessary, pH regulators, antioxidants, chelating agents, antiseptic and antifungal agents, coloring matters, fragrances, and such may also be added. However the base materials of the external formulations of the present invention are not limited thereto. Furthermore, as necessary, components such as those that have a differentiation-inducing effect, blood flow accelerators, fungicides, antiphlogistic agents, cell activators, vitamins, amino acids, humectants, and keratolytic agents can be combined. The above-mentioned base materials are added in an amount that leads to the concentration usually used for external formulations.

The term "salt" as described in the present invention preferably includes, for example, a salt with an inorganic or organic acid, a salt with an inorganic or inorganic base, or a salt with an acidic or basic amino acid. In particular, a pharmaceutically acceptable salt is preferable. Acids and bases form salts at an appropriate ratio of 0.1 to 5 molecules of acid or base to one molecule of the compound.

Preferable examples of a salt with an inorganic acid are a salt with hydrochloric acid, hydrobromic acid, sulfuric acid, nitric acid, and phosphoric acid. Preferably, a salt with an organic acid includes a salt with acetic acid, succinic acid, fumaric acid, maleic acid, tartaric acid, citric acid, lactic acid, stearic acid, benzoic acid, methanesulfonic acid, and p-toluenesulfonic acid.

Preferable examples of a salt with an inorganic base are: an alkali metal salt such as a sodium salt and a potassium salt; an alkaline earth metal salt such as a calcium salt and a magnesium salt; an aluminum salt, and an ammonium salt. Preferably, a salt with an organic base includes a salt with diethylamine, diethanolamine, meglumine, and N,N'-dibenzylethylenediamine.

Preferable examples of a salt with an acidic amino acid are a salt with aspartic acid and glutamic acid, and preferably, a salt with a basic amino acid includes a salt with arginine, lysine, and ornithine.

The compounds of the present invention or salts thereof, or hydrates thereof can be administered orally or parenterally by a conventional method without limitation as to their form. They can be formulated into dosage forms such as tablets, powders, fine granules, capsules, syrups, troches, inhalants, suppositories, injections, ointments, eye ointments, eye drops, nasal drops, ear drops, cataplasms, and lotions. The dose of the pharmaceutical compositions of this invention can be selected appropriately depending on the degree of the symptoms, the patient's age, sex and weight, the dosage form, the type of salt, the specific type of disease, and such.

Compounds of the present invention are administered to a patient in a therapeutically effective dose. Herein, "therapeutically effective dose" refers to the amount of pharmaceutical agent that yields the desired pharmacological result and is effective in the recovery or relief from the symptoms of the patient to be treated. The dose differs markedly depending on the type of disease, the degree of symptoms, the patient's weight, age, sex, sensitivity to the agent. However, the normal adult dosage for one day is about 0.03 mg to 1000 mg, preferably 0.1 mg to 500 mg, more preferably 0.1 mg to 100 mg, when administered from once to several times a day, or from once to several times over several days. The dose for injections is normally, about 1 to 3000 μg/kg, and is preferably about 3 to 1000 μg/kg.

In addition, the present invention relates to a method of screening for antimalarial drugs using the malaria parasite GWT1 gene product. Such a screening method includes, but is not limited to: [1] A binding assay which screens for compounds that compete with a labeled compound to bind with the malaria parasite GWT1 gene product; [2] A GlcN-PI acyltransferase assay system to screen for compounds that inhibit the GlcN-PI acyltransferase activity of the malaria parasite GWT1 gene product; and [3] A GPI-anchored protein detection system in which the malaria parasite GWT1 gene product is expressed in cells, preferably fungal cells, and then the GPI-anchored proteins on the cell surface are detected. The present invention is not limited to these methods, and comprises any method of screening for antimalarial drugs using the malaria parasite GWT1 gene product. The methods [1] to [3] listed above are described below in detail.

[1] A Binding Assay to Screen for Compounds that Compete with a Labeled Compound to Bind with the Malaria Parasite GWT1 Gene Product The two methods according to the present invention are disclosed below, namely (1) a method for preparing the malaria parasite GWT1 gene product (hereinafter referred to as the malaria parasite GWT1 protein) and (2) a method for a binding experiment involving a labeled compound (hereinafter referred to as a binding assay).

(1) Method for Preparing the Malaria Parasite GWT1 Protein

The malaria parasite GWT1 protein is prepared from a cell membrane fraction, preferably from fungal cells, more preferably from cells of S. cerevisiae into which the DNA encoding the malaria parasite GWT1 protein of SEQ ID NO: 2 has been introduced. It is preferable to introduce such a DNA into GWT1 gene-deficient cells. In the binding assay, the prepared membrane fraction may be used without any further treatment, or can be further purified before use. The procedure using S. cerevisiae is described below in detail.

(a) Introduction of the Malaria Parasite GWT1 Gene

The malaria parasite GWT1 gene used in the present invention can be a naturally-occurring gene, or preferably, it can be synthesized based on the amino acid sequence of SEQ ID NO: 2 or 4. The malaria parasite GWT1 gene is very rich in adenine and thymine. Thus, it was predictable that the gene will be difficult to manipulate with ordinary gene recombination techniques, and that gene expression in yeast, cells, and such will be inefficient. Therefore, it is preferable to design a nucleotide sequence in which codons corresponding to each of the corresponding amino acids have been replaced with those that are thought to express efficiently in yeast, cells, and such, and conduct DNA synthesis based on this designed sequence to create an artificial malaria parasite GWT1 gene, which is then used in the experiments described below.

An expression plasmid for the malaria parasite GWT1 is prepared by inserting the malaria parasite GWT1 gene into an S. cerevisiae expression vector, for example, an expression vector prepared by inserting a suitable promoter and terminator, such as the pKT10-derived GAPDH promotor and GAPDH terminator, into YEp352's multi-cloning site (Tanaka et al., Mol. Cell. Biol., 10:4303-4313, 1990). S. cerevisiae (e.g., G2-10 strain) is cultured in an appropriate medium (e.g., YPD medium (Yeast extract-Polypeptone-Dextrose medium)) while shaking at an appropriate temperature (e.g., 30° C.), and the cells are harvested during the late logarithmic growth phase. After washing, the GWT1-expression plasmid is introduced into S. cerevisiae cells using, for example, the lithium-acetate method. This method is described in the User Manual of YEAST MAKER Yeast Transformation System (BD Biosciences Clontech). A malaria parasite GWT1-overexpressing strain and a strain carrying a negative control vector can be obtained by culturing the transformed cells on SD (ura-) medium at 30° C. for two days.

Expression vectors and gene transfer methods for fungal species other than S. cerevisiae have been reported as follows: expression vectors such as pcL for Schizosaccharomyces pombe (S. pombe) and their transfer methods are described by Igarashi et al. (Nature 353:80-83, 1991); expression vectors such as pRM10 for C. albicans and their transfer methods are described by Pla J. et al. (Yeast, 12: 1677-1702, 1996); expression vectors such as pAN7-1 for A. fumigatus and their transfer methods are described by Punt P. J. et al. (GENE, 56: 117-124, 1987); and expression vectors such as pPM8 for C. neoformans and their transfer methods are described by Monden P. et al. (FEMS Microbiol. Lett., 187: 41-45, 2000).

(b) Method for Preparing Membrane Fractions

S. cerevisiae cells in which the malaria parasite GWT1 gene has been introduced are cultured in an appropriate medium (e.g., SD (ura-) liquid medium) while being shaken at an appropriate temperature (e.g., 30° C.). The fungal cells are harvested during the mid-logarithmic growth phase, washed, and then suspended in an appropriate amount (e.g., three times the volume of fungal cells) of homogenization buffer (e.g., 50 mM Tris-HCl, pH 7.5, 10 mM EDTA, Complete™ (Roche)). An appropriate amount of glass beads (e.g., four times the volume of fungal cells) is added to the suspension. The mixture is vortexed and then allowed to stand on ice. This operation is repeated several times to crush fungal cells.

One milliliter of the homogenization buffer is added to the resulting lysate. The mixture is centrifuged, for example at 2,500 rpm for five minutes, to precipitate the glass beads and uncrushed fungal cells. The supernatant is transferred to another tube. The tube is centrifuged, for example at 13,500 rpm for ten minutes, to precipitate a membrane fraction (total membrane fraction) comprising organelles. The precipitate is suspended in 1 ml of binding buffer (e.g., 0.1 M Phosphate buffer, pH 7.0, 0.05% Tween 20, Complete™ (Roche)), and then centrifuged, for example, at 2,500 rpm for one minute to remove unsuspended material. The supernatant is then centrifuged, for example at 15,000 rpm for five minutes. The precipitate is resuspended in 150 to 650 µl of binding buffer to prepare a membrane fraction.

Membrane fractions can be prepared from fungal species other than S. cerevisiae using the method of Yoko-o et al. for S. pombe (Eur. J. Biochem. 257:630-637, 1998); the method of Sentandreu M et al. for C. albicans (J. Bacteriol., 180: 282-289, 1998); the method of Mouyna I et al. for A. fumigatus (J. Biol. Chem., 275:14882-14889, 2000); and the method of Thompson J R et al. for C. neoformans (J. Bacteriol., 181: 444-453, 1999).

Alternatively, the malaria parasite GWT1 protein can be prepared by expressing an E. coli, insect and mammalian cell or the like in non-fungal cells.

When mammalian cells are used, the malaria parasite GWT1 gene is ligated with an over-expression vector containing, for example, the CMV promotor, and then introduced into the mammalian cells. Membrane fractions can then be prepared according to the method of Petaja-Repo et al. (J. Biol. Chem., 276:4416-23, 2001).

Insect cells expressing the malaria parasite GWT1 gene (e.g., Sf9 cells) can be prepared using, for example, a baculovirus expression kit such as the BAC-TO-BAC® Baculovirus Expression system (Invitrogen). Membrane fractions can then be prepared according to the method of Okamoto et al. (J. Biol. Chem., 276:742-751, 2001).

The malaria parasite GWT1 protein can be prepared from E. coli by, for example, ligating the malaria parasite GWT1 gene into an E. coli expression vector such as the pGEX vector (Amersham Biosciences Corp.), and introducing the construct into E. coli such as BL21.

(2) Binding Assay Methods (a) Synthesis of Labeled Compound

The labeled compound is prepared from a compound that has been confirmed to bind to GWT1 proteins. Any compound which can bind to GWT1 proteins can be used. The labeled compound is preferably prepared from the compound described in WO 02/04626, more preferably from compounds according to (1) to (5) described above.

Any labeling method can be used. Preferably, the compound is labeled with a radioisotope, more preferably with $^3$H. The radiolabeled compound can be prepared by typical production methods using a radioactive compound as a starting material. Alternatively, $^3$H labeling can be achieved using an $^3$H exchange reaction.

(b) Confirmation of Specific Binding

The labeled compound is added to the prepared membrane fraction and the mixture is allowed to stand on ice for an appropriate time, for example, one to two hours, while the binding reaction between the labeled compound and the membrane fraction takes place. The membrane fraction is precipitated by centrifuging the mixture, for example at 15,000 rpm for three minutes. The precipitate is resuspended in binding buffer, and the suspension is centrifuged. This is repeated appropriately (twice) to remove any unbound labeled compound. The precipitate is again suspended in binding buffer. The resulting suspension is transferred into a scintillation vial, and a scintillator is added. Radioactivity is measured using a liquid scintillation counter.

The specific binding of the labeled compound to the GWT1 protein can be confirmed by assessing whether binding of the labeled compound is inhibited by adding a large excess of unlabeled compound (ten times or more), and whether the compound binds negligibly to membrane fractions prepared from fungal cells which do not express the GWT1 protein.

(c) Binding Inhibition of a Labeled Compound by a Test Sample

A test sample and the labeled compound are added to the prepared membrane fraction, and the mixture is allowed to stand on ice for an appropriate period of time, for example, one to two hours, while the binding reaction to the membrane fraction takes place. Test compounds used in the present invention's screening method include: a simple naturally-occurring compound, an organic compound, an inorganic compound, a protein, or a peptide, as well as a compound library, an expression product of a genetic library, a cell extract, a cell culture supernatant, a product from fermentative bacteria, an extract of a marine organism, a plant extract, and the like.

The mixture is centrifuged, for example at 15,000 rpm for three minutes to precipitate the membrane fraction. The precipitate is resuspended in binding buffer and the suspension is centrifuged. This is repeated appropriately (twice) to remove any unbound labeled compound. The precipitate is suspended in the binding buffer. The suspension is transferred into a scintillation vial, and scintillator is added thereto. The radioactivity is measured using a liquid scintillation counter.

When the binding of the labeled compound to the membrane fraction is inhibited in the presence of a test sample, the test sample is judged to have the activity of binding to the malaria parasite GWT1 protein.

[2] The GlcN-PI Acyltransferase Assay System for Screening Compounds that Inhibit the GlcN-PI Acyltransferase Activity of the Malaria Parasite GWT1 Protein The transfer of an acyl group to GPI can be detected by the method reported by Costello L. C and Orlean P., J. Biol. Chem. (1992) 267:8599-8603; or Franzot S. P and Doering T. L., Biochem. J. (1999) 340:25-32. A specific example of the method is described below. The following experimental conditions are preferably optimized for each malaria parasite GWT1 protein to be used.

The malaria parasite GWT1 protein is prepared according to the procedure described in Section 1. A membrane fraction comprising the malaria parasite GWT1 protein is added to a buffer which comprises an appropriate metal ion ($Mg^{2+}$, $Mn^{2+}$), ATP, Coenzyme A, and preferably an inhibitor that prevents the consumption of UDP-GlcNAc in other reactions, for example, nikkomycin Z as an inhibitor of chitin synthesis, or tunicamycin as an inhibitor of asparagine-linked glycosylation. A test sample is then added to the mixture and the resulting mixture is incubated at an appropriate temperature for an appropriate period of time (for example, at 24° C. for 15 min).

A GlcN-(acyl)PI precursor (for example UDP-GlcNAc, Acyl-Coenzyme A, and preferably UDP-[$^{14}$C]GlcNAc) which has been appropriately labeled, and preferably radio-labeled, is added to the mixture. The resulting mixture is incubated for an appropriate period of time (for example, at 24° C. for one hour). A mixture of chloroform and methanol (1:2) is added, the resulting mixture is stirred to halt the reaction, and the lipids are extracted. The extracted reaction product is dissolved in an appropriate solvent, preferably butanol. Then, GlcN-(acyl)PI produced in the reaction is separated by a method such as HPLC or thin layer chromatography (TLC), preferably TLC. When TLC is used, the developer can be selected appropriately from, for example, $CHCl_3/CH_3OH/H_2O$ (65:25:4), $CHCl_3/CH_3OH/1M\ NH_4OH$ (10:10:3), and $CHCl_3$/pyridine/HCOOH (35:30:7). A preferred developer is $CHCl_3/CH_3OH/H_2O$ (65:25:4). The separated GlcN-(acyl)PI is quantified using a method appropriate for the label used. When labeled with an radioisotope, the separated GlcN-(acyl)PI can be quantified based on its radioactivity.

When the amount of GlcN-(acyl)PI produced is reduced in the presence of a test sample, the test sample is judged to have the activity of inhibiting acyl group transfer by the malaria parasite GWT1 protein.

[3] A GPI-Anchored Protein Detection System which Comprises Expressing the Malaria Parasite GWT1 Protein in Cells and Detecting the GPI-Anchored Protein on the Cell Surface The ability of a test sample to inhibit the activity of the malaria parasite GWT1 protein can be determined using a GPI-anchored protein detection system that comprises expressing the GWT1 protein in cells, preferably fungal cells, and then detecting the GPI-anchored protein on the cell surface. The fungi of the present invention are those belonging to Zygomycota, Ascomycota, Basidiomycota, and Deuteromycete, and preferably pathogenic fungi, *Mucor, Saccharomyces, Candida, Cryptococcus, Trichosporon, Malassezia, Aspergillus, Trichophyton, Microsporum, Sporothrix, Blastmyces, Coccidioides, Paracoccidioides, Penicillinium*, and *Fusarium*, more preferably *C. albicans, C. glabrata, C. neoformans*, and *A. fumigatus*, and even more preferably, yeast. Such yeasts include *S. cerevisiae* and *S. pombe*. The method for introducing into the above-described fungal cells an expression vector containing inserted DNA encoding the malaria parasite GWT1 protein is known to those skilled in the art.

When the malaria parasite GWT1 protein is expressed in fungal cells, the amount of GPI-anchored protein transported to the fungal cell wall can be determined by the following methods: (1) by using a reporter enzyme; (2) by using an antibody that reacts with the surface glycoprotein of fungal cell walls; (3) by using the protein's ability to adhere to animal cells; or (4) by observing fungal cells under a light microscope or electron microscope.

The methods of (1) to (4) have been disclosed in WO 02/04626, which is described specifically in Examples of this invention. The methods (1) to (4), and preferably a combination of these methods (1) to (4), can determine whether a test sample inhibits the transport of the GPI-anchored protein onto the cell wall, or the expression of the GPI-anchored protein on the fungal cell surface.

Hereinafter, the methods of (1) to (4) will be described.

(1) A Method Using a Reporter Enzyme

The process that transports GPI-anchored proteins to the cell wall can be quantified using a tracer experiment such as one where a GPI-anchored protein is labeled with a radioactive isotope, the fungal cell wall fraction is obtained, and immunoprecipitated using an antibody against the GPI-anchored protein. Alternatively, quantification can be more readily performed as follows: the C-terminal sequence, which is considered to function as a transport signal and is commonly observed among GPI-anchored proteins, can be expressed as a fusion protein with an easily measurable enzyme (reporter enzyme), the fungal cell wall fraction can be obtained, and a reporter system that measures the enzyme activity of each fraction can be used (Van Berkel M A A et al., FEBS Letters, 349: 135-138, 1994). Hereinafter, a method which uses a reporter enzyme will be described, but in the present invention such methods are not to be construed as being limited thereto.

First, the reporter gene is constructed and introduced into fungi. The reporter gene is constructed by linking a promoter sequence that functions in fungi with DNAs that respectively encode a signal sequence, a reporter enzyme, and a GPI-anchored protein C-terminal sequence in such a way that the reading frames match. Examples of the promoter sequence are GAL10 and ENO1. Examples of the signal sequence include α-factor, invertase, and lysozyme. Examples of reporter enzymes are β-lactamase, lysozyme, alkaline phosphatase, and β-galactosidase. Green Fluorescence Protein (GFP), which has no enzyme activity but can be easily detected, can also be used. GPI-anchored protein C-terminal sequences include the α-agglutinin C-terminal sequence, the CWP2 C-terminal sequence, and so on. Furthermore, it is preferable to insert an appropriate selection marker, such as LEU2 and URA3, into the vector comprising the constructed reporter gene.

The constructed reporter gene is inserted into fungi using an appropriate method, such as the lithium acetate method (Gietz D et al., Nucl. Acids Res. 20: 1425, 1992). The fungi are then cultured, as necessary, using a method that suits the selection marker (e.g. using Leu medium for LEU2 and Ura⁻ medium for URA3), and then fungi into which the DNA has been introduced are selected.

The effect of a test sample on the transport of GPI-anchored proteins to the cell wall is examined by the following method:

The reporter gene-introduced fungi are cultured under appropriate conditions, for example at 30° C. for 48 hours, in the presence of a test sample. After culturing, the culture supernatant is centrifuged, and the reporter enzyme activity of the culture supernatant fraction is measured. The resulting cell fraction is washed, the cell wall components are separated using an appropriate method, such as degrading the cell wall glucan with glucanase, and then the reporter enzyme activity of the cell wall fraction and cytoplasmic fraction is measured. The assay can be simply carried out by using centrifugation to determine the amount of reporter enzyme in the cell fraction, then without washing the cells, using proportional calculations to determine the amount of reporter enzyme derived from the culture supernatant fraction that remains in the cell fraction, and subtracting this from the amount of reporter enzyme of the cell fraction.

If the test sample exhibits the activity of increasing reporter enzyme activity within the culture supernatant fraction (activity per cell), or the activity of decreasing the reporter enzyme activity in the cell wall fraction (activity per cell), the test sample is judged to have influenced the transport process of GPI-anchored proteins to the cell wall.

(2) A Method Using an Antibody That Reacts With the Surface Glycoprotein of Fungal Cell Walls A test sample's ability to influence the expression of a GPI-anchored protein at the fungal surface layer can be determined by quantification using an antibody that reacts with that GPI-anchored protein in the fungal cell wall.

Antibodies can be obtained by predicting the antigenic determinant using the amino acid sequence of, for example, a GPI-anchored protein such as α-agglutinin, Cwp2p, or Als1p (Chen M H et al., J. Biol. Chem., 270:26168-26177, 1995; Van Der Vaat J M et al., J. Bacteriol., 177:3104-3110, 1995; Hoyer L L et al., Mol. Microbiol., 15:39-54, 1995), and then synthesizing the peptide of that region, binding it to an antigenic substance such as a carrier protein, and then immunizing a rabbit or such to obtain polyclonal antibodies, or a mouse or such to obtain a monoclonal antibody. A rabbit polyclonal antibody against the Als1p peptide is preferable.

In an alternative method, a monoclonal antibody against a GPI-anchored protein may be obtained by immunizing mice and such with fungi, preferably fungi which overexpress a GPI-anchored protein such as α-agglutinin, Cwp2p, and Als1p, (in some cases by immunizing further with a partially purified GPI-anchored protein), and then using ELISA, Western blot analysis, and so on to select resultant clones based on the antibody that they produce.

The following method can be used to determine the influence of a test sample on the process that transports a GPI-anchored protein to the cell wall, and on the amount of protein derived from that GPI-anchored protein in the cell wall.

Fungi are cultured in the presence of a test sample under appropriate conditions such as 30° C. for 48 hours. The cultured fungi are collected by centrifugation and the cells are disrupted, preferably using glass beads. The washed, disrupted cells are preferably subjected to centrifugal extraction with SDS, and then the precipitate is washed. After extraction, the disrupted cells are treated with an enzyme that degrades glucan, preferably glucanase, and the centrifuged supernatant thereof is the GPI-anchored protein sample.

The anti-Als1p peptide antibody is coated onto a 96-well plate by overnight incubation at 4° C. The plate is washed with a washing solution, preferably PBS comprising 0.05% Tween 20 (PBST), and blocking is carried out using a reagent that blocks the non-specific adsorption sites of the 96-well plate, preferably a protein such as BSA or gelatin, more preferably BlockAce (Dainippon Pharmaceutical Co., Ltd.). The plate is again washed with a washing solution, preferably PBST, and an appropriately diluted GPI-anchored protein sample is added. The reaction is then carried out for an appropriate time such as two hours at room temperature. After washing with a washing solution, preferably with PBST, an antibody against the enzyme-labeled *C. albicans*, preferably HRP-labeled anti-*Candida* antibody, is reacted for an appropriate time such as two hours at room temperature. The labeling method may be enzyme labeling or radioactive isotope labeling. After washing with a washing solution, preferably PBST, the amount of Alslp in the GPI-anchored protein sample is calculated by a method appropriate to the type of label, i.e. for an enzyme label, by adding a substrate solution and then, upon stopping the reaction, measuring absorbance at 490 nm.

(3) A method Using the Ability to Adhere to Animal Cells

The test sample's influence on the expression of a GPI-anchored protein on the fungal surface can be determined by measuring the activity of that GPI-anchored protein in the fungal cell wall, and preferably by measuring the ability of fungi to adhere to animal cells and the like. In addition to the activity of Als1p, Hwp1p and such in adhesion to animal cells, GPI-anchored protein activity includes that of α-agglutinin in mating, of Flo1p in yeast aggregation, and so on. Hereinafter, a method using the ability of fungi to adhere to animal cells will be described in detail, but the present invention is not to be construed as being limited thereto.

A fungus with the ability to adhere to cells is used, and this fungus is preferably *C. albicans*. For mammalian cells, cells that adhere to the fungus, preferably intestinal epithelial cells, are used. The mammalian cells are cultured and fixed using an appropriate method, such as ethanol fixation. The test sample and the fungi are incubated for an appropriate time such as 48 hours at 30° C., then inoculated and cultured for a set time, for example, one hour at 30° C. The culture supernatant is then removed, and the cells are washed with a buffer and overlaid with agar media such as Sabouraud Dextrose Agar Medium (Becton Dickinson Company, Ltd.). After culturing at 30° C. overnight, the number of colonies is counted, and the adhesion rate is calculated.

If, when compared to fungi not treated with the compound, a test sample is observed to have the activity of decreasing the number of colonies formed by cell adhesion, that test sample is judged to have influenced the process that transports GPI-anchored proteins to the cell wall.

(4) A Method for Observing Fungi Using an Electron Microscope or an Optical Microscope The influence of a test sample on the expression of the GPI-anchored protein in the fungal surface can be determined by observing the structure of the fungal cell wall using an electron microscope.

In the presence of a test sample, a fungus such as *C. albicans* is cultured for a certain period of time, for example, 48 hours at 30° C., and its ultrafine morphological structure is observed using a transmission electron microscope. Herein, observation using a transmission electron microscope can be carried out, for example by the method according to the Electron Microscope Chart Manual (Medical Publishing Center). The flocculent fibrous structure of the outermost layer of a fungal cell has a high electron density and is observable by transmission electron microscope. This structure is not influenced by other existing antifungal agents and is considered to be a surface glycoprotein layer, including GPI-anchored proteins as its constituents. When this structure disappears, leaving only a slight layer with a high electron density, the test sample is judged to have influenced the process that transports GPI-anchored proteins to the cell wall, compared to untreated cells.

When observation under both a transmission electron microscope and an optical microscope reveals greatly swollen fungal cells and inhibited budding (division), the test sample is judged to have an influence on the cell wall.

The present invention also provides a method for treating malaria, which comprises the step of administering a compound that inhibits the activity of a GWT1 protein a malaria parasite. Such a compound includes the compounds described in WO 02/04626 (for example, the compounds described herein in (1)-(5)).

The nucleotide sequence for the natural PfGWT1 protein is characterized by an exceedingly high AT content (80.41%), and thus codon usage is biased. In addition, the gene contains sequence stretches comprising six or more consecutive A residues at 23 separate positions, and these sequence stretches may serve as pseudo-poly(A) sites, thus producing truncated proteins. Because of the features described above, the gene was only expressed poorly in yeast, and very difficult to amplify using PCR or to replicate in *E. coli*. It was also difficult to determine the nucleotide sequence. However, the present inventors succeeded in expressing the PfGWT1 protein with a high efficiency by using a degenerate mutant of the DNA (SEQ ID NO: 5), with a lower AT content than the DNA encoding the PfGWT1 protein. The inventors also revealed that the introduction of the degenerate mutant DNA can rescue the phenotype of GWT1-deficient yeast. This finding suggests that the GPI synthase of a malaria parasite is interchangeable with that of a fungus such as yeast.

The AT content of the gene encoding the malaria parasite GPI synthase is, for example, 79.35% for GPI8 and 77.89% for the GPI13 of *P. falciparum*. These AT contents are as high as that of PfGWT1. It is predicted that most *P. falciparum* genes are hardly expressed in other species, because the average AT content over the translated regions of the *P. falciparum* genome is 76.3%. The present inventors succeeded in expressing a degenerate mutant of the DNA with a lower AT content than that of the DNA encoding the PfGWT1 protein, in yeast. Hence, the malaria parasite GPI synthase can be expressed in a host other than malaria parasites by using such a degenerate DNA mutant. Furthermore, GPI-deficient yeast and GWT1-deficient yeast are known to exhibit similar phenotypes, including the characteristic of lethality and such. Thus, the phenotype of the GPI synthase gene-deficient fungus can be rescued by using the degenerate mutant DNA described above.

The phenotype of the GPI synthase gene-deficient fungus into which the degenerate mutant DNA described above has been introduced depends on the activity of the malaria parasite GPI synthase. Accordingly, compounds that inhibit the activity of the malaria parasite GPI synthase can be selected by screening using the phenotype of the GPI synthase gene-deficient fungus as an index. Thus, antimalarial drugs targeting the GPI biosynthesis pathway can be selected without actually using the malaria parasites themselves.

The present invention provides a degenerate mutant DNA encoding a protein that has the activity of rescuing the phenotype of a GPI synthase gene-deficient fungus, and which has an AT content lower than that of the original DNA encoding the protein involved in the biosynthesis of GPI. Such a DNA can be used in the screening method of the present invention.

As used herein, the term "AT content" refers to the content of adenine and thymine in the entire nucleotide sequence of the coding region of the GPI synthase gene. The AT content in the degenerate mutant DNA of the present invention preferably ranges from 50% to 70%, more preferably from 53% to 65%, and still more preferably from 55% to 62%.

The phenotype of the GPI synthase gene-deficient fungus includes temperature sensitivity (preferably, sensitivity to high temperatures) and lethality.

The proteins of the present invention involved in the biosynthesis of GPI in malaria parasites include GWT1, GPI1, GPI8, GPI3/PIG-A, GPI10/PIG-B, YJR013W/PIG-M, GPI13/PIG-O, GAA1/GAA-1, DPM1, GPI2, GPI15, YDR437W, GPI12, MCD4, GPI11, GPI7, GPI17, GPI16, CDC91, DPM2, DPM3, and SL15. Of the proteins indicated above, GPI1 and GPI8 have been found to be present in malaria parasites, and GPI3/PIG-A, GPI10/PIG-B, YJR013W/PIG-M, GPI13/PIG-O, GAA1/GAA-1, and DPM1 have been suggested to be present in malaria parasites (Delorenzi et al., Infect. Immun. 70: 4510-4522, 2002). The nucleotide sequences of GWT1, GPI1, GPI8, GPI3/PIG-A, GPI10/PIG-B, YJR013W/PIG-M, GPI13/PIG-O, GAA1/GAA-1, and DPM1 of *P. falciparum* are shown in SEQ ID NO: 1 and the even sequence identification numbers in SEQ ID NOs: 6-21, respectively. Each corresponding amino acid sequence is shown in SEQ ID NO: 2 and the odd sequence identification numbers in SEQ ID NOs: 6-21. In addition, the nucleotide sequence of *P. vivax* GWT1 is shown in SEQ ID NO: 3, and the corresponding amino acid sequence is shown in SEQ ID NO: 4. Using a method known to those skilled in the art, for example, a method using hybridization or PCR, GWT1, GPI1, GPI8, GPI3/PIG-A, GPI10/PIG-B, YJR013W/PIG-M, GPI13/PIG-O, GAA1/GAA-1, or DPM1 of other malaria parasites can be cloned using DNA comprising any one of the nucleotide sequences shown in SEQ ID NO: 1 and 3, and the even-numbered SEQ ID NOs: 6-21.

Furthermore, GPI synthase genes other than GWT1, GPI1, GPI8, GPI3/PIG-A, GPI10/PIG-B, YJR013W/PIG-M, GPI13/PIG-O, GAA1/GAA-1, and DPM1 of malaria parasites can be cloned by using yeast or human GPI synthase genes. The nucleotide sequences of GPI2, GPI15, YDR437W, GPI12, MCD4, GPI11, GPI7, GPI17, GPI16, and CDC91 of yeast (S. cerevisiae) are shown in the even sequence identification numbers in SEQ ID NOs: 22-41 respectively; and each corresponding amino acid sequence is shown in the odd sequence identification numbers in SEQ ID NOs: 22-41. In addition, the nucleotide sequences of human DPM2, DPM3, and SL15 are shown in the even sequence identification numbers in SEQ ID NOs: 42-47 respectively; and each corresponding amino acid sequence is shown in the odd sequence identification numbers in SEQ ID NOs: 42-47.

The production of a degenerate mutant DNA encoding a protein involved in the biosynthesis of the GPI of malaria parasites, and with a lower AT content than that of the original DNA, consists of two steps: design, and synthesis. In the design step, the amino acid sequence of a protein of interest is first reverse-translated and then possible codons for each amino acid residue are listed. Reverse translation can be achieved by using commercially available gene analysis software (for example, DNASIS-Pro; Hitachi Software Engineering Co., Ltd). Of the codons listed, those meeting the purpose (for example, codons whose AT content is lower and codons frequently used in the host to be used for gene expression) are selected for each amino acid. The degenerate mutant DNA can be designed by rearranging the amino acid sequence of the protein of interest using these selected codons.

The DNA thus designed can be synthesized by a method known to those skilled in the art. The degenerate mutant DNA of the present invention can be synthesized based on the designed nucleotide sequence by, for example, using a commercially available DNA synthesizer.

The present invention also provides vectors in which the above-described degenerate mutant DNA has been inserted, and transformants (preferably GPI synthase gene-deficient fungi) that retain the DNA or the vector in an expressible state. The vector and the host can be those described above.

As used herein, the expression "deficient in the GPI synthase gene" means that the functional product of the gene is not expressed, or that the expression level is decreased. The GPI synthase gene-deficient fungus of the present invention can be prepared by disrupting the GPI gene. The disruption can be achieved by inserting DNA unrelated to the gene, for example a selection marker, based on homologous recombination technology, and the like. More specifically, such a mutant fungus can be prepared by introducing into yeast a selection marker cassette which comprises the his5 gene or the kanamycin resistance gene of *S. pombe* (Longtine et al., Yeast, 14: 953-961, 1998) amplified with primers, each of which comprises a nucleotide sequence homologous to a portion of the gene (ranging from 50 to 70 nucleotides).

The GPI synthase gene-deficient fungus of the present invention includes, for example, the GWT1 temperature-sensitive mutant strain gwt1-20, GPI7 disruptant strain, GPI8 mutant strain gpi8-1, and GPI10 temperature-sensitive mutant strain per13-1.

A GPI synthase gene-deficient fungus which has been transformed with the degenerate mutant DNA of the present invention can be prepared by introducing into a fungus a vector into which the degenerate mutant DNA has been inserted. pRS316, YEp351, or such can be used as the vector for *S. cerevisiae*, and pcL, pALSK, or such can be used as the vector for *S. pombe*.

The present invention also provides a method of screening for antimalarial drugs, which comprises using GPI synthase gene-deficient fungi described above.

In such a method, the first step comprises contacting a test sample with a GPI synthase gene-deficient fungus that has been transformed with degenerate mutant DNA with a lower AT content than the DNA encoding a protein involved in the biosynthesis of GPI of malaria parasites. The "contact" can be achieved by adding a test sample to the culture of the above-mentioned fungus. When the test sample is a protein, a vector comprising DNA encoding the protein can be introduced into the above-mentioned fungus.

In the method of the present invention, the next step comprises measuring the degree of growth of the above-mentioned fungus. More specifically, the fungus is inoculated under typical culture conditions, specifically, the fungus is inoculated onto a liquid culture medium such as Yeast extract-polypeptone-dextrose medium (YPD medium) or onto an agar plate, and then incubated at 25 to 37° C. for 4 to 72 hours. Thus GPI synthase gene-deficient fungus transformed with the degenerate mutant DNA of the present invention can be assessed for growth. The degree of growth can also be determined using the turbidity of the culture liquid, the number of colonies, or the size or color of the spots formed on the agar plate as an index. In the method of the present invention, the next step comprises selecting compounds that inhibit the growth of the above-mentioned fungus.

In an alternative method, the first step comprises contacting a test sample with a GPI synthase gene-deficient fungus in which the above-described degenerate mutant DNA has been introduced. The next step comprises determining the amount of GPI-anchored protein transported onto the yeast cell wall. The detection method includes: (1) methods using a reporter enzyme; (2) methods using an antibody that reacts with a surface glycoprotein on the fungal cell wall; (3) methods using the ability to adhere to animal cells; and (4) methods using a light microscope or an electron microscope to observe the fungi. In the method of the present invention, the next step comprises selecting a sample that decreases the amount of GPI-anchored protein transported to the cell wall.

The present invention provides a method of screening for antimalarial drugs using a protein involved in the biosynthesis of GPI, which is prepared using a degenerate mutant DNA of the present invention. Such methods include, for example, a binding assay system where screening is carried out to select compounds that bind to a protein involved in GPI biosynthesis in competition with a labeled compound bound to the protein. Specifically, a degenerate mutant DNA of the present invention is introduced into the GPI synthase gene-deficient fungus, the protein encoded by the DNA is expressed in the fungus, and the expressed protein is prepared. The prepared protein is then contacted with a test sample and with a labeled compound that can bind to the protein. In the next step, the labeled compound bound to the protein is detected, and test samples that decrease the amount of labeled compound bound to the protein are selected.

The present invention also provides an assay system for GlcN-PI acyltransferase. Such a system comprises using a GWT1 protein which is prepared using a DNA encoding a protein that has the activity of complementing the phenotype of GWT1-deficient yeast, which the DNA is a degenerate mutant of a DNA encoding a malaria parasite GWT1 protein that has a lower AT content than the original DNA. Specifically, the degenerate mutant DNA is introduced into GWT1-deficient fungus, the protein encoded by the degenerate mutant DNA is expressed in the fungus, and the expressed protein is prepared. This protein is then contacted with a test sample, GlcN-(acyl)PI is detected, and a test sample that decreases the amount of GlcN-(acyl)PI is selected.

Any patents, patent applications, and publications cited herein are incorporated by reference in their entireties.

If one copy of the GWT1 gene was disrupted, only half of the spores grew. Thus, the ratio of [colony-forming spots]: [spots exhibiting no growth] is 2:2 in such cases. In the columns marked with an arrow, the lethal phenotype of the gwt1 disruptant was complemented by the introduced opfGWT1, and hence all four spots grew, each forming a colony.

Figure 2:
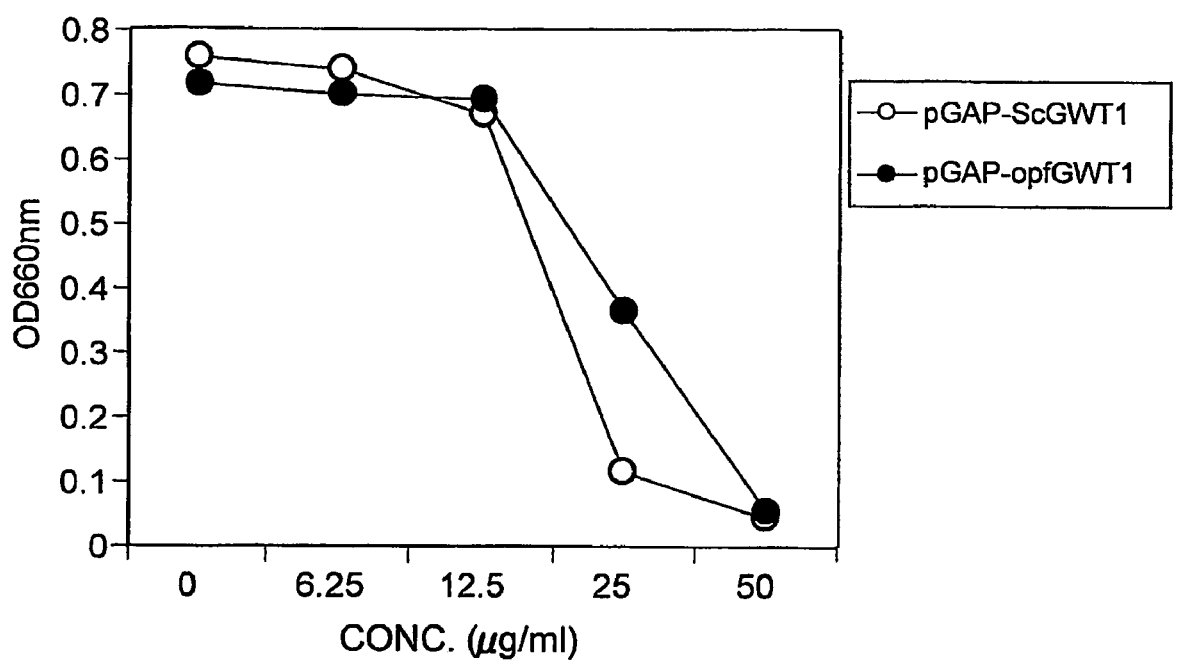

FIG. 2 depicts a diagram showing the inhibitory activity of a compound with respect to the growth of yeast expressing the opfGWT1 gene. Either the yeast GWT1 gene or opfGWT1 gene was expressed in GWT1 gene-disrupted yeast.

A compound having the activity of inhibiting the GWT1-dependent growth of yeast also showed inhibitory activity with respect to the opfGWT1-dependent growth of yeast in which opfGWT1 was expressed.

Figure 3:
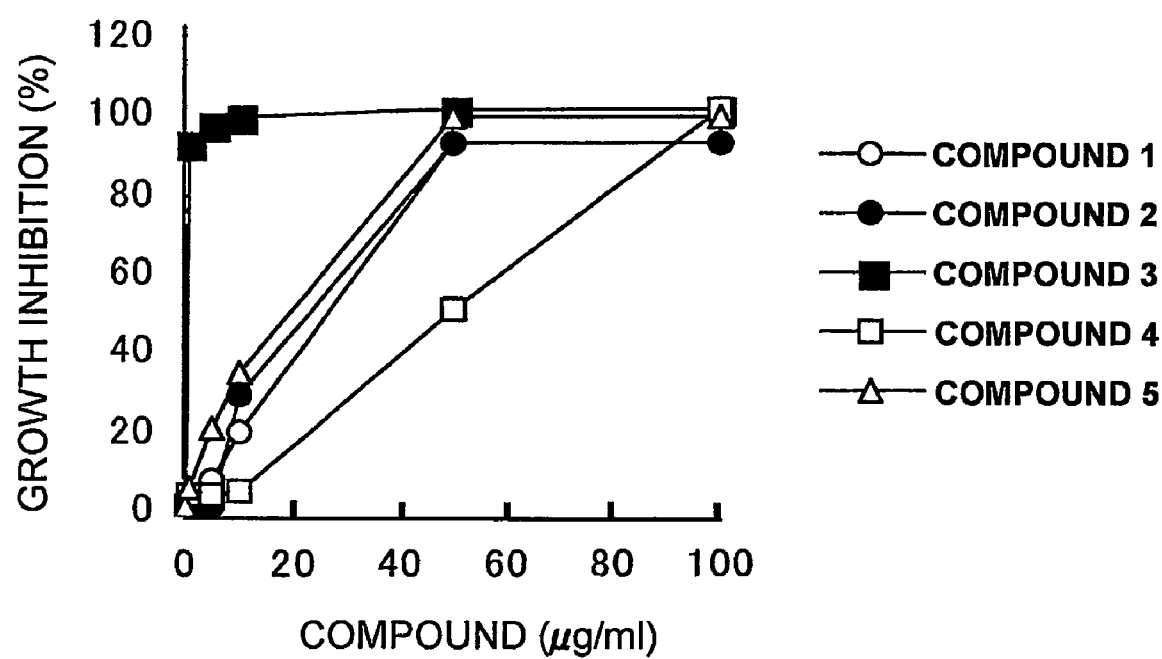

FIG. 3 depicts a diagram showing antimalarial activity. Human red blood cells were infected with *P. falciparum*. A GWT1-inhibiting compound was added to these red blood cells, and inhibition of malaria parasite infection was determined.

All five compounds exhibiting antifungal activity also inhibited the malaria parasite infection of red blood cells.

3D7 strain) as a template. The 5' half and 3' half of the PfGWT1 gene were prepared separately, and the two halves were assembled at an XbaI (TCTAGA) restriction enzyme site. Thus, the full-length PfGWT1 gene was prepared. In addition, restriction enzymes sites outside the coding region were included, thus allowing insertion into an expression vector.

(2) The 5' half of the PfGWT1 gene was amplified by PCR using *P. falciparum* genomic DNA as a template and the primers pf152F (SEQ ID NO: 48) and pf136R (SEQ ID NO: 49). The 3' half was amplified by the same procedure described above, using the primers pf137F (SEQ ID NO: 50) and pf151R (SEQ ID NO: 51). The DNA fragments amplified were subcloned into the pT7-Blue vector (Novagen), and the nucleotide sequences of the inserts were sequenced to confirm homology to SEQ ID NO: 1. Clones containing the 5' half of the PfGWT1 gene were named PF15-5 clones. Clones containing the 3' half were named PF20-9 clones.

(3) Using PCR, cleavage sites for restriction enzymes were added outside the coding region to enable the PfGWT1 gene to be inserted into an expression vector. An EcoRI cleavage site was added to the 5' half by PCR using PF15-5 as a template and the primers pf154FE (SEQ ID NO: 52) and pf157R (SEQ ID NO: 53). The amplified DNA fragment was subcloned into the pT7-Blue vector (Novagen) to prepare the clone pT7-plasmN2. Likewise, the 3' half was amplified by PCR using PF20-9 as a template and the primers pf168BK (SEQ ID NO: 54) and pf155RK (SEQ ID NO: 55). The amplified DNA fragments were subcloned to prepare pT7-plasmBK5 clones.

(4) The full-length PfGWT1 gene was prepared by the procedure described below. The yeast expression vector YEp352GAPII was digested with the restriction enzymes EcoRI and KpnI. The EcoRI-XbaI fragment (about 1500 bp) derived from pT7-plasmN2, and the XbaI-KpnI fragment (about 1100 bp) derived from pT7-plasmBK5, were inserted into the vector at a cleaved site. The expression vector YEp352GAPII-PfGWT1 containing the full-length PfGWT1 was then constructed.

| [pf152F] | ATGACAATGTGGGGAAGTCAACGGg | (SEQ ID NO: 48) |
|---|---|---|
| [pf136R] | TGTGTGGTTACCGTTCTTTGAATACATAGA | (SEQ ID NO: 49) |
| [pf137F] | ATAGAAAATGATTTATGGTACAGCTCAAA | (SEQ ID NO: 50) |
| [pf151R] | AGACCAAATTAATTATGCCTTTACATGTAC | (SEQ ID NO: 51) |
| [pf154FE] | agaattcaccATGAGCAACATGAATATACTTGCGTATCTT | (SEQ ID NO: 52) |
| [pf157R] | GAAATTCCAATGTATTCCATATTCACTTAT | (SEQ ID NO: 53) |
| [pf168BK] | AAGATCTAATACATTAAAACATTTTAGATTAATGAATATGTG | (SEQ ID NO: 54) |
| [pf155RK] | aggtaccGTACACTCCACTCTATGATGATCATTC | (SEQ ID NO: 55) |

BEST MODE FOR CARRYING OUT THE INVENTION

Herein below, the present invention will be specifically described using Examples, but it is not to be construed as being limited thereto.

Example 1

*P. falciparum* GWT1 (PfGWT1)

(1) The nucleotide sequence of *P. falciparum* GWT1 (PfGWT1) (SEQ ID NO: 1) has been disclosed in the database of the *P. falciparum* genome. The PfGWT1 gene was cloned by PCR using genomic DNA purified from *P. falciparum* (the

Example 2

A Fully Synthetic PfGWT1 Gene

The adenine and thymine (AT) proportion is exceedingly high (80% or higher) in *P. falciparum* DNA, and thus routine biological techniques (PCR, *E. coli*-based gene engineering, expression systems for recombinant proteins, and so on) are often unavailable (Sato and Horii; Protein, Nucleic acid, and Enzyme Vol. 48, 149-155, 2003). Likewise, the AT content of PfGWT1 DNA was 80.41% including many consecutive A or T stretches. Thus, the gene was predicted to be difficult to replicate and express as a protein in yeast. Indeed, when native PfGWT1 ligated with a yeast overexpression vector was introduced into GWT1 disrupted yeast, the PfGWT1 did not rescue the lethal phenotype of the GWT1 disruptant at all. To reduce AT content, codons were replaced with synonymous codons without changing the original amino acid sequence.

The codon substitution was carried out based on the nucleotide sequence of *P. falciparum* GWT1 (SEQ ID NO: 1) disclosed in the *P. falciparum* genome database. The resulting nucleotide sequence was named "optimized PfGWT1 (opfGWT1)" (SEQ ID NO: 5).

The sequence described above was designed to include additional sequences outside the coding region; namely an EcoRI cleavage site sequence (GAATTC, at the 5' end), Kozak's sequence (ACC, at the 5'end), and a KpnI cleavage site sequence (GGTACC, at the 3' end). The synthesis of the resulting sequence was consigned to Blue Heron Inc. in the U.S.A. These additional restriction enzyme sites were used to ligate the fully synthetic opfGWT1 into the YEp352GAPII vector to construct an overexpression plasmid for opfGWT1. The construct was introduced into diploid cells (WDG2) in which only a single copy of the GWT1 gene had been disrupted. The resulting transformants were cultured on plates containing a sporulation medium to form spores for tetrad analysis.

Figure 1:
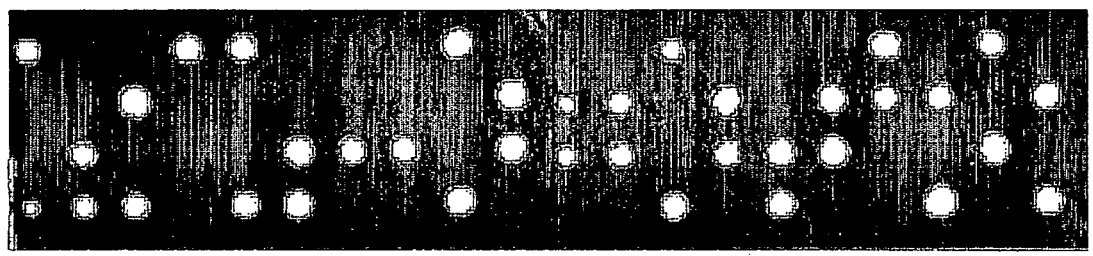
FIG. 1 depicts photographs showing the results of tetrad analysis. The gwt1-disrupted strain became viable after the introduction of the opfGWT1-overexpressing plasmid. The four spores derived from a single diploid cell were spotted vertically.
Figure 1:
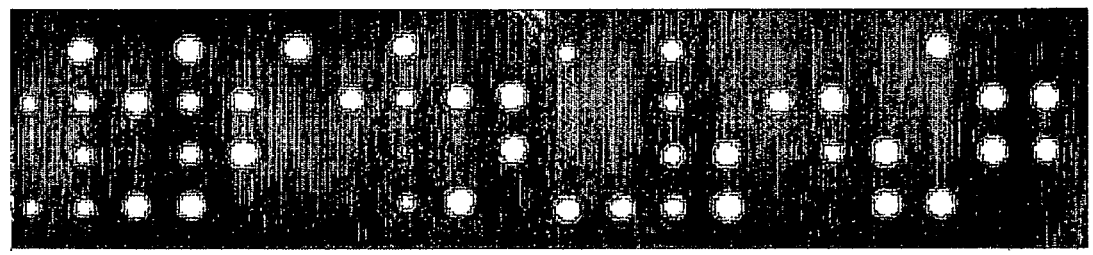
Figure 1:

The AT content of the newly designed codon-modified opfGWT1 was reduced to 61.55%. The results of tetrad analysis are shown in FIG. 1. The gwt1-disrupted strain became viable after introduction of the opfGWT1 overexpression plasmid. The findings described above indicate that the PfGWT1 gene can be expressed in yeast cells when its AT content is reduced by codon modification.

Example 3

An Assay for Antimalarial Activity Using opfGWT1-Expressing Yeast

A screening system for compounds having antimalarial activity was constructed using opfGWT1-expressing yeast.

An expression cassette was constructed by inserting the *S. cerevisiae* GWT1 terminator, and the *S. cerevisiae* GAPDH promoter and multi-cloning site into the SacI-KpnI site of the single-copy vector pRS316. *S. cerevisiae* GWT1 and opfGWT1 were inserted into the multi-cloning site to prepare pGAP-ScGWT1 and pGAP-opfGWT1 plasmids, respectively. These plasmids were introduced into the GWT1 disruptant. Serial two-fold dilutions of compound (1) were prepared using YPAD to make the highest final concentration 50 µg/ml. A 50 µl aliquot of the diluted compound was added to each well of a 96-well plate. Overnight cultures of yeast cells comprising each plasmid were diluted 1000-fold and then a 50 µl aliquot of the dilution was added to each well. The plates were incubated at 30° C. for two days, and then culture turbidity was determined at 660 nm (FIG. 2 and Table 1).

TABLE 1

|  | 0 | 6.25 | 12.5 | 25 | 50 |
| --- | --- | --- | --- | --- | --- |
| pGAP-ScGWT1 | 0.7560 | 0.7370 | 0.6670 | 0.1140 | 0.0420 |
| pGAP-opfGWT1 | 0.7150 | 0.6990 | 0.6910 | 0.3630 | 0.0530 |

Although the GWT1 disruptant was nonviable, the strain became viable after introduction of each plasmid (as shown at 0 µg/ml of compound concentration). The growth of ScGWT1-expressing yeast was inhibited by compound (1), a GWT1-specific inhibitor. The use of the compound at 25 µg/ml resulted in about 85% inhibition of growth. When the compound was used at 50 µg/ml, the yeast was completely nonviable. The growth of opfGWT1-expressing yeast was also inhibited by compound (1). The use of the compound at 25 µg/ml resulted in about 50% inhibition of growth. When the compound was used at 50 µg/ml, the yeast was completely nonviable. Since growth of opfGWT1-expressing yeast depends on the activity of the introduced opfGWT1, growth inhibition can be attributed to the inhibition of the opfGWT1 function by compound (1). These findings suggest that compounds with *P. falciparum* GWT1-specific inhibitory activity GWT1 can be identified by screening compounds using this assay system.

Example 4

Antimalarial Activity

Representative compounds (1) to (5), that inhibit yeast GWT1, were assayed for antimalarial activity using a red blood cell culture system.

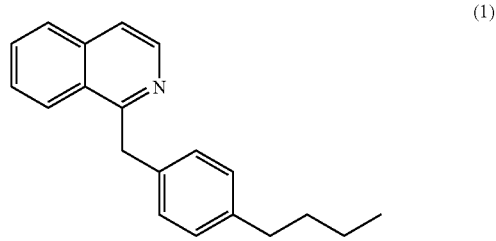

compound (1): 1-(4-butyl benzyl)isoquinoline

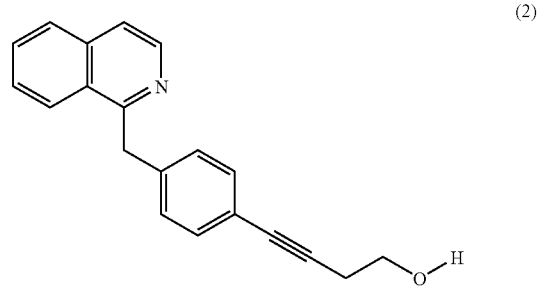

compound (2): 4-[4-(1-isoquinolyl methyl)phenyl]-3-butyne-1-ol

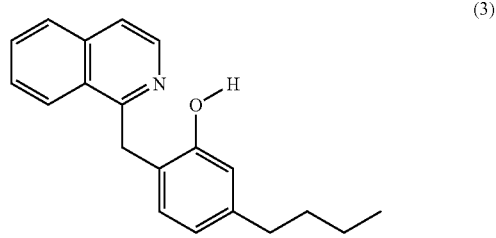

compound (3): 5-butyl-2-(1-isoquinolyl methyl)phenol (4)

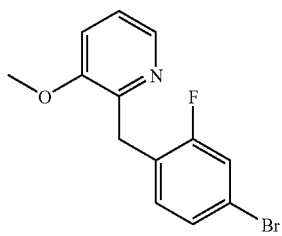

compound (4): 2-(4-bromo-2-fluorobenzyl)-3-methoxypyridine (5)

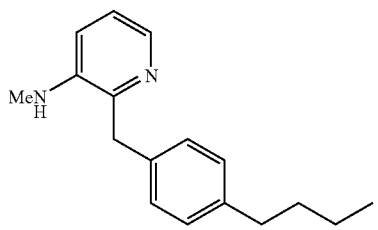

compound (5): N-[2-(4-butyl benzyl)-3-pyridyl]-N-methylamine

Specifically, a test compound was dissolved in 100% DMSO, diluted with a medium, and an 80 μl aliquot of the dilution was added to each well of a 96-well culture plate. $P.$ $falciparum$ FCR3 strain was pre-cultured in RPMI1640 medium containing 10% human serum at 37° C., and then 20 μl of the cultured cells (containing 10% red blood cells) was added to each well. At this time, 0.47% of red blood cells were infected. After culturing under 5% $O_2$, 5% $CO_2$, and 90% $N_2$ at 37° C. for 48 hours, the malaria parasites were stained using Giemsa staining. The number of protozoan-infected red blood cells was determined in order to estimate infection rate (FIG. 3). As a result, compound (3) was revealed to have strong antimalarial activity. The other four compounds also showed antimalarial activity. Compound (4) exhibited the lowest activity. Therefore, compounds inhibiting yeast GWT1 include compounds which have the activity of inhibiting $P. falciparum$ GWT1, suggesting that antimalarial drugs can be synthesized based on such compounds.

INDUSTRIAL APPLICABILITY

The present invention succeeded in producing fungi that express malaria parasite GWT1. Using such fungi, antimalarial drugs targeting the pathway of GPI biosynthesis can be screened without using malaria parasites.

To date, no attempt has been made to express a malaria parasite gene in fungal cells and screen substances which inhibit the function of that gene. The methods of the present invention remove the need to actually using malaria parasites themselves, and thus this method proves the possibility of entirely new screening methods for drug discovery using comparative genomics in the post-genome era.

The invention claimed is:

1. An isolated DNA according to any one of (a) to (e), which encodes a protein of a malaria parasite having GlcN-PI acyltransferase activity:
   (a) a DNA encoding a protein comprising the amino acid sequence of SEQ ID NO: 2 or 4,
   (b) a DNA consisting of the nucleotide sequence of SEQ ID NO: 1 or 3,
   (c) a DNA hybridizing to DNA consisting of the nucleotide sequence of SEQ ID NO: 1 or 3 under stringent conditions, wherein the stringent conditions are hybridization in 4×SSC at 65° C. followed by washing in 0.1×SSC at 65° C. for one hour,
   (d) a DNA encoding a protein which comprises the amino acid sequence of SEQ ID NO: 2 or 4, in which 5 amino acids or fewer in SEQ ID NO: 2 or 4 have been added, deleted, substituted, and/or inserted, and
   (e) a DNA encoding a protein which has more than 95% identity to the amino acid sequence of SEQ ID NO: 2 or 4.

2. A protein encoded by the DNA according to claim 1.

3. A vector into which the DNA according to claim 1 is inserted.

4. A transformant which retains, in an expressible state, the DNA according to claim 1 or a vector comprising the DNA.

5. A method of screening for a sample having antimalarial activity, which comprises the steps of:
   (1) contacting the protein according to claim 2 with a test sample and a labeled compound that has the activity of binding to the protein,
   (2) detecting the labeled compound that binds to the protein, and,
   (3) selecting a sample that decreases the amount of labeled compound that binds to the protein.

6. The method according to claim 5, wherein the labeled compound that has the activity of binding to the protein is produced by labeling at least one compound selected from the group consisting of the following compounds (1) to (5):

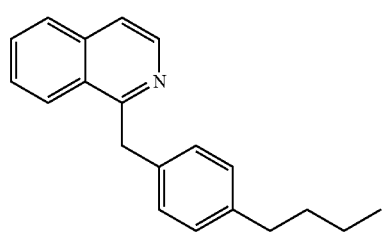

(1)

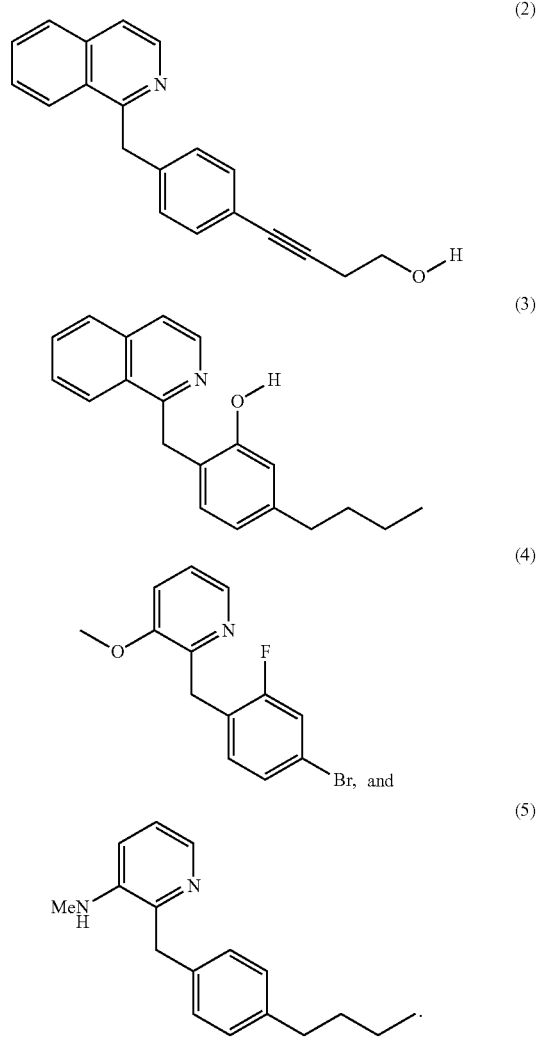

7. A method of screening for a sample having antimalarial activity, which comprises the steps of:
   (1) contacting a test sample with the protein according to claim 2,
   (2) detecting the level of GlcN-(acyl)PI, and,
   (3) selecting a sample that decreases the level of GlcN-(acyl)PI as compared to the level of GlcN-(acyl)PI detected in the absence of the test sample.

8. A method of screening for a sample having antimalarial activity, which comprises the steps of:
(1) contacting a test sample with a cell overexpressing the protein according to claim 2,
(2) determining the amount of GPI-anchored protein transported to the cell wall in the cell, and,
(3) selecting a sample that decreases the amount of the GPI-anchored protein transported to the cell wall, as determined in step (2).

9. A method for treating malaria, which comprises administering a compound that inhibits the activity of the protein according to claim 2.

10. The method according to claim 9, wherein the compound is selected from the group consisting of the following compounds (1) to (5):

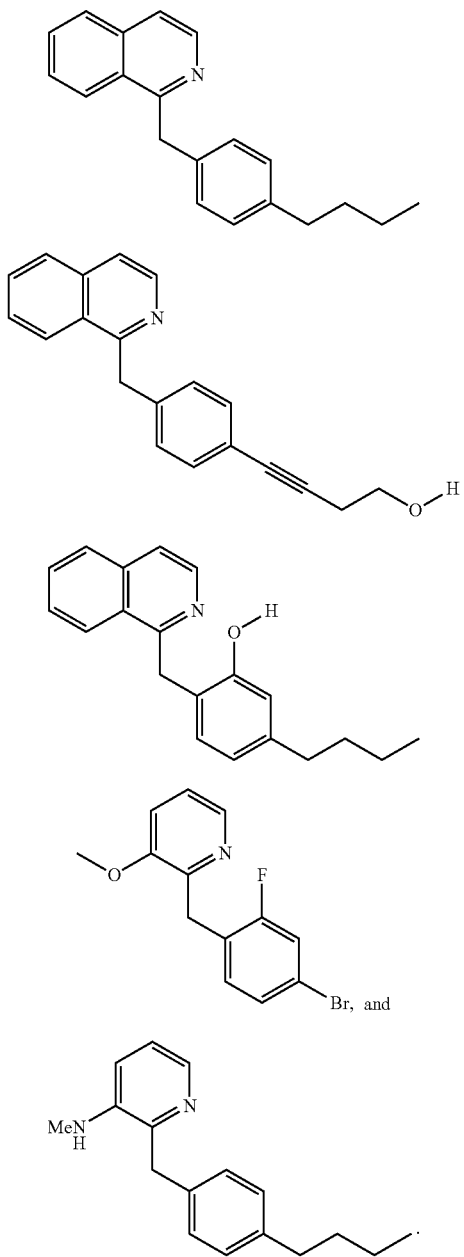

11. An isolated DNA encoding a protein that has the activity of complementing the phenotype of a GPI synthase gene-deficient yeast, which is a degenerate mutant of a DNA encoding a protein involved in GPI biosynthesis in malaria parasites, and that has a lower AT content than the original DNA.

12. An isolated DNA encoding a protein that has the activity of rescuing the phenotype of a GPI synthase gene-deficient yeast, which is a degenerate mutant of a DNA encoding a protein involved in the biosynthesis of GPI in malaria parasites, and which has an AT content of 70% or less.

13. The DNA according to claim 11 or 12, which is selected from the group consisting of:
(a) a DNA encoding a protein that comprises any one of the amino acid sequences of SEQ ID NOs: 2 and 4, and odd sequence identification numbers in SEQ ID NOs: 7-47,
(b) a DNA hybridizing under stringent conditions to the DNA that comprises any one of the nucleotide sequences of SEQ ID NOs: 1 and 3, and even sequence identification numbers in SEQ ID NOs: 6-46, wherein the stringent conditions are hybridization in 4×SSC at 65° C. followed by washing in 0.1×SSC at 65° C. for one hour,
(c) a DNA encoding a protein which comprises any one of the amino acid sequences of SEQ ID NOs: 2 and 4, and odd sequence identification numbers in SEQ ID NOs: 7-47, in which 5 amino acids or fewer in SEQ ID NOs: 2 and 4, and odd sequence identification numbers in SEQ ID NOs: 7-47 have been added, deleted, substituted, and/or inserted, and
(d) a DNA encoding a protein which has more than 95% identity to the amino acid sequence of SEQ ID NO: 2 or 4.

14. An isolated DNA comprising the nucleotide sequence of SEQ ID NO: 5.

15. A vector in which the DNA according to any one of claims 11, 12 and 14 is inserted.

16. A transformant which retains, in an expressible state, the DNA according to any one of claims 11, 12 and 14, or a vector comprising the DNA.

17. The transformant according to claim 16, which is a GPI synthase gene-deficient fungus.

18. The transformant according to claim 16, which is a GPI synthase gene-deficient yeast.

19. A method for producing a protein, which comprises the steps of culturing the transformant according to claim 16, and recovering the expressed protein from the transformant or the culture supernatant.

20. A method of screening for a sample having antimalarial activity, which comprises the steps of:
(1) contacting a test sample with a GPI synthase gene-deficient fungus that expresses the DNA according to any one of claims 11, 12 and 14,
(2) assaying the growth of that fungus, and,
(3) selecting a sample that inhibits the growth of that fungus.

21. A method of screening for a sample having antimalarial activity, which comprises the steps of:
(1) contacting a test sample with a GPI synthase gene-deficient fungus expressing the DNA according to any one of claims 11, 12 and 14,
(2) determining the amount of a GPI-anchored protein transported to the fungal cell wall, and,
(3) selecting a sample that decreases the amount of the GPI-anchored protein transported to the cell wall, as determined in step (2).

22. A method of screening for a sample having antimalarial activity, which comprises the steps of:
  (1) introducing the DNA according to any one of claims 11, 12 and 14 into a GPI synthase gene-deficient fungus and expressing the protein encoded by the DNA,
  (2) isolating the protein expressed in step (1) from a cell membrane fraction that is obtained by homogenizing and centrifuging said fungus cells,
  (3) contacting the protein with a test sample and a labeled compound that has the activity of binding to the protein,
  (4) detecting the labeled compound that binds to the protein, and,
  (5) selecting a sample that decreases the amount of labeled compound that binds to the protein.

23. A method of screening for a sample having antimalarial activity, which comprises the steps of:
  (1) introducing into a GWT1-deficient fungus, (i) a DNA encoding a protein that has the activity of complementing the phenotype of a GWT1-deficient yeast, wherein the DNA is a degenerate mutant of a DNA encoding a malaria parasite GWT1 protein that has a lower AT content than the original DNA, or (ii) a vector into which the degenerate mutant of DNA has been inserted, and expressing the protein encoded by the degenerate mutant DNA,
  (2) isolating the protein expressed in step (1) from a cell membrane fraction that is obtained by homogenizing and centrifuging said fungus cells,
  (3) contacting the protein with a test sample,
  (4) detecting the level of GlcN-(acyl)PI, and
  (5) selecting a sample that decreases the level of GlcN-(acyl)PI as compared to the level of GlcN-(acyl)PI detected in the absence of the test sample.

* * * * *